US008258172B2

(12) United States Patent
Greig et al.

(10) Patent No.: US 8,258,172 B2
(45) Date of Patent: *Sep. 4, 2012

(54) AGENTS USEFUL FOR REDUCING AMYLOID PRECURSOR PROTEIN AND TREATING DEMENTIA AND METHODS OF USE THEREOF

(75) Inventors: Nigel H. Greig, Phoenix, MD (US); Karen T. Y. Shaw, St. Laurent (CA); Qiang-Sheng Yu, Lutherville, MD (US); Harold W. Holloway, Middle River, MD (US); Tada Utsuki, West Chester, PA (US); Timothy T. Soncrant, Silver Spring, MD (US); Donald K. Ingram, Ellicott City, MD (US); Arnold Brossi, Bethesda, MD (US); Anthony Giordano, Phoenixville, PA (US); Gordon Powers, Malvern, PA (US); Diane M. Davidson, Collegeville, PA (US); Michael Sturgess, Quakertown, PA (US)

(73) Assignees: Raptor Pharmaceutical Corp, Novato, CA (US); National Institutes of Health (NIH), Bethesda, MD (US)

( * ) Notice: Subject to any disclaimer, the term of this patent is extended or adjusted under 35 U.S.C. 154(b) by 97 days.

This patent is subject to a terminal disclaimer.

(21) Appl. No.: 12/841,888

(22) Filed: Jul. 22, 2010

(65) Prior Publication Data

US 2011/0021594 A1 Jan. 27, 2011

Related U.S. Application Data

(63) Continuation of application No. 12/357,115, filed on Jan. 21, 2009, now Pat. No. 7,786,162.

(51) Int. Cl.
*A61K 31/40* (2006.01)
(52) U.S. Cl. .................................................. 514/411
(58) Field of Classification Search .................. 514/411
See application file for complete search history.

(56) References Cited

U.S. PATENT DOCUMENTS

| 2,890,223 | A | 6/1959 | Woley et al. |
| 4,791,107 | A | 12/1988 | Hamer et al. |
| 4,900,748 | A | 2/1990 | Brossi et al. |
| 5,171,750 | A | 12/1992 | Brossi et al. |
| 5,378,723 | A | 1/1995 | Brossi et al. |
| 5,403,851 | A | 4/1995 | D'Orlando et al. |
| 5,726,323 | A | 3/1998 | Glamkowski et al. |
| 6,410,747 | B1 | 6/2002 | Greig et al. |
| 6,683,105 | B2 | 1/2004 | Greig et al. |
| 6,706,750 | B1 | 3/2004 | Bentley et al. |
| 7,153,882 | B2 * | 12/2006 | Greig et al. ............. 514/411 |
| 2001/0007877 | A1 | 7/2001 | Burton et al. |
| 2002/0004198 | A1 | 1/2002 | Hardwicke |

FOREIGN PATENT DOCUMENTS

| EP | 0506532 | 9/1992 |
| JP | 7-271066 | 10/1995 |
| WO | WO 95/01334 | 1/1995 |
| WO | WO 96/03377 | 2/1996 |
| WO | WO 99/02154 | 1/1999 |
| WO | WO 99/43654 | 9/1999 |
| WO | WO 01/34146 | 5/2001 |
| WO | WO 01/78721 | 10/2001 |

OTHER PUBLICATIONS

Adem et al., "Muscarinic receptors in human SH-SY5Y neuroblastoma cell line: regulation by phorbol ester and retinoic acid-induced differentiation." *Dev. Brain Res.* 33:235-242 (1987).
Akiyama et al., "Inflammation and Alzheimer's disease." *Neurobiol. Aging* 21:383-421 (2000).
Atack et al., "Comparative Inhibitory Effects of Various Physostigmine Analogs Against Acetyl- and Butyrylcholinesterases." *J. Pharmacol. Exp. Ther.* 249:194 (1989).
Becker et al., "The second generation of cholinesterase inhibitors: clinical and pharmacological effects." *The Cholinergic Basis for Alzheimer Therapy*. Becker et al., eds. Birkhauser, Boston, 263-296 (1991).
Bhasker et al., "The Putative Iron-Responsive Element in the Human Erythroid 5-Aminolevulinate Synthase mRNA Mediates Translational Control." *J. Biol. Chem.* 268(17):12699-12705 (Jun. 15, 1993).
Borchelt et al., "Accelerated Amyloid Deposition in the Brains of Transgenic Mice Coexpressing Mutant Presenilin 1 and Amyloid Precursor Proteins." *Neuron.* 19(4):939-945 (Oct. 1997).
Breitner, "Inflammatory Processes and Antiinflammatory Drugs in Alzheimer's Disease: A Current Appraisal." *Neurobiol. Aging* 17(5):789-794 (1996).
Bronfman et al., "Amyloid Precursor Protein Fragment and Acetylcholinesterase Increase with Cell Confluence and Differentiation in a Neuronal Cell Line." *Exp. Cell Res.* 229:93-99 (1996).
Brossi et al., "Phenserine, a Novel Anticholinesterase Related to Physostigmine: Total Synthesis, and Biological Properties." *Austr. J. Chem.* 49:171-181 (1996).
Buxbaum et al., "Processing of Alzheimer □/A4 amyloid precursor protein: Modulation by agents that regulate protein phosphorylation." *Proc. Natl. Acad. Sci. USA* 87(15):6003-6006 (Aug. 1990).
Buxbaum et al., "Calcium regulates processing of the Alzheimer amyloid protein precursor in a protein kinase C-independent manner." *Proc. Natl. Acad. Sci. USA* 91:4489-4493 (May 1994).
Buxbaum et al., "Cholinergic agonists and interleukin 1 regulate processing and secretion of the Alzheimer □/A4 amyloid protein precursor." *Proc. Natl. Acad. Sci. USA* 89:10075-10078 (Nov. 1992).
Caputi et al., Increase Secretion of the Amino-Terminal Fragment of Amyloid Precursor Protein in Brains of Rats with a Constitutive Up-Regulation of Protein Kinase C. *J. Neurochem.* 68(6):2523-2529 (1997).
Checler, "Processing of □-Amyloid Precursor Protein and Its Regulation in Alzheimer's Disease." *J. Neurochem.* 65(4):1431-1444 (1995).

(Continued)

*Primary Examiner* — Rei-tsang Shiao
(74) *Attorney, Agent, or Firm* — Riverside Law LLP

(57) ABSTRACT

The present invention provides compounds and methods of administering compounds to a subject that can reduce βAPP production and that is not toxic in a wide range of dosages. The present invention also provides non-carbamate compounds and methods of administering such compounds to a subject that can reduce βAPP production and that is not toxic in a wide range of dosages. It has been discovered that either the racemic or enantiomerically pure non-carbamate compounds can be used to decrease βAPP production.

25 Claims, 36 Drawing Sheets

OTHER PUBLICATIONS

Desdouits et al., "Amyloid β Peptide Formation in Cell-Free Preparations: Regulation by protein kinase C, calmodulin and calcineurin." *J. Biol. Chem.* 271(40):24670-24674 (Oct. 4, 1996).

Desdouits-Magnen et al., "Regulation of Secretion of Alzheimer Amyloid Precursor Protein by the Mitogen-Activated Protein Kinase Cascade." *J. Neurochem.* 70(2):524-530 (1998).

Dyrks et al., "Amyloid precursor protein secretion and βA4 amyloid generation are not mutually exclusive." *FEBS Lett.* 349:210-214 (1994).

Eisenstein et al., "Iron-responsive Element-binding Protein: phosphorylation by protein kinase C." *J. Biol. Chem.* 268(36):27363-27370 (Dec. 25, 1993).

Felder et al., "Muscarinic Acetylcholine Receptor Subtypes Associated with Release of Alzheimer Amyloid Precursor Derivatives Activate Multiple Signal Transduction Pathways." *Ann. NY Acad. Sci.* 695:15-18 (1993).

Funato et al., "Astrocytes Containing Amyloid b-Protein (Aβ)-Positive Granules Are Associated with Aβ40-Positive Diffuse Plaques in the Aged Human Brain." *Am. J. Path.* 152(4):983-992 (Apr. 1998).

Giacobini et al., "The Effect of Cholinesterase Inhibitors on the Secretion of APPS from Rat Brain Cortex." *Ann. NY Acad. Sci* 777:393-398 (1996).

Greig et al., "Phenserine and Ring-C Hetero-Analogues: Drug Candidates for the Treatment of Alzheimer's Disease." *Med. Chem. Rev.* 15(1):3-31 (1995).

Haroutunian et al., "Pharmacological modulation of Alzheimer's β-amyloid precursor protein levels in the CSF of rats with forebrain cholinergic system lesions." *Mol. Brain Res.* 46(1-2):161-168 (1997).

He et al., Thiaphysovenine and Carbamate Analogues: A New Class of Potent Inhibitors of Cholinesterases: *Med. Chem. Res.* 2:229-237 (1992).

Hentze et al., "Molecular control of vertebrate iron metabolism: mRNA-based regulatory circuits operated by iron, nitric oxide, and oxidative stress." *Proc. Natl. Acad. Sci. USA.* 93:8175-8182 (Aug. 1996).

Hung et al., "Selective ectodomain phosphorylation and regulated cleavage of β-amyloid precursor protein." *EMBO J.* 13(3):534-542 (1994).

Hussaain et al., "Identification of a Novel Aspartic Protease (Asp 2) as β-Secretase." *Mol. Cell Neurosci.* 14:419-427 (1999).

Jacobsen et al., The Release of Alzheimer's Disease β Amyloid Peptide is Reduced by Phorbol Treatment: *J. Biol. Chem.* 269(11):8376-8382 (Mar. 18, 1994).

Julian et al., "Studies in the Indole Series. IV. The Synthesis of d,l-Eserethole." *J. Am. Chem. Soc.* 57:563-566 (Mar. 1935).

Kim et al., Identification of a Conserved and Functional Iron-responsive Element in the 5'-Untranslated Region of Mammalian Mitochondrial Aconitase. *J. Biol Chem.* 271(39):24226-24230 (Sep. 27, 1996).

Koike et al., "Thimet Oligopeptidase Cleaves the Full-Length Alzheimer Amyloid Precursor Protein at a β-Secretase Cleavage Site in COS Cell". *J. Biochem.* 126:235-242 (1999).

Lahiri et al., "Effects of Cholinesterase Inhibitors on the Secretion of Beta-Arnyloid Precursor Protein in Cell Cultures." *Ann. NY Acad. Sci.* 26(826):416-421 (1997).

Lahiri et al., "Cholinesterase inhibitors, Beta-amyloid precursor protein and amyloid β-peptidases in Alzheimers disease." *Acta Neurol. Scand. Suppl.* 176:60-67 (2000).

Lahiri et al., The secretion of amyloid β-peptides is inhibited in tacrine-treated human neuroblastoma cell. *Mol. Brain Res.* 62:131-140 (1998).

LeBlanc et al., Protein Kinase C Activation Increases Release of Secreted Amyloid Precursor Protein without Decrease Aβ Production in Human Primary Neuron Cultures.° *J. Neurosci.* 18(8):2907-2913 (Apr. 15, 1998).

Lee Wong, "High-performance liquid chromatographic enantioseparation of intermediates relating to the total synthesis of (−)-physostigmine." *J. Chromat.* 523:317-320 (1990).

Lee et al., "Asymmetric Alkylation of Oxindoles: An Approach to the Total Synthesis of (−)-Physostiomine."*J. Org. Chem.* 56:872-875 (1991).

Leli et al., "Distinct Mechanism of Differentiation of SH-SY5Y Neuroblastoma Cells by Protein Kinase C Activators and Inhibitors." *J. Neurochem.* 58(4):1191-1198 (1992).

Matsuura et al., "Catalytic Asymmetric Synthesis of Either Enantiomer of the Calabar Alkaloids Physostigmine and Physovenine." *J. Am. Chem. Soc.* 120(26):6500-6503 (1998).

Melefors et, "Translational Control of 5-Aminolevulinate Synthase mRNA by Iron-responsive Elements in Erythroid Cells." *J. Biol. Chem.* 268(8):5974-5978 (Mar. 15, 1993).

Nitsch et al., "Regulation of APP Processing by First Messengers" *Alzheimer Disease: Therapeutic Strategies.* Giacobini et al., eds. Birkhauser, Boston. pp. 54-61 (1994).

Nitsch et al., "Release of Alzheimer Amyloid Precursor Derivatives Stimulated by Activation of Muscarinic Acetylcholine Receptors." *Science* 258:304-307 (Oct. 9, 1992).

Patel et al., "Phenserine, a novel acetylcholinesterase inhibitor, attenuates impaired learning of rats in a 14-unit T-maze induced by blockade of the N-methyl-D-aspartate receptor." *Neuroreport.* 9(1):171-176 (1998).

Pei et al., "125. Total Synthesis of Racemic and Optically Active Compounds Related to Physostigmine and Ring-C Heteroanaloues from 3-[2'-(Dimethylamino)ethy11-2,3-dihydro-5-methoxy-1,3-dimethyl-1H-indol-2-ol." *Helv. Chem. Acta.* 77:1412-1422 (1994).

Pei et al.,"Facile Preparation of (3S)-1,3-Dimethyl-3-cyanomethyl-5-ethoxyoxindole from Julian's Nitrile Enriched in the (3S)-Enantiomer." *Heterocycles* 41(12):2823-2826 (1995).

Pei et al., "Preparation and Selective Inhibition of Human Butyrylcholinesterase by N1-Phenethylnorphysostigmine Analogues." *Med. Chem. Res.* 5:455-461 (1995).

Pei et al., "Inhibition of Human Acetylcholinesterase by Unnatural (+)-(3aR)-N1-Norphysostigmine and Arylcarbamate." *Med. Chem. Res.* 5:265-270 (1995).

Pei et al., "Syntheses and Biological Evaluation of Ring-C Opened Analogues of the Cholinesterase Physostigmine, Phenserine and Cymserine." *Med. Chem. Res.* 9(1):50-60 (1999).

Roberson et al., "Cholinergic activity and amyloid precursor protein metabolism." *Brain Res. Rev.* 25:50-69 (1997).

Rogers et al., "Translation of the Alzheimer Amyloid Precursor Protein mRNA is Up-regulated by Interleukin 1 through 5'-untranslated Region Sequences." *J. Biol. Chem.* 274(10):6421-6431 (Mar. 5, 1999).

Savage et al., "Turnover of Amyloid β-Protein in Mouse Brain and Acute Reduction of Its Level by Phorbol Ester." *J. Neurosci.* 18(5):1743-1752 (Mar. 1, 1998).

Schalinske et al., "Iron Differentially Stimulates Translation of Mitochondrial Aconitase and Ferritin mRNAs in Mammalian Cells: Implications for iron regulatory proteins as regulators of mitochondrial citrate utilization." *J. Biol. Chem.* 273(6):3740-3746 (Feb. 6, 1998).

Selkoe, "Alzheimer's Disease: Genotypes, Phenotypes, and Treatments." *Science* 275:630-631 (Jan. 31, 1997).

Sinha et al., "Purification and cloning of amyloid precursor protein β-secretase from human brain." *Nature* 402:537-540 (1999).

Suzuki et al., "An Increased Percentage of Long Amyloid-β Protein Secreted by Familial Amyloid-β Protein-Precursor (13-APP717) Mutants." *Science* 264:1336-1340 (May 27, 1994).

Vassar et al., "β-Secretase Cleavage of Alzheimer's Amyloid Precursor Protein by the Transmembrane Aspartic Protease BACE." *Science* 286:735-741 (Oct. 22, 1999).

Waskiewics et al., "Mitogen and stress response pathways: MAP kinase cascades and phosphates regulation in mammals and yeast." *Curr. Opin. Cell Biol.* 7:798-805 (1995).

Wisniewski et al., "Review—David Oppenheimer Memorial Lecture 1995: Some neuropathological aspects of Alzheimer's disease and its relevance to other disciplines." *Neuropethol. Appl. Neurobiol.* 22(1):3-11 (1996).

Xu et al., "Regulated Formation of Golgi Secretory Vesicles Containing Alzheimer β-Amyloid Precursor Protein." *J. Biol. Chem.* 270(40):23243-23245 (Oct. 6, 1995).

Yan et al., "Membrane-anchored aspartyl protease with Alzheimer's disease β-secretase activity." *Nature* 402:533-537 (1999).

Yu et al., "Synthesis and Anticholinesterase Activity of (−)-N1-Norphysostigmine, (−)-Eseramine and Other N(1)-Substituted Analogues of (−)-Physostigmine." *J. Med. Chem.* 31:2297-2300 (Dec. 1988).

Yu et al., "Physovenines: Efficient Synthesis of (−)- and (+)-Physovenine and Synthesis of Carbamate Analogues of (−)-Physovenine. Anticholinesterase Activity and Analgesic Properties of Optically Active Physovenines." *Helv. Chimica. Acta.* 74:761-764 (1991).

Yu et al., "Progress Towards a Practical Total Synthesis of Calabar Alkaloids: Total Synthesis of (−)-Esermethole and (−)-Physovenol Methyl Ether From (3s)-1,3-Dimethyl-3-Carboxymethyl-5-Methoxyoxinbole." *Heterocycles* 36(6):1279-1285 (1993).

Yu et al., "Synthesis and Anticholinesterase Activities of (3aS)-N1,N8-Bisnorphenserine, (3aS)-N1,N8-Bisnorphysostigmine, Their Antipodal Isomers, and Other Potential Metabolites of Phenserine." *J. Med. Chem.* 41:2371-2379 (1998).

Yu et al., "Synthesis of Novel Phenserine-Based-Selective Inhibitors of Butyrylcholinesterase for Alzheimers Disease." *J. Med. Chem.* 42(10):1855-1861 (1999).

Yu et al., "Total Synthesis of Racemic Physostigmine, Physovenine and Its Sulfur Analogue by the Oxindole-5-O-Tetrahydropyranyl Ether Route." *Heterocycles* 39(2):519-525 (1994).

Yu et al., "Practical Synthesis of Unnatural (+)-Physostigmine and Carbamate Analogues." *Heterocycles* 27(3):745-751 (1988).

Yu et al., "Total Synthesis and Anticholinsterase Activities of (3aS)-N(8)-Norphysostigmine, (3aS)-N(8)-Norphenserine, Their Antipodal Isomers, and Other N(8)-Substituted Analogues." *J. Med. Chem.* 40:2895-2901 1997.

Zhu et al., "A practical conversion of natural physostigme into the potent butyrylcholinesterase inhibitor N1,N8-bisnorcymserine." *Tet. Lett.* 41:4861-4864 (2000).

\* cited by examiner

Figure 2. Transformation of (+)-N1-nor-esermethole to analogues of (+)-physostigmine

(B)
|  | None | Transfected cells | | |
|---|---|---|---|---|
| Time (hr) | 0 | 0 | 0.25 | 0.5 | 1 |
5'UTR APP pSV2-CAT 
pSV2-CAT Vector alone 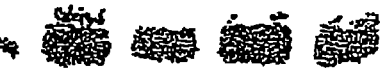
FIGURE 8B

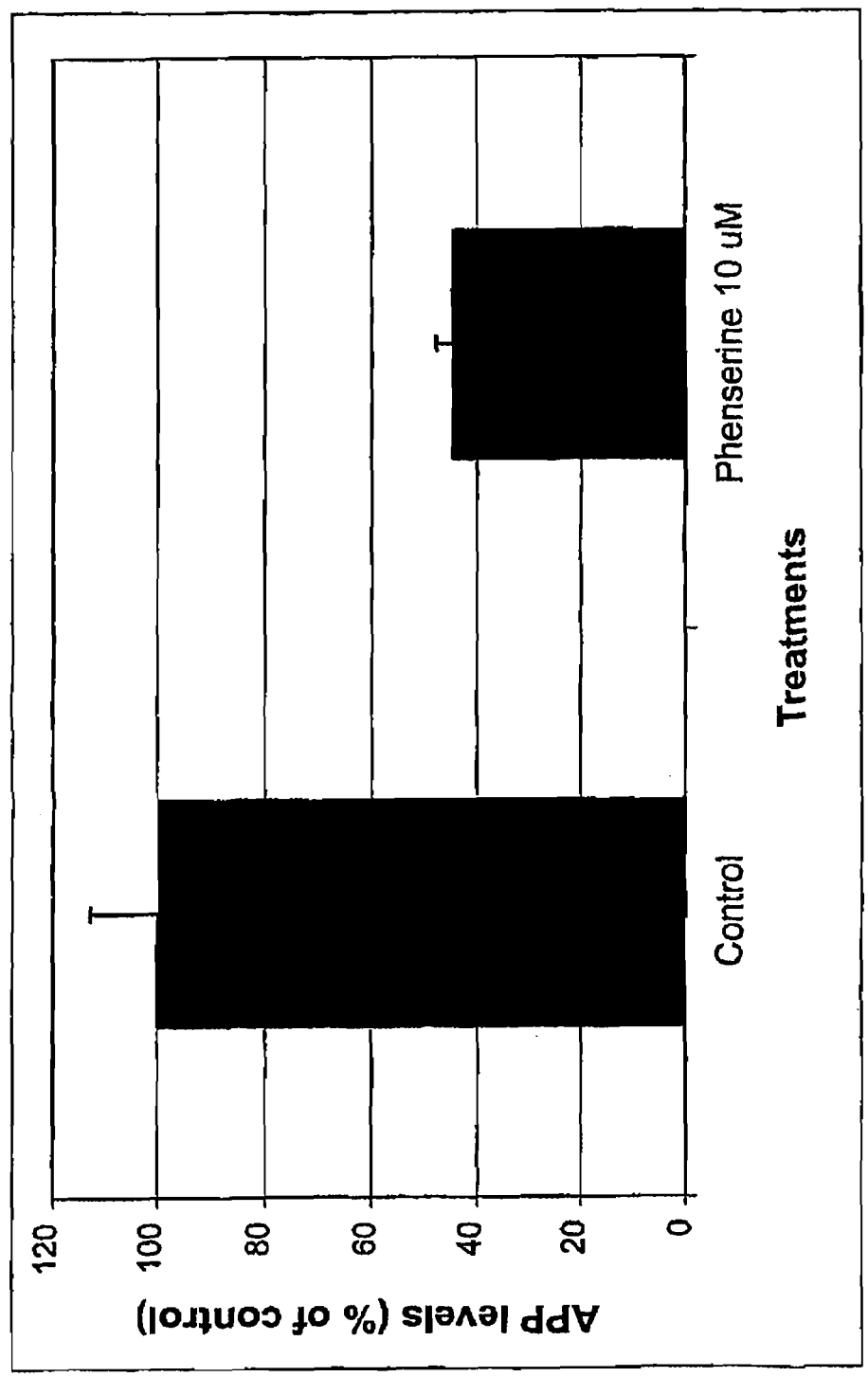

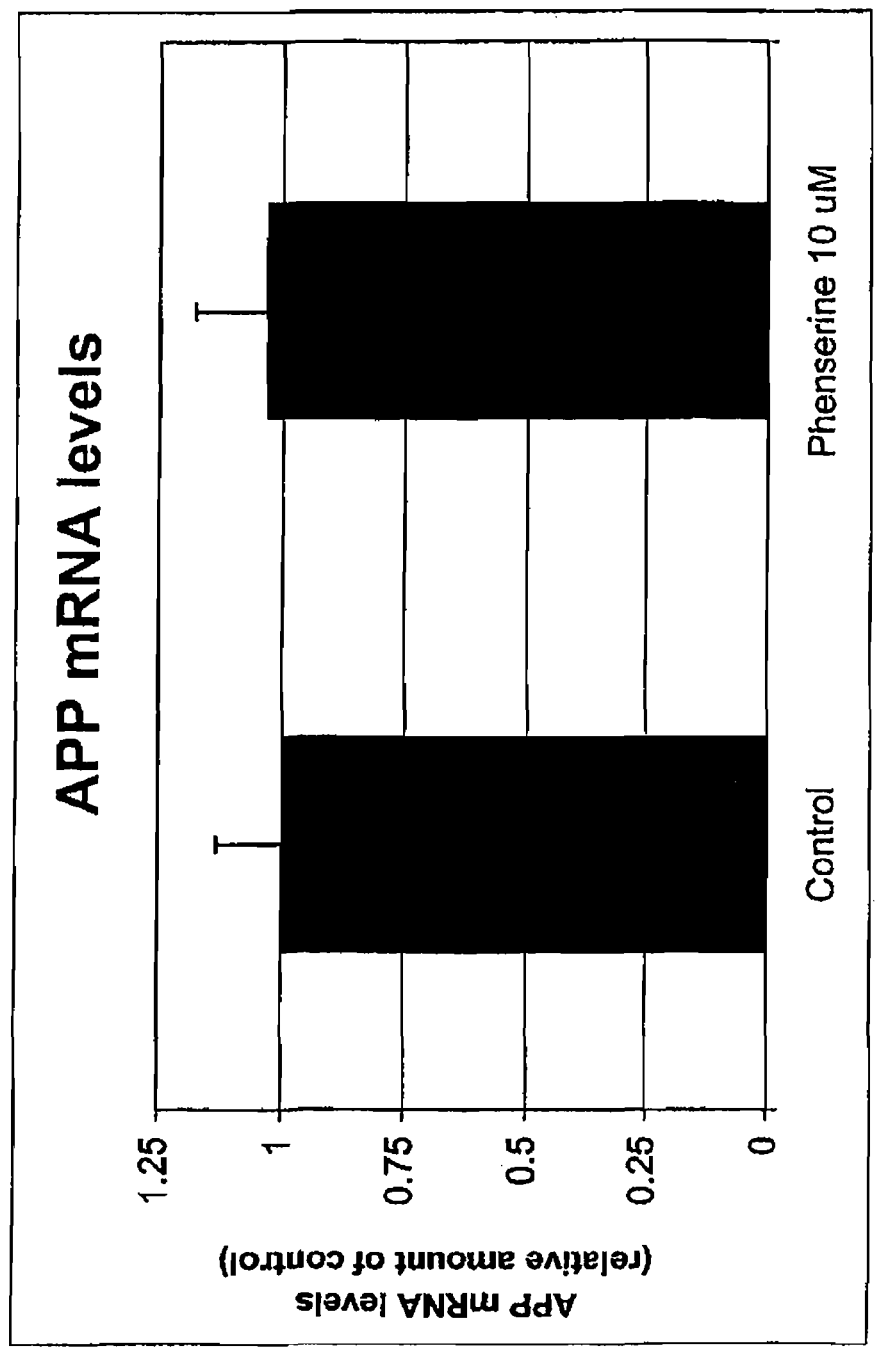

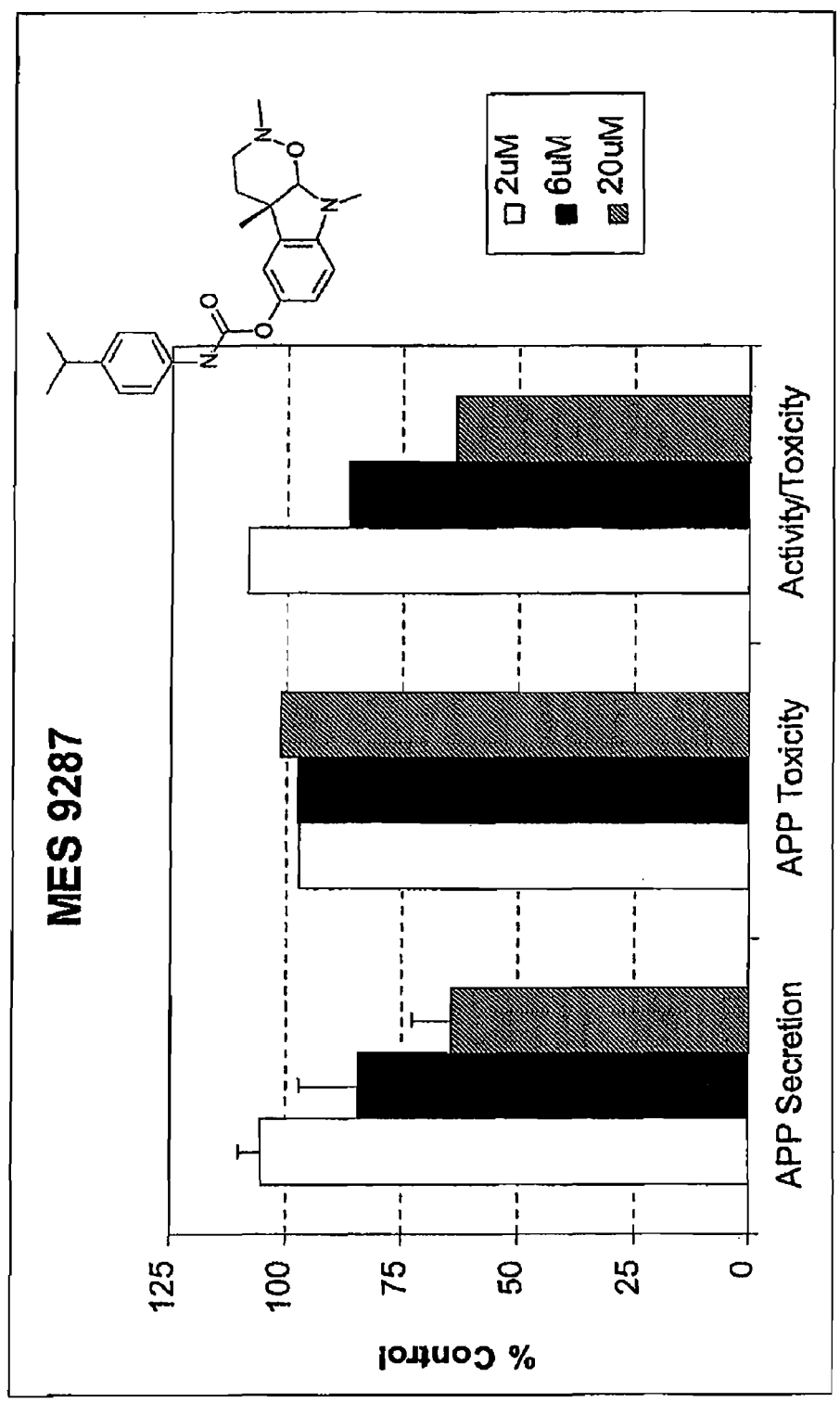

AGENTS USEFUL FOR REDUCING AMYLOID PRECURSOR PROTEIN AND TREATING DEMENTIA AND METHODS OF USE THEREOF

CROSS REFERENCE TO RELATED APPLICATIONS

The present application is a continuation of and claims the benefit of U.S. application Ser. No. 12/357,115, filed Jan. 21, 2009 now U.S. Pat. No. 7,786,162, now allowed, which claims priority to U.S. application Ser. No. 11/455,959, filed Jun. 20, 2006, now abandoned, which claims priority to U.S. application Ser. No. 10/415,765, filed Feb. 6, 2004, now issued as U.S. Pat. No. 7,153,882, which is a 35 U.S.C. §371 national phase application from, and claims priority to, International Application PCT/US01/48175, filed Nov. 2, 2001 and published under PCT Article 21(2) in English, which claims priority to U.S. Provisional Application No. 60/245,329, filed Nov. 2, 2000, which applications are incorporated herein in their entireties by reference.

FIELD OF THE INVENTION

The present invention relates to agents useful for reducing amyloid precursor protein and methods of use thereof.

BACKGROUND OF THE INVENTION

The major pathological hallmarks of Alzheimer's disease (AD), a progressive neurodegenerative condition leading to loss of memory, are characterized by the appearance of senile plaques which are primarily composed of Aβ and neurofibrillary tangle aggregates (Selkoe, 1997; Roberson and Harrell, 1997). Aβ, a 40-42 residue peptide, is derived from a larger protein, βAPP (695-770, amino acids), whose biological functions remain to be fully determined but whose pathological role may be separated on the basis of its final proteolysed form (Checker, 1995; Selkoe, 1997). βAPP derivatives are generated by three enzymatic activities termed α-, β- and γ-secretases, to produce different protein fragments that are either neuroprotective or amyloidogenic. An aspartyl protease with (β-secretase like properties has been identified (Hussaain et al., 1999; Sinha et al., 1999; Vassar et al., 1999; Yan et al., 1999), that may serve as a therapeutic marker. However, its value as a target for drug development is complicated by its location within two membranes (plasma and Golgi apparatus). Furthermore, the role of alternative compensatory activities remains unclear. Indeed, a second enzyme, Thimet oligopeptidase, was found capable of (β-secretase activity in transfected COS cells (Koike et al., 1999). A major pharmaceutical industry focus has been to look for agents that reduce amyloidogenic processing using compounds that can manipulate βAPP to produce non-amyloidogenic by-products. However, it is important to note that the role of alternative βAPP fragments in AD is unclear.

Regarding regulatory mechanisms involved in βAPP processing, environmental agents have been demonstrated to accelerate βAPP turnover into its pathological Aβ form (Selkoe, 1997). Furthermore, the cellular surrounding of neurons, particularly astrocytes and microglia, are additional and non-neuronal sources of βAPP (Funato et al., 1998; Akiyama et al., 2000). Thus, amyloid plaque occurrence is often associated with enlarged microglia which produce interleuken-1 (EL-1), a potent mediator of astroglial proliferation and βAPP production (Akiyama et al., 2000). The fact that IL-1 can influence this process suggests that signaling pathways induced by cytokines are interconnected with βAPP metabolism. Another example of receptor-signaling association and βAPP homeostasis is demonstrated through the activation of muscarinic m1 and m3 receptors which modify βAPP synthesis and processing through MAP kinase dependent and independent pathways (Felder et al., 1993; Nitsch et al., 1992 and 1994). Reductions in muscarinic receptors, as in Aβ, may alter βAPP metabolism and result in subsequent Aβ deposition. Cholinergic system impairment has been reversed with moderate success by the use of anticholinesterases (Greig et al., 1995; Brossi et al., 1996), the only approved drugs for Aβ treatment.

A family of novel anticholinesterases, phenserine and analogues, has been synthesized. Phenserine dramatically improves cognitive performance in rodents and is in clinical trails (Greig et al., 1995; Patel et al., 1998). Studies of rats with forebrain cholinergic lesions that are known to dramatically increase βAPP in cholinergic projection areas have shown that phenserine can protect against this and additionally, reduce βAPP production in naive animals (Haroutunian et al., 1997). As both βAPP processing and cholinesterase activity are affected in the Aβ brain (Bronfman et al., 1996) and as the anticholinesterase, tacrine, has been shown to decrease βAPP and Aβ in neuronal cells in vitro (Lahiri et al., 1998), current studies have focused on the molecular changes induced by phenserine. In these studies, naturally-occurring phenserine (the (−)-enantiomer) was used.

It is the cholinergic action of anticholinesterases such as (−)-phenserine, rivastigmine (Exellon®, Novartis®), donepezil (Aricept®, Pfizer®), galanthamine (Jansen®), tacrine (Cognex®, Warner Lambert®), (−)-physostigmine (Synapton®, Forest®), that provides the compounds their ability to improve cognitive performance in both animal models and humans. Likewise, it is the cholinergic action that is also dose limiting for these same compounds (nausea, sweating, GI effects) (Becker et al., 1991). Conversely, the (+)-enantiomers are unable to inhibit either acetylcholinesterase (AChE., EC 3.1.1.7.) or butyrylcholinesterase (BChE., EC 3.1.1.8.), and hence have no cholinergic action. The (+)-enantiomers are also unnatural isomers and thus, need to be synthesized. Synthetic procedures provide a mixture of (+)- and (−)-forms that require early separation into optically pure forms to eventually obtain the final products.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

SUMMARY OF THE INVENTION

The present invention provides compounds and methods of administering compounds to a subject that can reduce βAPP production and that is not toxic in a wide range of dosages. The present invention also provides non-carbamate compounds and methods of administering such compounds to a subject that can reduce βAPP production and that is not toxic in a wide range of dosages. It has been discovered that either the racemic or enantiomerically pure non-carbamate compounds can be used to decrease βAPP production.

BRIEF DESCRIPTION OF THE DRAWINGS

FIG. 11A shows the translational regulation of phenserine (Rate of APP Synthesis) in SH-SY5Y cells. FIG. 11B shows the effects of (−)-phenserine on steady state APP mRNA levels in SH-SY5Y cells.

FIGS. 13B-M show the effects of several compounds of the invention on secreted APP levels and cell-viability in SH-SY5Y cells.

DETAILED DESCRIPTION OF THE INVENTION

Figure 1:
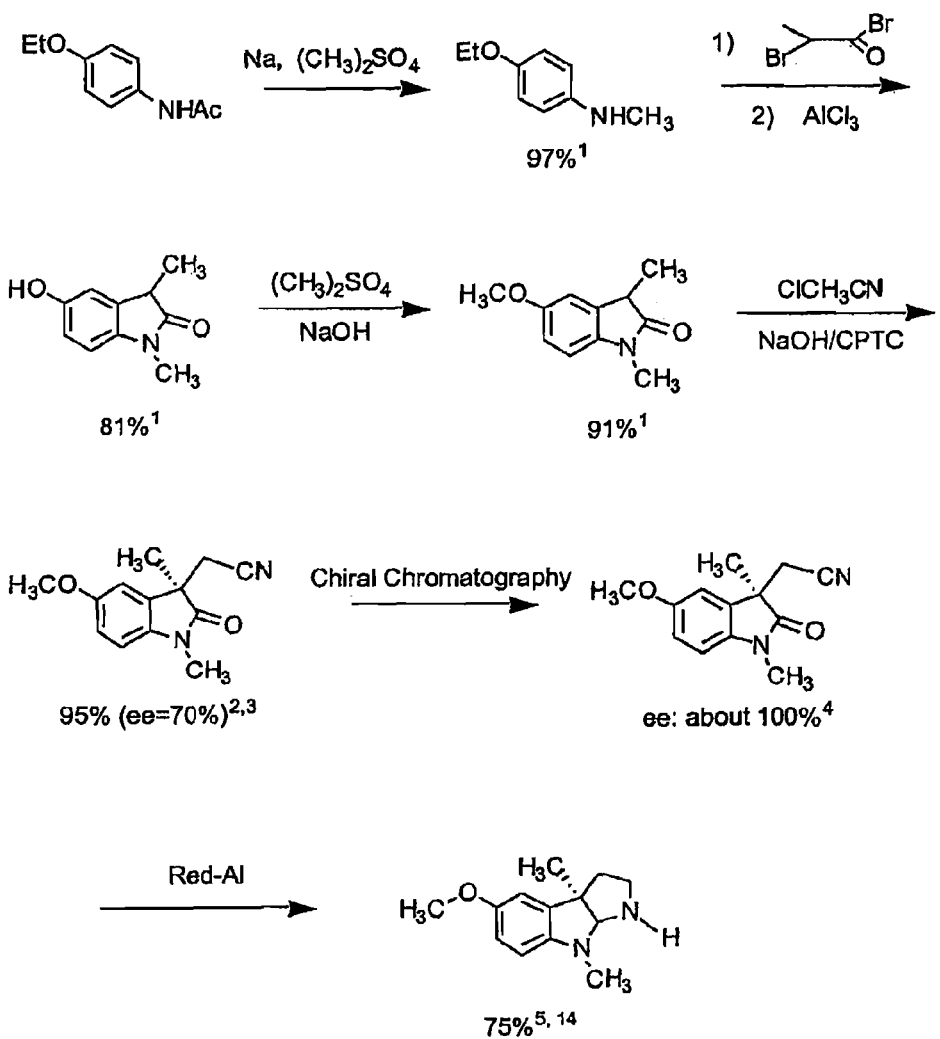
FIG. 1 shows the synthesis of analogues of (+)-physostigmine.

The present invention may be understood more readily by reference to the following detailed description of desired embodiments of the invention and the Examples included therein.

Before the present compounds, compositions and methods are disclosed and described, it is to be understood that this invention is not limited to specific synthetic methods, as such may, of course, vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications and patents are referenced, the disclosures of these publications and patents in their entireties are hereby incorporated by reference into this application in order to more fully describe the state of the art to which this invention pertains.

Variables, such as $R_1$-$R_{15}$, n, A, D, E, G, X, Y, and Z throughout the application are the same variables as previously defined unless stated to the contrary.

In this specification and in the claims which follow, reference will be made to a number of terms which shall be defined to have the following meaning.

The term "alkyl" as used herein refers to a branched or unbranched saturated hydrocarbon group of 1 to 4, 1 to 8, or 1 to 20 carbon atoms, such as methyl, ethyl, n-propyl, isopropyl, n-butyl, isobutyl, t-butyl, pentyl, hexyl, heptyl, octyl, and the like. Examples of cycloalkyl groups include cyclopentyl and cyclohexyl.

The term "alkenyl" as used herein refers to a hydrocarbon group of 2 to 4, 2 to 8, or 2 to 20 carbon atoms and structural formula containing a carbon-carbon double bond.

The term "alkynyl" as used herein refers to a hydrocarbon group of 2 to 4, 2 to 8, or 2 to 20 carbon atoms and a structural formula containing a carbon-carbon triple bond.

The term "aryl" is defined as any carbon-based aromatic group including, but 10 not limited to, phenyl, benzene, naphthalene, anthracene, phenanthrene, pyrene, and benzofalpyrene, etc.

The term "substituted aryl" is defined as an aryl group having at least one group attached to the aryl group that is not hydrogen. Examples of groups that can be attached to the aryl group include, but are not limited to, alkyl, alkynyl, alkenyl, aryl, heterocyclic, halide, nitro, amino, ester, ketone, aldehyde, hydroxy, carboxylic acid, alkoxy, cyano, alkoxy, thioalkyl, haloalkyl, hydroxyalkyl, alkylamino, diakylamino, or acyl. In various embodiments, a substituent is bound to carbon 2, 3, 4, 5, or 6 of one of these moieties. Examples of alkoxy substituents include, but are not limited to, methoxy, ethoxy, and isopropoxy groups. Examples of acyl substituents include acetyl and benzoyl groups.

The term "aralkyl" is defined as an aryl group having an alkyl, alkynyl, or alkenyl group attached to the aryl group. An example of an aralkyl group is a benzyl group.

The term "heteroaryl" is defined as an aryl group that has at least one heteroatom such as nitrogen, sulfur, or oxygen incorporated within the ring of the aryl group.

The term "heteroalkyl" is defined as an alkyl group that has at least one hetero atom, such as nitrogen, sulfur, oxygen, or phosphate, incorporated within the alkyl group or attached to the alkyl group.

The invention, in one aspect, relates to a compound having the formula I or II:

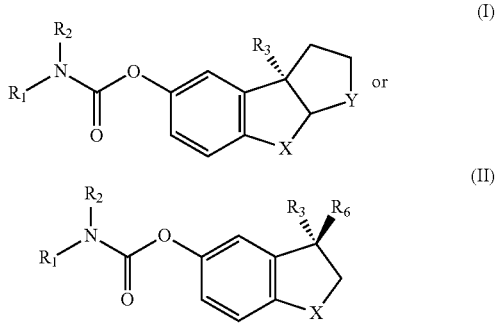

wherein $R_1$ and $R_2$ are, independently, hydrogen, branched or straight chain $C_1$-$C_8$ alkyl, substituted or unsubstituted aryl, or aralkyl;

$R_3$ is branched or straight chain $C_1$-$C_4$ alkyl or heteroalkyl or $C_4$-$C_8$ alkyl or heteroalkyl, or substituted or unsubstituted aryl;

X and Y are, independently, O, S, alkyl, hydrocarbon moiety, C(H)R$_4$, or NR$_5$, wherein R$_4$ and R$_5$ are, independently, hydrogen, oxygen, branched or straight chain C$_1$-C$_8$ alkyl, C$_2$-C$_8$ alkenyl, or C$_2$-C$_8$ alkynyl, aralkyl, or substituted or unsubstituted aryl; and R$_6$ is hydrogen; C$_1$-C$_8$ alkyl, C$_2$-C$_8$ alkenyl, C$_2$-C$_8$ alkynyl, aralkyl, or substituted or unsubstituted aryl, or (CH$_2$)$_n$R$_7$, where R$_7$ is hydroxy, alkoxy, cyano, ester, carboxylic acid, substituted or unsubstituted amino, and n is from 1 to 4, wherein the compound having the formula I or II is the substantially pure (+)-enantiomer, with the proviso that the compound is not (+)-physostigmine, (+)-octylcarbamoyleseroline, (+)-benzylcarbamoyleseroline, (+)-physovenine, (+)-N-methylphysostigmine, (+)-phenserine, (+)-3-(1-methylamino)-ethyl-2H-indol-5yl-phenylcarbamate, (+)-N$^1$-benzylnorphysostigmine, (+)-N$^1$-benzylnorphenserine, (+)-N$^1$-benzylnortolserine, (+)-N-1-benzylnorcymserine, (+)-N$^1$-norphysostigmine, (+)-N$^1$-norphenserine, (+)-N$^1$-nortolserine, (+)-N$^1$-norcymserine, (+)-N$^8$-benzylnorphysostigmine, (+)-N$^8$-benzylnorphenserine, (+)-N$^8$-norphysostigmine, (+)-N$^8$-norphenserine, (+)-N$^1$,N$^8$-bisbenzylnorphysostigmine, (+)-N$^1$,N$^8$-bisbenzylnorphenserine, (+)-N$^1$,N$^8$-bisnorphysostigmine, or (+)-N$^1$,N$^8$-bisnorphenserine, with the proviso that when the compound is formula I, X is NCH$_3$, and Y is NR$_5$, where R$_5$ is hydrogen, loweralkyl, aryloweralkyl, heteroaryloweralkyl, cycloalkylmethyl, or loweralkenyl methyl, R$_3$ is not methyl or at least one of R$_1$ or R$_2$ is not H or alkyl.

The invention also relates to a compound having the formula III or IV:

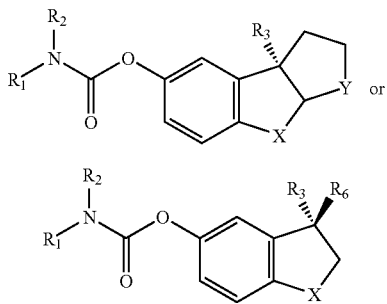

wherein R$_1$ and R$_2$ are, independently, hydrogen, branched or straight chain C$_1$-C$_8$ alkyl, substituted or unsubstituted aryl, or aralkyl;

R$_3$ is branched or straight chain C$_1$-C$_4$ alkyl, or substituted or unsubstituted aryl;

X and Y are, independently, O, S, alkyl, hydrocarbon moiety, C(H)R$_4$, or NR$_5$, wherein R$_4$ and R$_5$ are, independently, hydrogen, oxygen, branched or straight chain C$_1$-C$_8$ alkyl, C$_2$-C$_8$ alkenyl, or C$_2$-C$_8$ alkynyl, aralkyl, or substituted or unsubstituted aryl; and R$_6$ is hydrogen; C$_1$-C$_8$ alkyl, C$_2$-C$_8$ alkenyl, C$_2$-C$_8$ alkynyl, aralkyl, or substituted or unsubstituted aryl, or (CH$_2$)$_n$R$_7$, where R$_7$ is hydroxy, alkoxy, cyano, ester, carboxylic acid, substituted or unsubstituted amino, and n is from 1 to 4, The chiral center of compounds I-IV is the carbon atom that has R$_3$ bonded to it. Here, the (+)-enantiomer has R$_3$ pointing behind the plane of the page. In various embodiments, the compounds having the structure I or II have an enantiomeric purity for the (+)-enantiomer of from 55 to 100%, desirably from 75 to 100%, more desirably from 85 to 100%, more desirably from 95 to 100%, and even more desirably 100%.

In one embodiment, when the compound is formula I, R$_3$ is methyl and X is NCH$_3$.

In one embodiment, when the compound is formula I or II, R$_3$ is not methyl. In particular embodiments, R$_3$ is a branched or straight chain alkyl or heteroalkyl group of 2, 3, 4, 5, 6, 7, or 8 carbons or substituted or unsubstituted aryl.

In another embodiment, when the compound has the structure I or II, Y is C(H)R$_4$ or X is O, S, or C(H)R$_4$.

In another embodiment, when the compound is formula I, R$_3$ is methyl, X is NCH$_3$, and Y is NCH$_3$. In one embodiment, when the compound is formula I, R$_3$ is methyl, X is NCH$_3$, Y is NCH$_3$, and R$_1$ is C$_1$-C$_8$ straight chain alkyl or benzyl and R$_2$ is hydrogen. In one embodiment, when the compound is formula I, R$_3$ is methyl, X is NCH$_3$, Y is NCH$_3$, and R$_1$ is substituted or unsubstituted phenyl and R$_2$ is hydrogen. In one embodiment, when the compound is formula I, R$_3$ is methyl, X is NCH$_3$, Y is NCH$_3$, and R$_1$ and R$_2$ are, independently, methyl or ethyl.

In another embodiment, when the compound is formula I, R$_3$ is methyl, X is NCH$_3$, and Y is O. In one embodiment, when the compound is formula I, R$_3$ is methyl, X is NCH$_3$, Y is O, R$_1$ is C$_1$-C$_8$ straight chain alkyl or benzyl, and R$_2$ is hydrogen. In one embodiment, when the compound is formula I, R$_3$ is methyl, X is NCH$_3$, Y is O, and R$_1$ and R$_2$ are, independently, methyl or ethyl. In one embodiment, when the compound is formula I, R$_3$ is methyl, X is NCH$_3$, Y is O, and R$_1$ is substituted or unsubstituted phenyl and R$_2$ is hydrogen.

In another embodiment, when the compound is formula I, R$_3$ is methyl, X is NCH$_3$, and Y is S. In one embodiment, when the compound is formula I, R$_3$ is methyl, X is NCH$_3$, Y is S, R$_1$ is C$_1$-C$_8$ straight chain alkyl or benzyl, and R$_2$ is hydrogen. In one embodiment, when the compound is formula I, R$_3$ is methyl, X is NCH$_3$, Y is S, and R$_1$ and R$_2$ are, independently, methyl or ethyl. In one embodiment, when the compound is formula I, R$_3$ is methyl, X is NCH$_3$, Y is S, R$_1$ is substituted or unsubstituted phenyl, and R$_2$ is hydrogen.

In another embodiment, when the compound is formula I, R$_3$ is methyl, X is NCH$_3$, and Y is NR$_5$. In one embodiment, when the compound is formula I, R$_3$ is methyl, X is NCH$_3$, and Y is NR$_5$, wherein R$_5$ is —CH$_2$CH=CH$_2$, —CH$_2$CH$_2$Ph, benzyl, or hydrogen.

In another embodiment, when the compound has the formula I, R$_3$ is methyl, Y is NCH$_3$, and X is NCH$_3$, wherein R$_4$ is benzyl or hydrogen.

In another embodiment, when the compound is formula I, R$_3$ is methyl, X is NCH$_3$, Y is NR$_5$, wherein each R$_4$ and R$_5$ is, independently, hydrogen or benzyl.

In another embodiment, when the compound is formula I, R$_3$ is phenyl, X is NCH$_3$, and Y is NCH$_3$.

In another embodiment, when the compound is formula I, R$_3$ is methyl, and X is NCH$_3$, and Y is not NH or NHCH$_2$Ph.

In another embodiment, when the compound is formula II, R$_3$ is methyl, X is C(H)CH$_3$, and R$_6$ is (CHD$_2$R$_7$, where R$_7$ is a substituted or unsubstituted amino group.

In another embodiment, the compound having the formula I or II can be found in Table 1. Although only the (+)-isomer is illustrated to save space, it is the intent of the invention to claim the (+)-isomer, (−)-isomer, and mixtures of both isomers (e.g., racemic 1:1 mixtures) of all of the compounds of the invention unless such compounds are specifically excluded.

TABLE 1

| Structure | No. | R | Compounds |
|---|---|---|---|
| 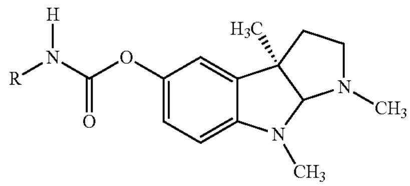 | 1 | CH$_3$ | (+)-Physostigmine |
| | 2 | C$_2$H$_5$ | (+)-Ethylcarbamoyleseroline |
| | 3 | (CH$_2$)$_2$CH$_3$ | (+)-Propylcarbamoyleseroline |
| | 4 | CH$_2$(CH$_3$)$_2$ | (+)-Isopropylcarbamoyleseroline |
| | 5 | (CH$_2$)$_3$CH$_3$ | (+)-Butylcarbamoyleseroline |
| | 6 | (CH$_2$)$_4$CH$_3$ | (+)-Pentylcarbamoyleseroline |
| | 7 | (CH$_2$)$_5$CH$_3$ | (+)-Hexylcarbamoyleseroline |
| | 8 | (CH$_2$)$_6$CH$_3$ | (+)-Heptylcarbamoyleseroline |
| | 9 | (CH$_2$)$_7$CH$_3$ | (+)-Octylcarbamoyleseroline |
| | 10 | CH$_2$C$_6$H$_5$ | (+)-Benzylcarbamoyleseroline |
| 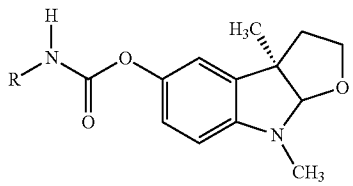 | 11 | CH$_3$ | (+)-Physovenine |
| | 12 | C$_2$H$_5$ | (+)-Ethylcarbamoylphysovenol |
| | 13 | (CH$_2$)$_2$CH$_3$ | (+)-Propylcarbamoyl physovenol |
| | 14 | CH$_2$(CH$_3$)$_2$ | (+)-Isopropylcarbarmoyl physovenol |
| | 15 | (CH$_2$)$_3$CH$_3$ | (+)-Butylcarbamoyl physovenol |
| | 16 | (CH$_2$)$_4$CH$_3$ | (+)-Pentylcarbamoyl physovenol |
| | 17 | (CH$_2$)$_5$CH$_3$ | (+)-Hexylcarbamoyl physovenol |
| | 18 | (CH$_2$)$_6$CH$_3$ | (+)-Heptylcarbamoylphysovenol |
| | 19 | (CH$_2$)$_7$CH$_3$ | (+)-Octylcarbamoyl physovenol |
| | 20 | CH$_2$C$_6$H$_5$ | (+)-Benzylcarbamoyl physovenol |
| 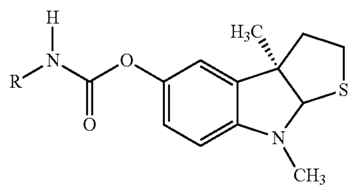 | 21 | CH$_3$ | (+)-Thiaphysovenine |
| | 22 | C$_2$H$_5$ | (+)-Ethylcarbamoylthiaphysovenol |
| | 23 | (CH$_2$)$_2$CH$_3$ | (+)-Propylcarbamoylthia physovenol |
| | 24 | CH$_2$(CH$_3$)$_2$ | (+)-Isopropylcarbamoylthia physovenol |
| | 25 | (CH$_2$)$_3$CH$_3$ | (+)-Butylcarbamoylthia physovenol |
| | 26 | (CH$_2$)$_4$CH$_3$ | (+)-Pentylcarbamoylthia physovenol |
| | 27 | (CH$_2$)$_5$CH$_3$ | (+)-Hexylcarbamoyl physovenol |
| | 28 | (CH$_2$)$_6$CH$_3$ | (+)-Heptylcarbamoylthiaphysovenol |
| | 29 | (CH$_2$)$_7$CH$_3$ | (+)-Octylcarbamoylthia physovenol |
| | 30 | CH$_2$C$_6$H$_5$ | (+)-Benzylcarbamoylthia physovenol |
| 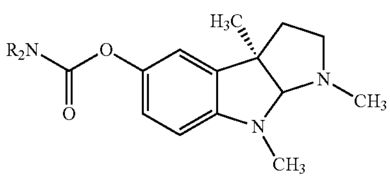 | 31 | CH$_3$ | (+)-N-Methylphysostigmine |
| | 32 | C$_2$H$_5$ | (+)-Diethylcarbamoyleseroline |
| 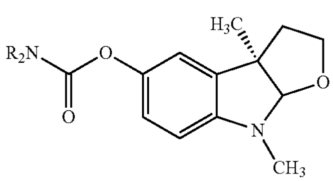 | 33 | CH$_3$ | (+)-N-Methylphysovenine |
| | 34 | C$_2$H$_5$ | (+)-Diethylcarbamoylphysovenol |
| 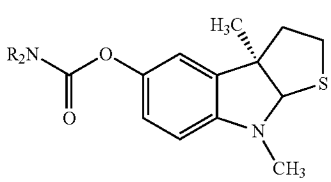 | 35 | CH$_3$ | (+)-N-Methylthiaphysovenine |
| | 36 | C$_2$H$_5$ | (+)-Diethylcarbamoylthiaphysovenol |
| 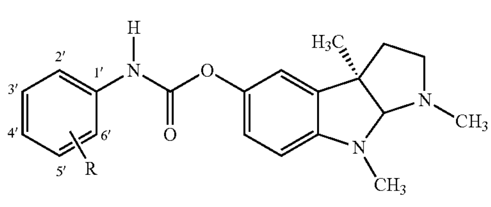 | 37 | H | (+)-Phenserine |
| | 38 | 2'-CH$_3$ | (+)-Tolserine |
| | 39 | 3'-CH$_3$ | (+)-3'-Methylphenserine |
| | 40 | 4'-CH$_3$ | (+)-4'-Methylphenserine |
| | 41 | 2'-CH$_2$CH$_3$ | (+)-2'-Ethylphenserine |
| | 42 | 3'-CH$_2$CH$_3$ | (+)-3'-Eethylphenserine |
| | 43 | 4'-CH$_2$CH$_3$ | (+)-4'-Eethylphenserine |
| | 44 | 2'-CH$_2$(CH$_3$)$_2$ | (+)-2'-Isopropylphenserine |
| | 45 | 3'-CH$_2$(CH$_3$)$_2$ | (+)-3'-Isopropylphenserine |
| | 46 | 4'-CH$_2$(CH$_3$)$_2$ | (+)-Cymserine |
| | 47 | 2',3'-CH$_3$ | (+)-2',3'Dimethylphenserine |
| | 48 | 2',4'-CH$_3$ | (+)-2',4'-Dimethylphenserine |
| | 49 | 2',5'-CH$_3$ | (+)-2',5'-Dimethylphenserine |
| | 50 | 2',6'-CH$_3$ | (+)-2',6'-Dimethylphenserine |
| | 51 | 3',4'-CH$_3$ | (+)-3',4'-Dimethylphenserine |
| | 52 | 3',5'-CH$_3$ | (+)-3'5'-Dimethylphenserine |
| | 53 | 3',6'-CH$_3$ | (+)-3',6'-Dimethylphenserine |
| | 54 | 2',4',6'-CH$_3$ | (+)-2',4',6'-Trimethylphenserin |

TABLE 1-continued

| Structure | No. | R | Compounds |
|---|---|---|---|
| (phenylcarbamoyl-physovenol core, furan oxygen) | 55 | H | (+)-Phenylcarbamoyl-physovenol |
| | 56 | 2'-CH$_3$ | (+)-2'-Methylphenylcarbamoyl-physovenol |
| | 57 | 3'-CH$_3$ | (+)-3'-Methylphenylcarbamoyl-physovenol |
| | 58 | 4'-CH$_3$ | (+)-4'-Methyl phenyl carbamoyl-physovenol |
| | 59 | 2'-CH$_2$CH$_3$ | (+)-2'-Ethylphenylvarbamoyl-physovenol |
| | 60 | 3'-CH$_2$CH$_3$ | (+)-3'-Eethylphenylcarbamoyl-physovenol |
| | 61 | 4'-CH$_2$CH$_3$ | (+)-4'-Eethylphenycarbamoyl-physovenol |
| | 62 | 2'-CH$_2$(CH$_3$)$_2$ | (+)-2'-Isopropylphenylcarbamoyl-physovenol |
| | 63 | 3'-CH$_2$(CH$_3$)$_2$ | (+)-3'-Isopropylphenylcarbamoyl-physovenol |
| | 64 | 4'-CH$_2$(CH$_3$)$_2$ | (+)-4'-Isopropylphenylcarbamoyl-physovenol |
| | 65 | 2',3'-CH$_3$ | (+)-2',3'-Dimethylphenylcarbamoyl-physovenol |
| | 66 | 2',4'-CH$_3$ | (+)-2',4'-Dimethylphenylcarbamoyl-physovenol |
| | 67 | 2',5'-CH$_3$ | (+)-2',5'-Dimethylphenylcarbamoyl-physovenol |
| | 68 | 2',6'-CH$_3$ | (+)-2',6'-Dimethylphenylcarbamoyl-physovenol |
| | 69 | 3',4'-CH$_3$ | (+)-3',4'-Dimethylphenylcarbamoyl-physovenol |
| | 70 | 3',5'-CH$_3$ | (+)-3',5'-Dimethylphenyl carbamoyl-physovenol |
| | 71 | 3',6'-CH$_3$ | (+)-3',6'-Dimethylphenylcarbamoyl-physovenol |
| | 72 | 2',4',6'-CH$_3$ | (+)-2',4',6'-Trimethylphenylcarbamoyl-physovenol |
| (phenylcarbamoyl-thiaphysovenol core, thiophene sulfur) | 55 | H | (+)-Phenylcarbamoyl-thiaphysovenol |
| | 56 | 2'-CH$_3$ | (+)-2'-Methylphenylcarbamoyl-thiaphysovenol |
| | 57 | 3'-CH$_3$ | (+)-3'-Methylphenylcarbamoyl-thiaphysovenol |
| | 58 | 4'-CH$_3$ | (+)-4'-Methyl phenyl carbamoyl-thiaphysovenol |
| | 59 | 2'-CH$_2$CH$_3$ | (+)-2'-Ethylphenylvarbamoyl-thiaphysovenol |
| | 60 | 3'-CH$_2$CH$_3$ | (+)-3'-Eethylphenylcarbamoyl-thiaphysovenol |
| | 61 | 4'-CH$_2$CH$_3$ | (+)-4'-Eethylphenycarbamoyl-thiaphysovenol |
| | 62 | 2'-CH$_2$(CH$_3$)$_2$ | (+)-2'-Isopropylphenylcarbamoyl-thiaphysovenol |
| | 63 | 3'-CH$_2$(CH$_3$)$_2$ | (+)-3'-Isopropylphenylcarbamoyl-thiaphysovenol |
| | 64 | 4'-CH$_2$(CH$_3$)$_2$ | (+)-4'-Isopropylphenylcarbamoyl-thiaphysovenol |
| | 65 | 2',3'-CH$_3$ | (+)-2',3'-Dimethylphenylcarbamoyl-thiaphysovenol |
| | 66 | 2',4'-CH$_3$ | (+)-2',4'-Dimethylphenylcarbamoyl-thiaphysovenol |
| | 67 | 2',5'-CH$_3$ | (+)-2',5'-Dimethylphenylcarbamoyl-thiaphysovenol |
| | 68 | 2',6'-CH$_3$ | (+)-2',6'-Dimethylphenylcarbamoyl-thiaphysovenol |
| | 69 | 3',4'-CH$_3$ | (+)-3',4'-Dimethylphenylcarbamoyl-thiaphysovenol |
| | 70 | 3',5'-CH$_3$ | (+)-3',5'-Dimethylphenyl carbamoyl-thiaphysovenol |
| | 71 | 3',6'-CH$_3$ | (+)-3',6'-Dimethylphenylcarbamoyl-thiaphysovenol |
| | 72 | 2',4',6'-CH$_3$ | (+)-2',4',6'-Trimethylphenylcarbamoyl-thiaphysovenol |
| (N-allyl pyrrolidinoindoline carbamate) | 73 | CH$_3$ | (+)-N$^1$-Allylnorphysostigmine |
| | 74 | phenyl | (+)-N$^1$-Allylnorphenserine |
| | 75 | 2'-tolyl | (+)-N$^1$-Allylnortolserine |
| | 76 | 4'-cymyl | (+)-N$^1$-Allylnorcymserine |
| (N-phenethyl pyrrolidinoindoline carbamate) | 77 | CH$_3$ | (+)-N$^1$-Phenethylnorphysostigmine |
| | 78 | phenyl | (+)-N$^1$-Phenethylnorphenserine |
| | 79 | 2'-tolyl | (+)-N$^1$-Phenethylnortolserine |
| | 80 | 4'-cymyl | (+)-N$^1$-Phenethylnorcymserine |
| (3-(1-methylamino-ethyl)-2H-indole carbamate) | 81 | CH$_3$ | (+)-3-(1-Methylamino)-ethyl-2H-indo1-5yl-methylcarbamate |
| | 82 | phenyl | (+)-3-(1-Methylamino)-ethyl-2H-indo1-5yl-phenylcarbamate |
| | 83 | 2'-tolyl | (+)-3-(1-Methylamino)-ethyl-2H-indo1-5yl-tolylcarbamate |
| | 84 | 4'-cymyl | (+)-3-(1-Methylamino)-ethyl-2H-indol-5yl- ymylcarbamate |
| (N-benzyl pyrrolidinoindoline carbamate) | 85 | CH$_3$ | (+)-N$^1$-Benzylnorphysostigmine |
| | 86 | phenyl | (+)-N$^1$-Benzylnorphenserine |
| | 87 | 2'-tolyl | (+)-N$^1$-Benzylnortolserine |
| | 88 | 4'-cymyl | (+)-N$^1$-Benzylnorcymserine |

TABLE 1-continued

| Structure | No. | R | Compounds |
|---|---|---|---|
| 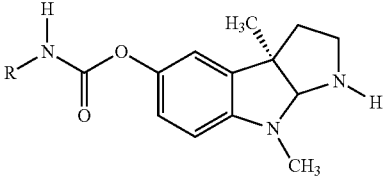 | 89<br>90<br>91<br>92 | CH₃<br>phenyl<br>2'-tolyl<br>4'-cymyl | (+)-N¹-Norphysostigmine<br>(+)- N¹-Norphenserine<br>(+)-N¹-Nortolserine<br>(+)-N¹-Norcymserine |
| 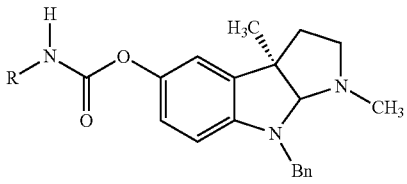 | 93<br>94<br>95<br>96 | CH₃<br>phenyl<br>2'-tolyl<br>4'-cymyl | (+)-N⁸-Benzylnorphysostigmine<br>(+)- N⁸-Benzylnorphenserine<br>(+)-N⁸-Benzylnortolserine<br>(+)-N⁸-Benzylnorcymserine |
| 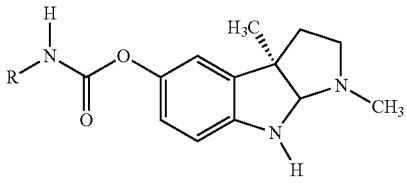 | 97<br>98<br>99<br>100 | CH₃<br>phenyl<br>2'-tolyl<br>4'-cymyl | (+)-N⁸-Norphysostigmine<br>(+)- N⁸-Norphenserine<br>(+)-N⁸-Nortolserine<br>(+)-N⁸-Norcymserine |
| 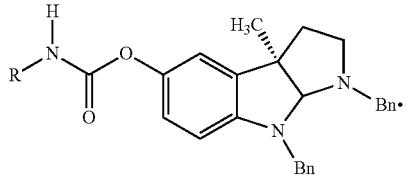 | 101<br>102<br>103<br>104 | CH₃<br>phenyl<br>2'-tolyl<br>4'-cymyl | (+)-N¹,N⁸-Bisbenzylnorphysostigmine<br>(+)- N¹,N⁸-Bisbenzylnorphenserine<br>(+)-N¹,N⁸-Bisbenzylnortalserine<br>(+)-N¹,N⁸-Bisbenzylnorcyraserine |
| 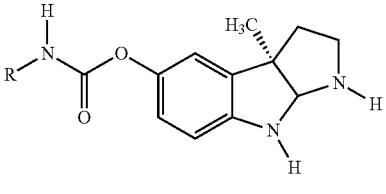 | 105<br>106<br>107<br>108 | CH₃<br>phenyl<br>2'-tolyl<br>4'-cymyl | (+)-N¹,N⁸-Bisnorphysosigmine<br>(+)-N¹,N⁸-Bisnorphenserine<br>(+)-N¹,N⁸-Bisnortolserine<br>(+)-N¹,N⁸-Bisnorcymserine |
| 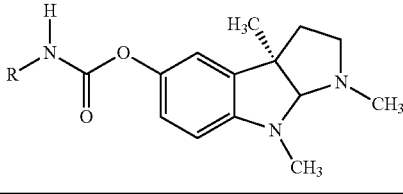 | 109<br>110<br>111<br>112 | CH₃<br>phenyl<br>2'-tolyl<br>4'-cymyl | (+)-3a-Phenylphysosigmine<br>(+)- 3a-Phenylphenserine<br>(+)-3a-Phenyltolserine<br>(+)-3a-Phenylcymserine |

The invention, in one aspect, a compound having the formula XIV or XV:

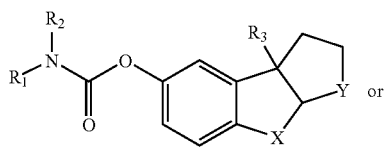

(XIV)

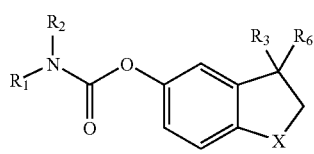

(XV)

wherein $R_1$ and $R_2$ are, independently, hydrogen, branched or straight chain $C_1$-$C_8$ alkyl, substituted or unsubstituted aryl, or aralkyl;

$R_3$ is branched or straight chain $C_1$-$C_4$ alkyl or heteroalkyl or $C_4$-$C_8$ alkyl or heteroalkyl, or substituted or unsubstituted aryl;

X and Y are, independently, O, S, alkyl, hydrocarbon moiety, C(H)$R_4$, or N$R_5$, wherein $R_4$ and $R_5$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl; and $R_6$ is hydrogen; $C_1$-$C_8$ alkyl, $C_2$-$C_8$ alkenyl, $C_2$-$C_8$ alkynyl, aralkyl, or substituted or unsubstituted aryl, or (CH$_2$)$_n$ $R_7$, where $R_7$ is hydroxy, alkoxy, cyano, ester, carboxylic acid, substituted or unsubstituted amino, and n is from 1 to 4, wherein the compound having the formula XIV or XV is a racemic mixture or the substantially pure (−)-enantiomer.

In one embodiment, the compounds having the structure XIV and XV have an enantiomeric purity for the (−)-enantiomer of from 55 to 100%, desirably from 75 to 100%, more desirably from 85 to 100%, more desirably from 95 to 100%, and even more desirably 100%.

In another embodiment, when the compound has the structure XIV or XV, Y is C(H)$R_4$ or X is O, S, or C(H)$R_4$.

Figure 13A:
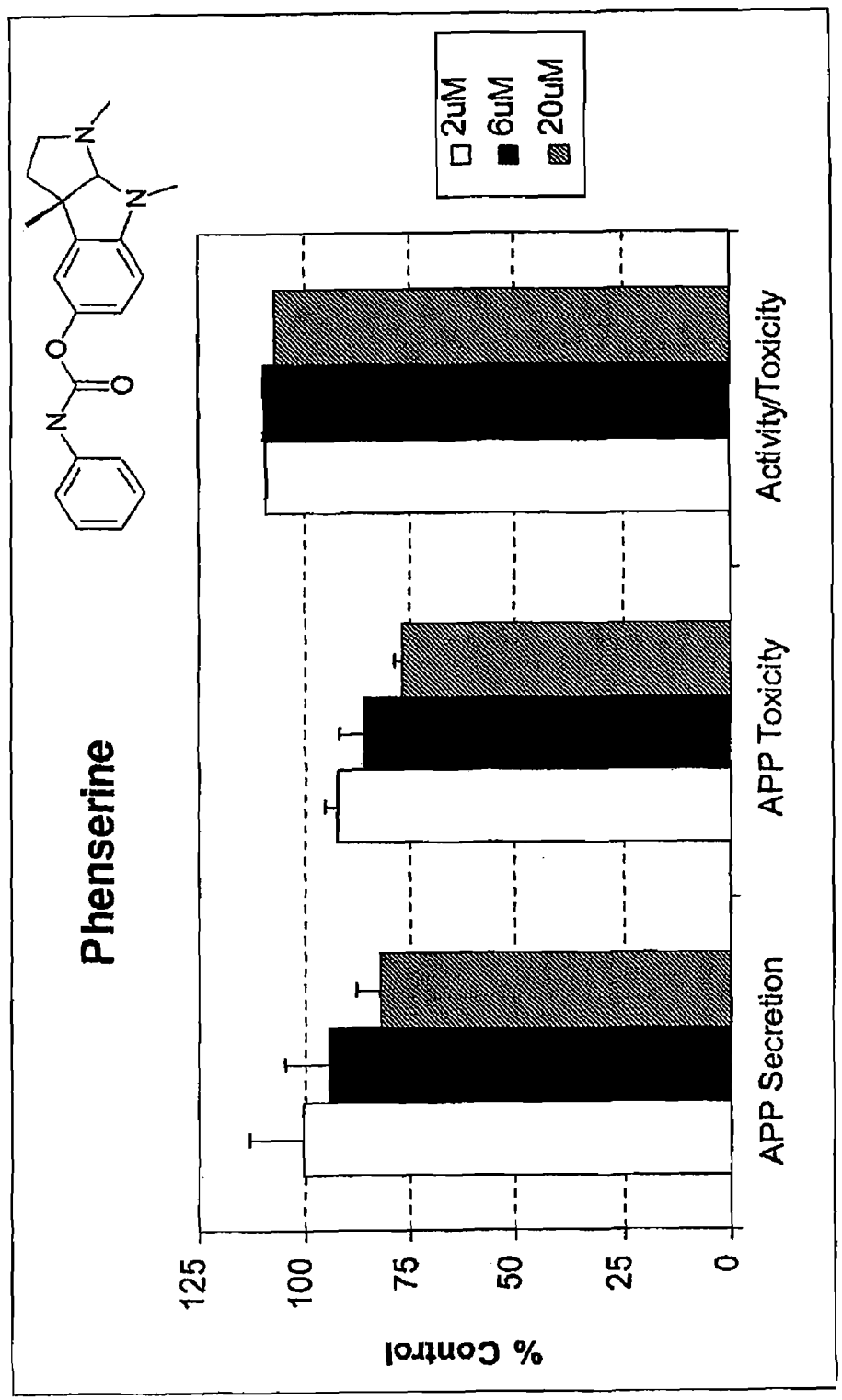
FIG. 13A shows the effects of (−)-phenserine on secreted APP levels and cell-viability in SH-SY5Y cells.
Figure 13B:
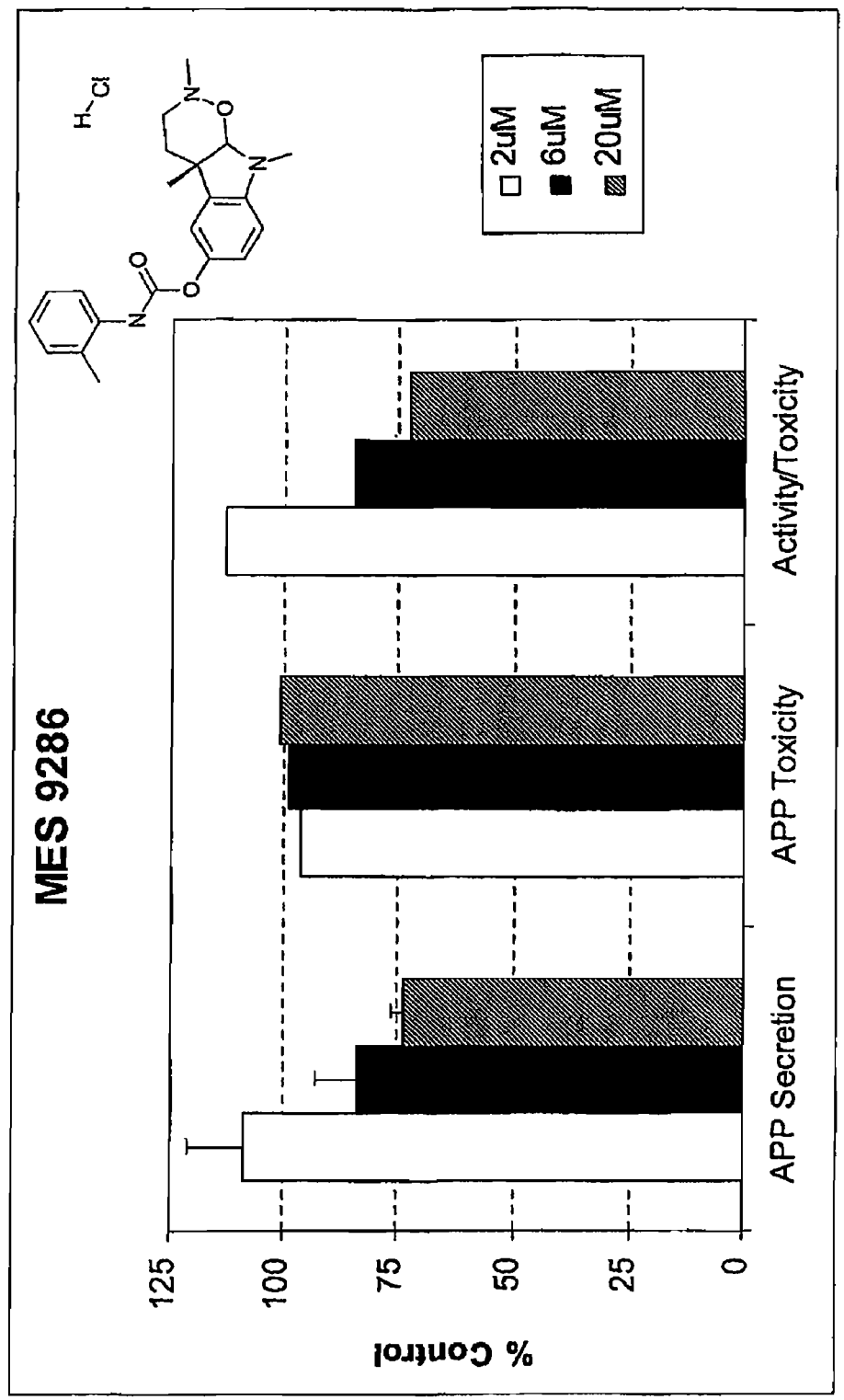
Figure 13D:
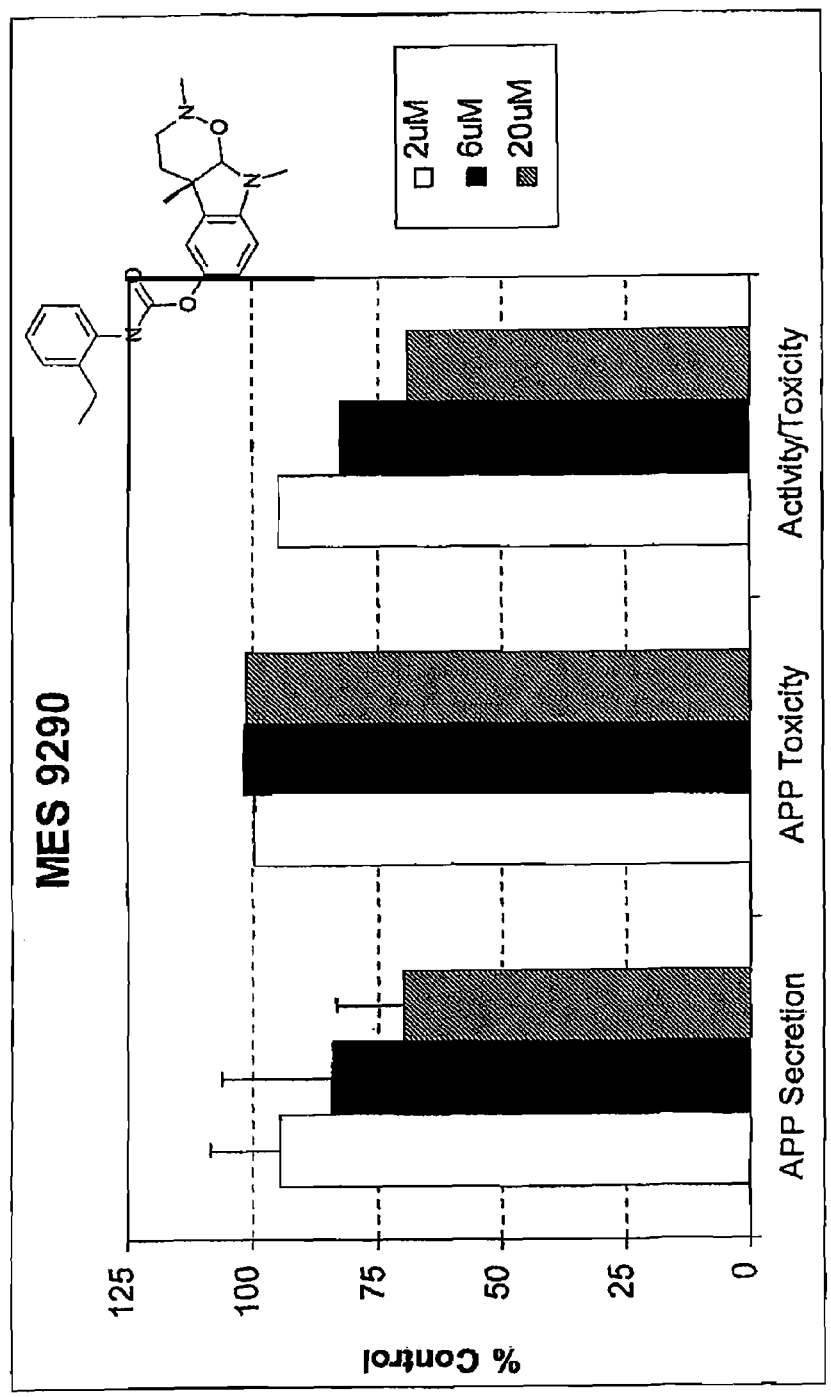

In yet another embodiment, the compound of formula XIV is MES9280 (FIG. 13K), MES9232 (FIG. 13J), MES9313 (FIG. 13F), or a (+)-isomer or a racemic mixture thereof.

Figure 13E:
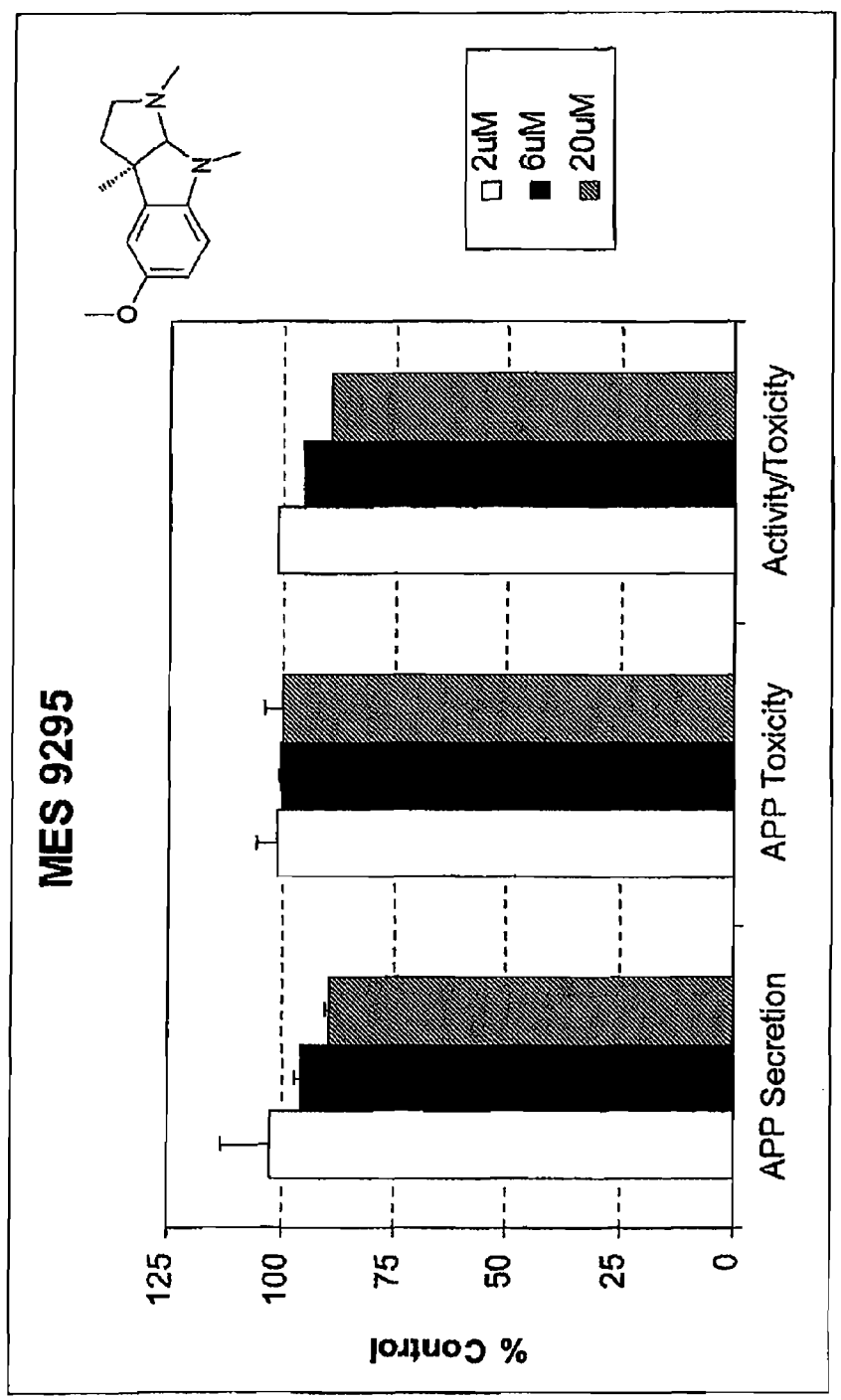
Figure 13F:
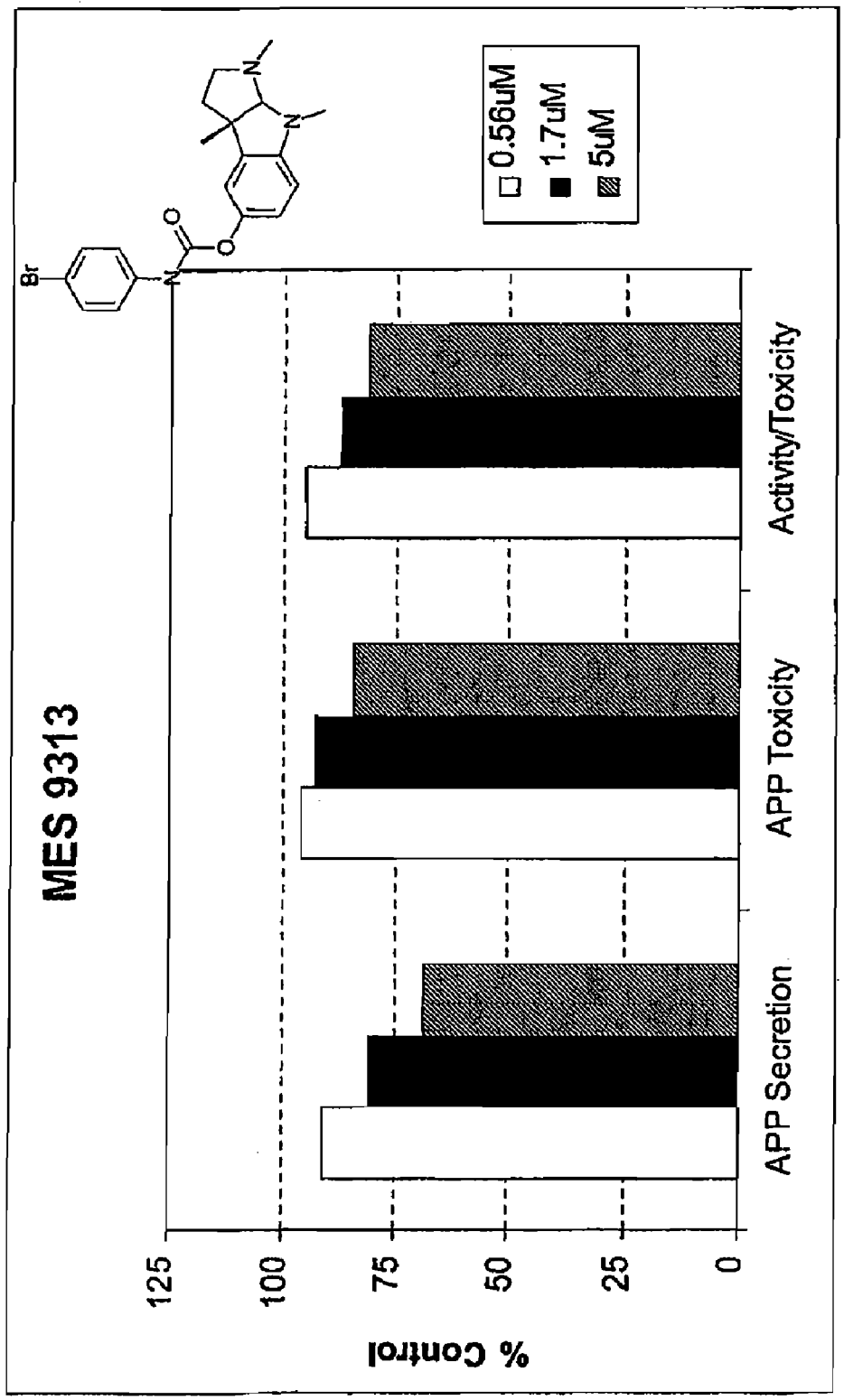
Figure 13G:
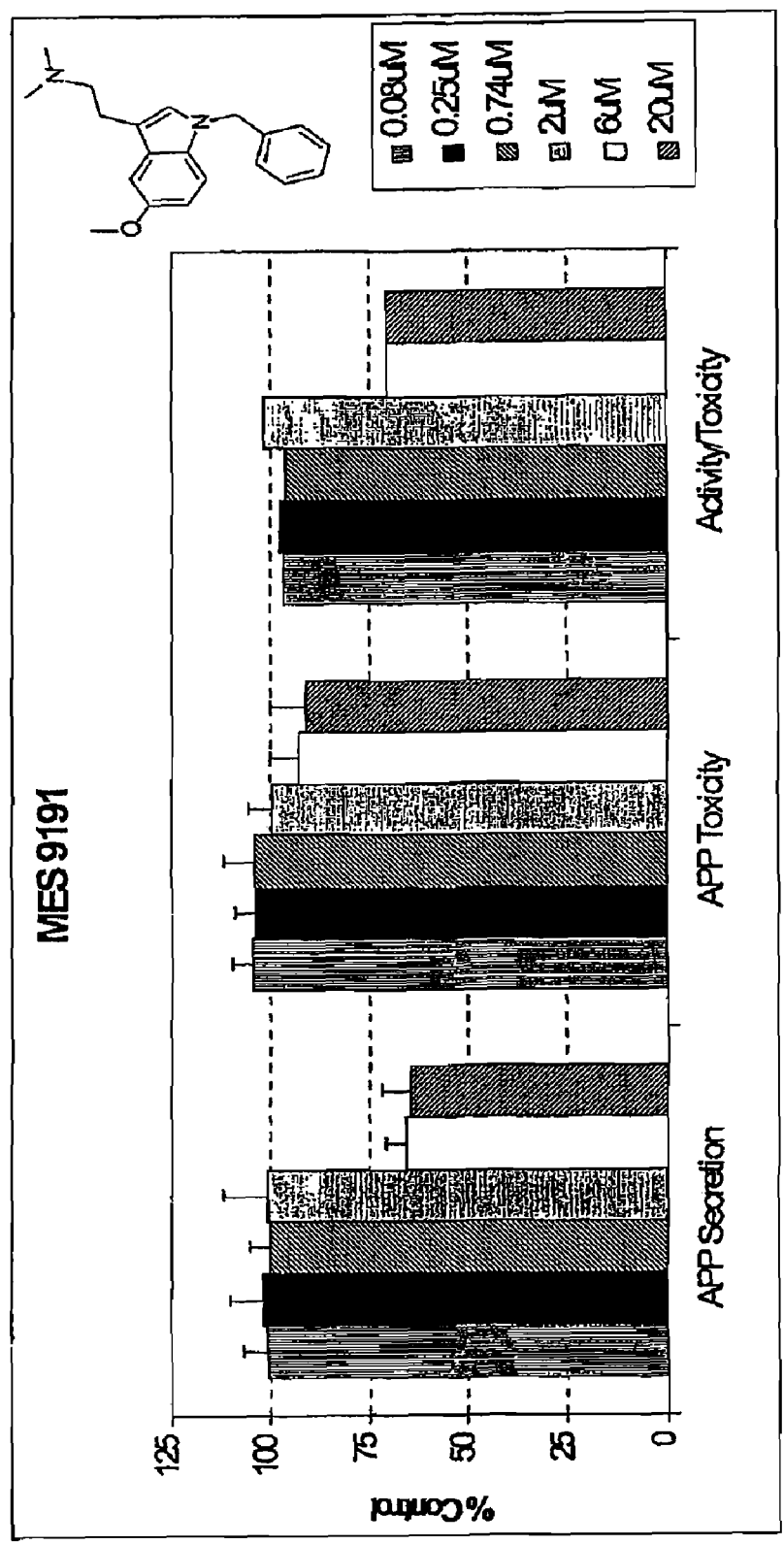
Figure 13H:
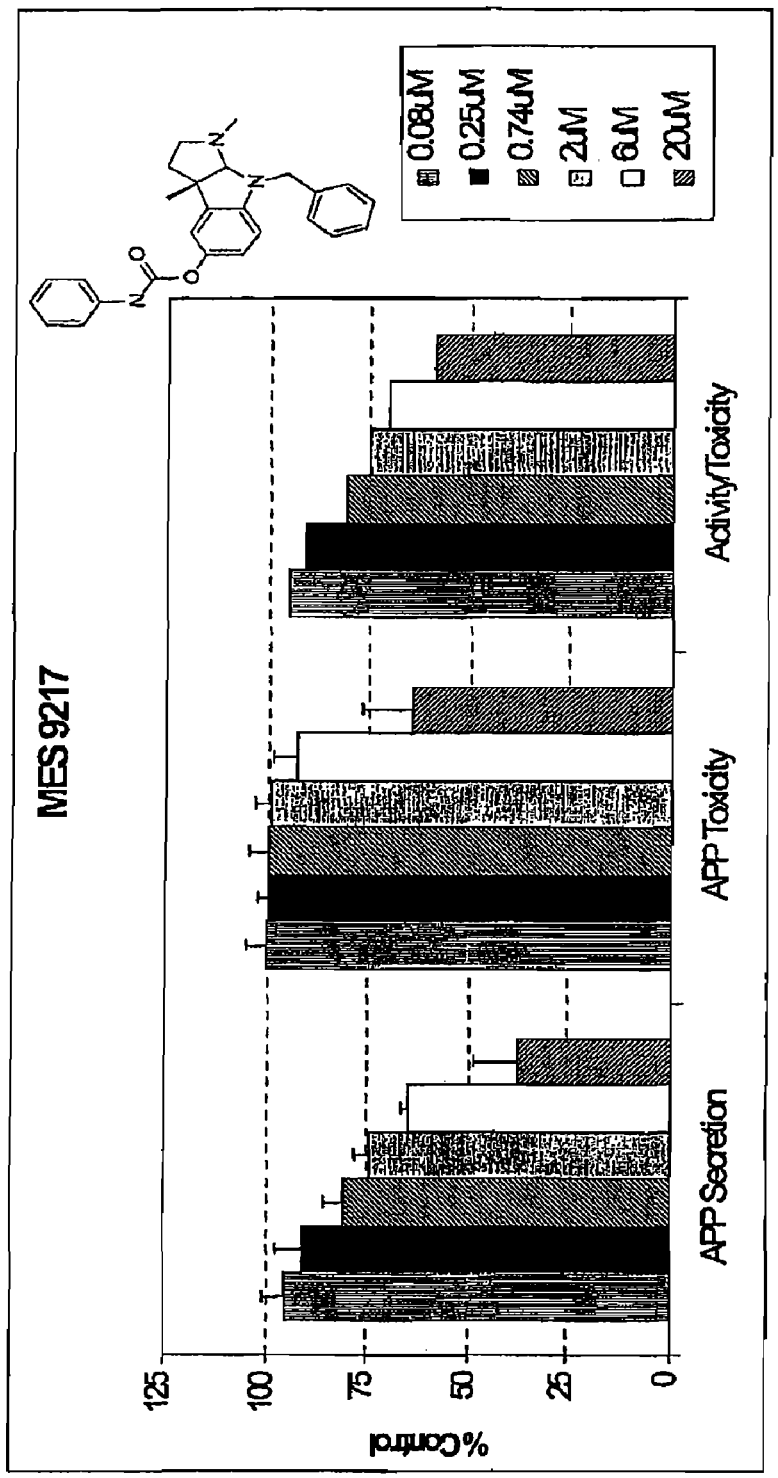
Figure 13I:
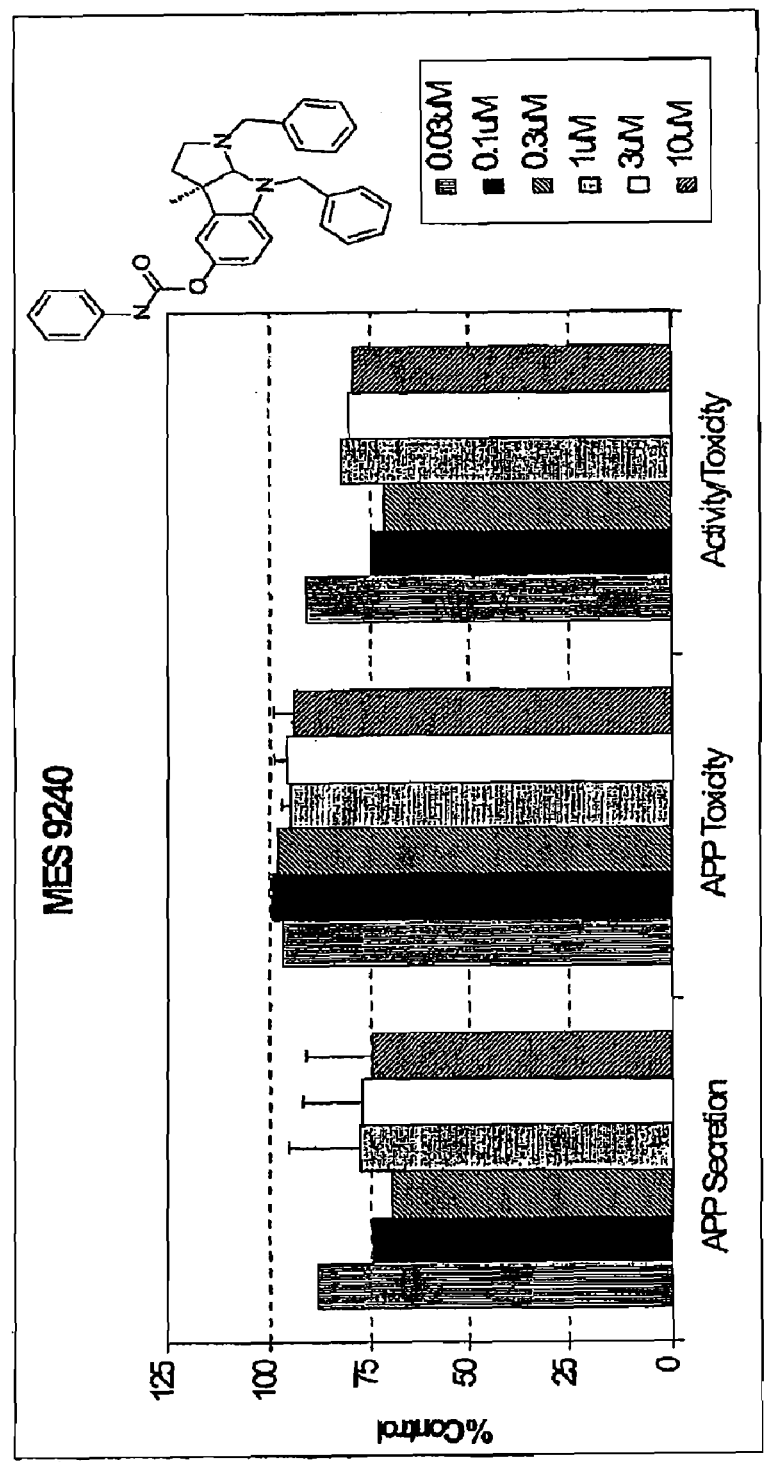
Figure 13J:
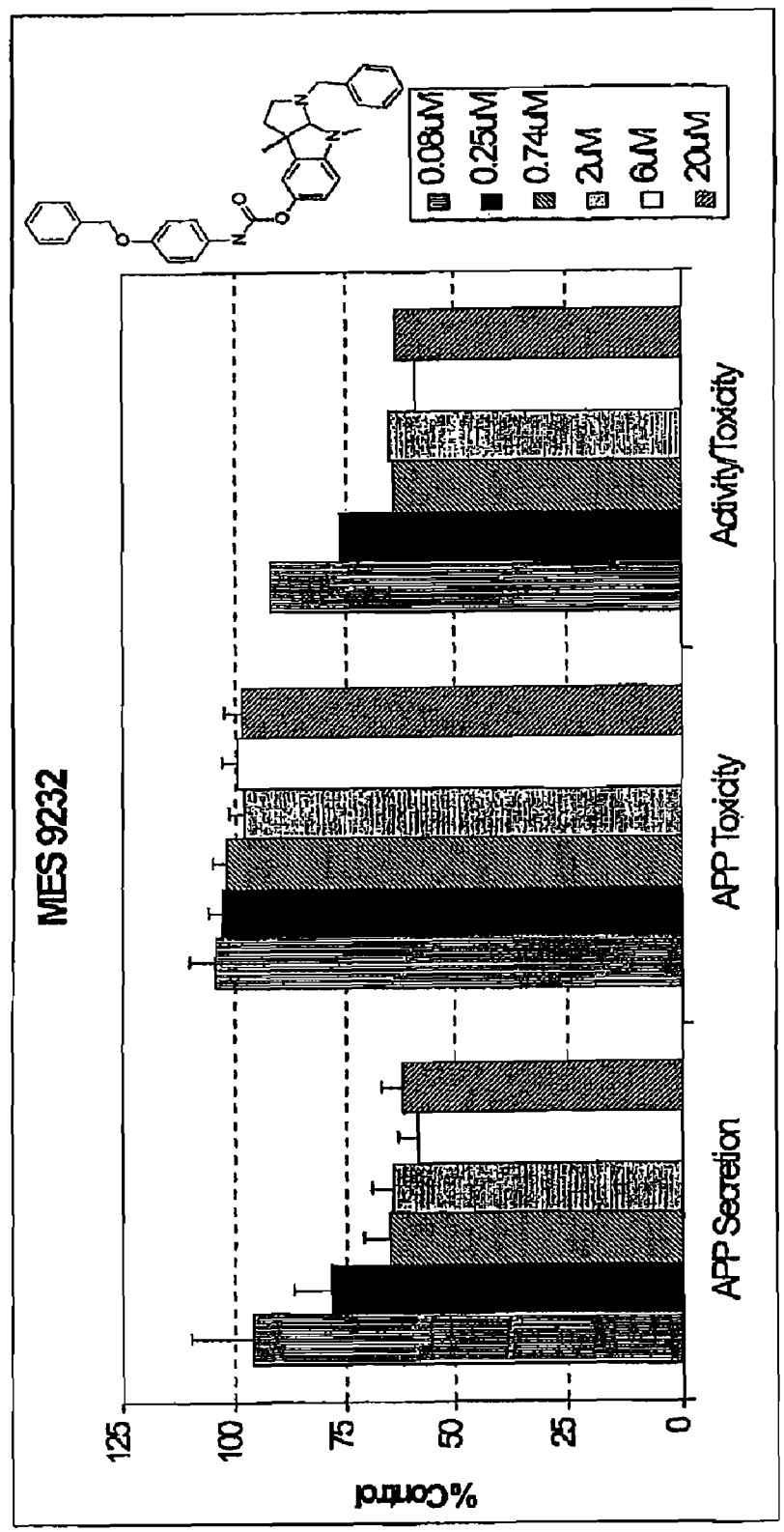
Figure 13K:
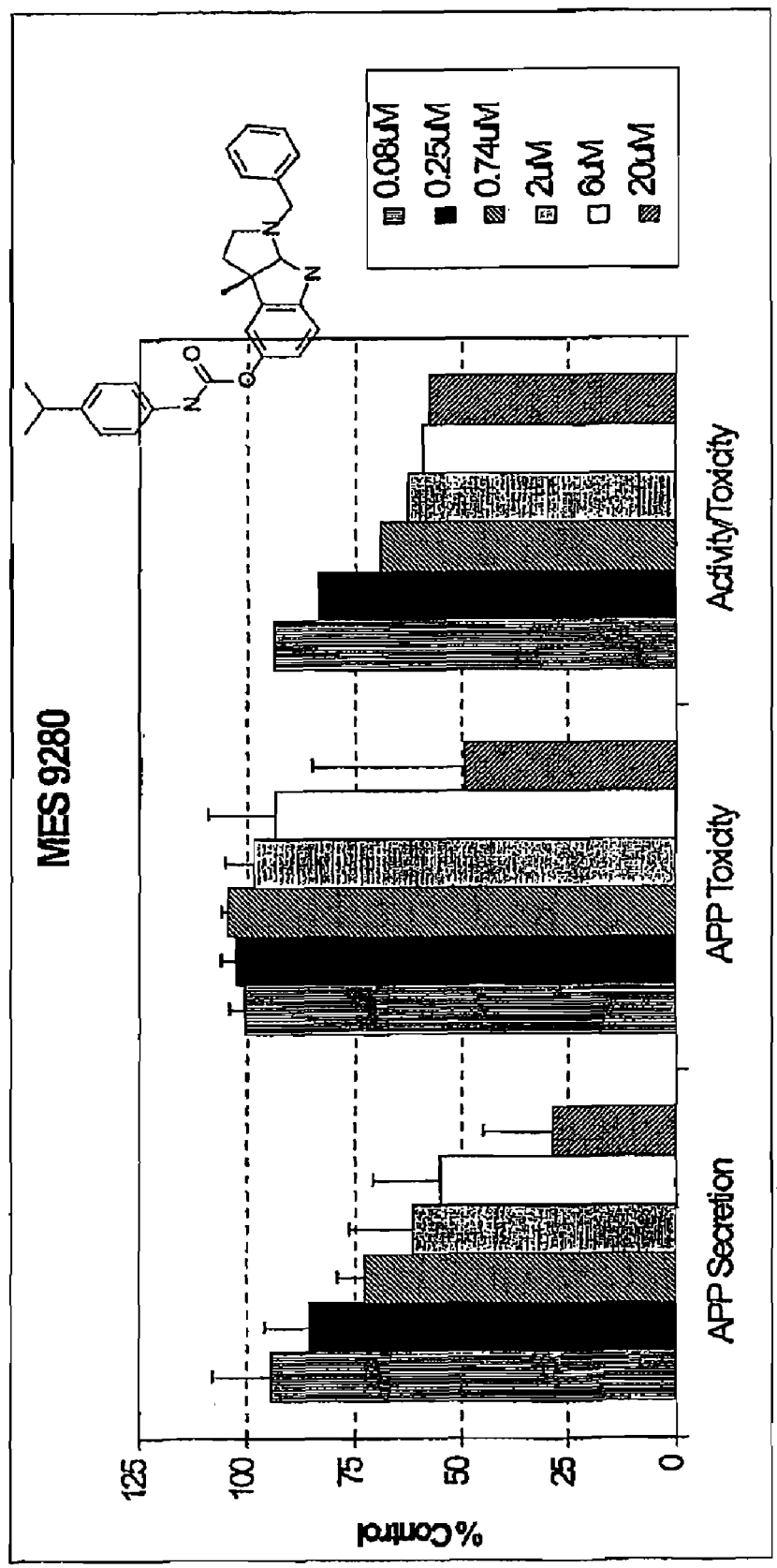
Figure 13L:
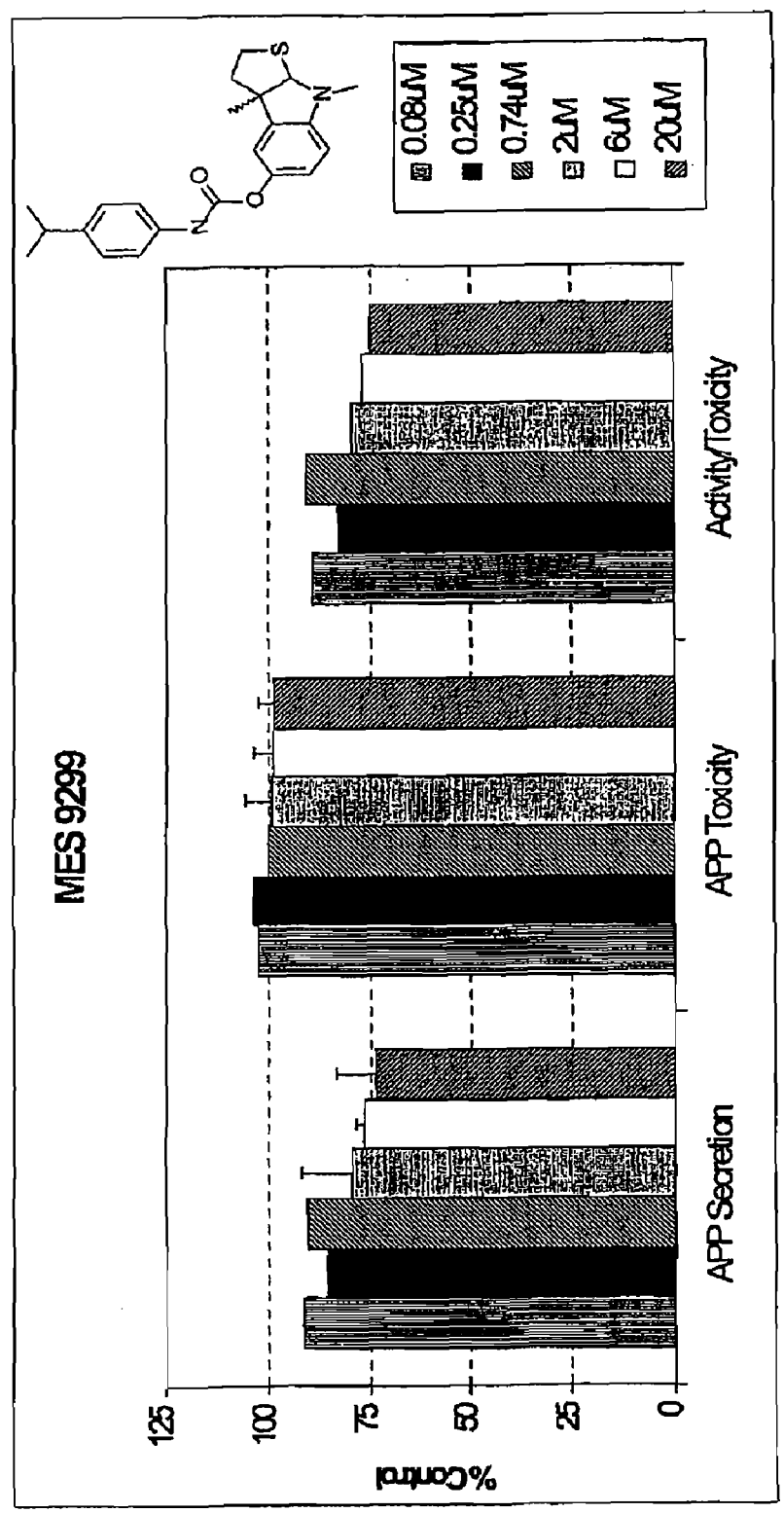
Figure 13M:
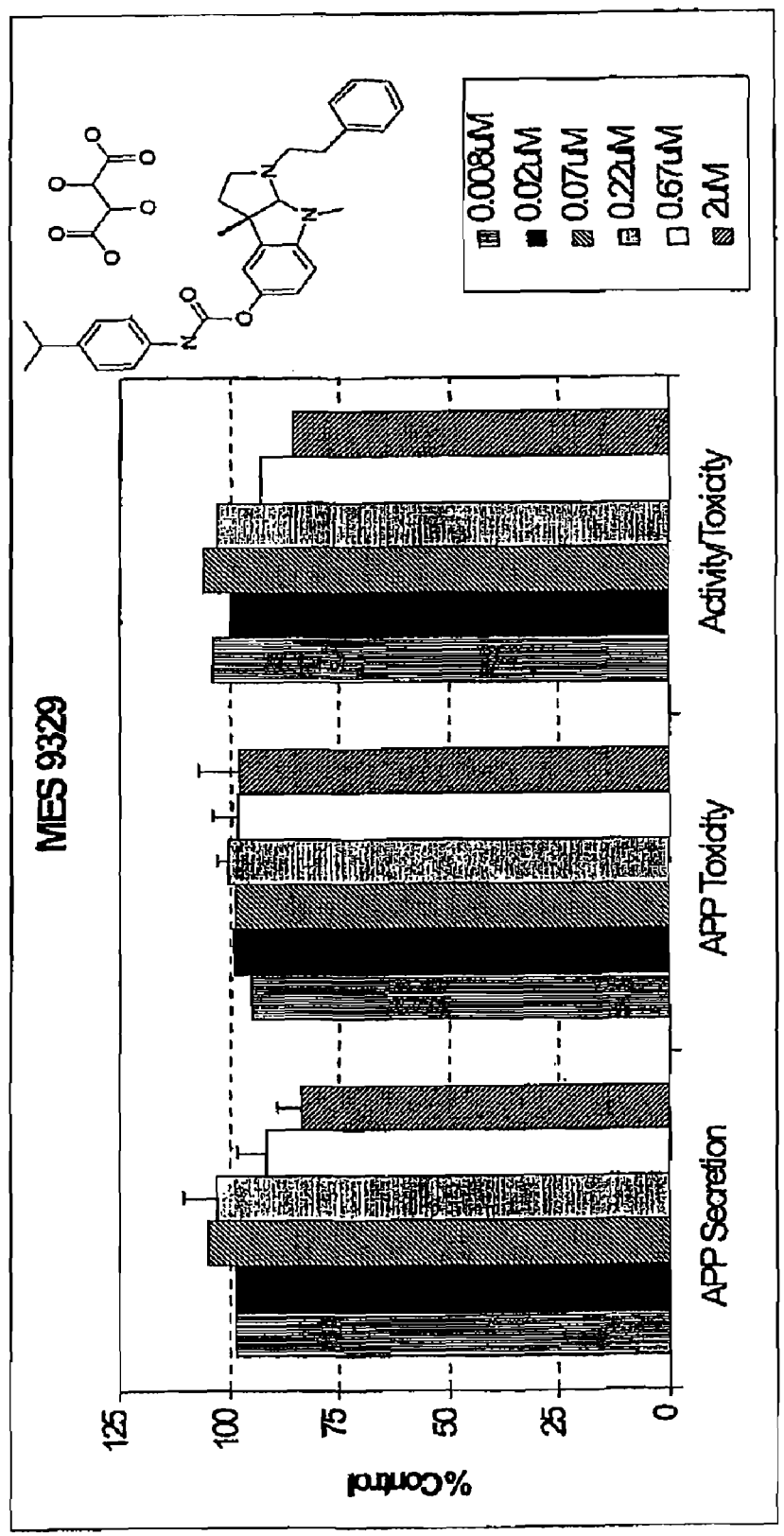

In another embodiment, when the compound has the formula XIV, where X and Y are nitrogen, and the compound is the substantially pure (−)-enantiomer, then $R_3$ is not methyl. In another embodiment, when the compound has the formula XIV, where X is nitrogen, Y is nitrogen or oxygen, and the compound is the substantially pure (−)-enantiomer, then $R_5$ is not hydrogen or $C_1$-$C_{10}$ alkyl. In another embodiment, when the compound has the formula XIV, where X is nitrogen and Y is sulfur, and the compound is the substantially pure (−)-enantiomer, then $R_3$ is not methyl. In another embodiment, the compound is not (−)-phenserine, (−)-physostigmine, (−)-heptyl-physostigmine, (−)-physovenine, (−)-N(1)-norphysostigmine, MES9217 (FIG. 13H), MES9299 (FIG. 13L), and MES9329 (FIG. 13M). In one embodiment, when the compound is formula XIV or XV, $R_3$ is not methyl. In particular embodiments, $R_3$ is a branched or straight chain alkyl or heteroalkyl group of 2, 3, 4, 5, 6, 7, or 8 carbons or substituted or unsubstituted aryl.

Figure 2:
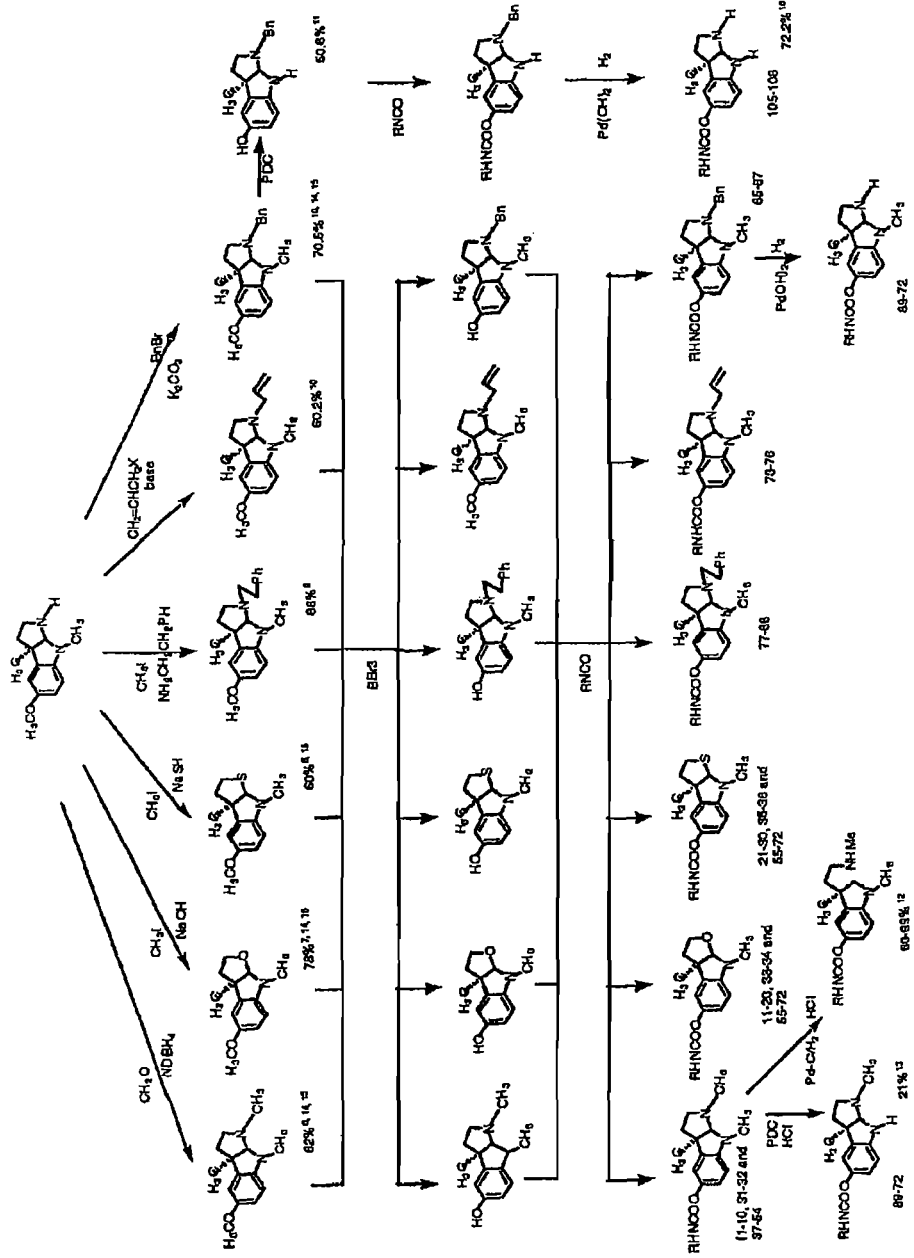
FIG. 2 shows the transformation of (+)-oxindole to analogues of (+)-physostigmine. Compound numbers refer to compounds in Table 1.

FIGS. 1 and 2 show one approach to the synthesis of compounds having the structure I and II. Using techniques known in the art (see Julian et al., *J. Am. Chem. Soc.*, 1935, 57, 563; Lee et al., *J. Org. Chem.*, 1991, 56, 872; Pei et al., *Heterocycles*, 1995, 41, 2823; Lee et al., *J. Chromatography*, 1990, 523, 317; and Pei et al., *Heterocycles*, 1994, 39, 557, which are incorporated by reference in their entirety), the physostigmine compound A (FIG. 1) can be prepared in high yield and enantiopurity. Compound A is an important intermediate, and can be used to produce a variety of compounds having the structure I and II. FIG. 2 shows that by using techniques lmown in the art (see Yu et al., *Heterocycles*, 1988, 27, 745; Yu et al., *Helv. Chem. Res.*, 1991, 74,761; He et al., *Med. Chem. Res.* 1992, 2, 229; Pei et al., *Med. Chem. Res.*, 1995, 5, 455; Yu et al., *J. Med. Chem.*, 1998, 31, 2297; Zhu, *Tet. Lett.*, 2000, 41, 4861; Pei et al., *Med. Chem. Res.*, 1995, 5, 455; and Yu et al., *J. Med. Chem.*, 1997, 40, 2895, which are incorporated by reference in their entirety) compound A can be converted to a number of different compounds having the structure I and II. The numbers below each compound in FIG. 2 correspond to the compound numbers in Table 1. The racemic mixture of I and II as well as compounds XIV and XV can be prepared using the synthetic procedure outlined in FIGS. 1 and 2, where a chiral chromatography step is not performed to produce the racemic mixture or the (−)-enantiomer is isolated instead of the (+)-enantiomer.

The invention also relates to a compound having the formula V, VI, or VII

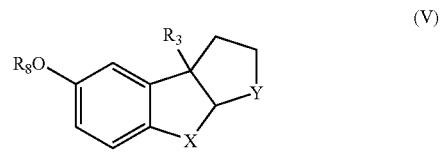

(V)

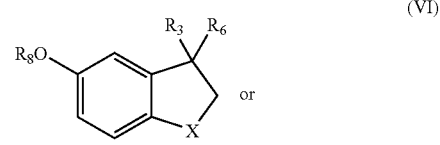

(VI)

or

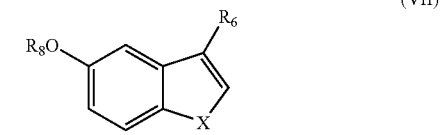

(VII)

wherein $R_8$ is hydrogen, branched or straight chain $C_1$-$C_8$ alkyl, substituted or unsubstituted aryl, aralkyl, or C$R_9R_{10}$O$R_{11}$, where $R_9$ and $R_{10}$ are, independently, hydrogen or alkyl, and $R_{ii}$, is alkyl;

$R_3$ is branched or straight chain $C_1$-$C_4$ alkyl, or substituted or unsubstituted aryl;

X and Y are, independently, O, S, C(H)$R_4$, or N$R_5$, wherein $R_4$ and $R_5$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl; and $R_6$ is hydrogen; $C_1$-$C_8$ alkyl, $C_2$-$C_8$ alkenyl, $C_2$-$C_8$ alkynyl, aralkyl, or substituted or unsubstituted aryl, or (CH$_2$)$_n$ $R_7$, where $R_7$ is hydroxy, alkoxy, cyano, ester, carboxylic acid, substituted or unsubstituted amino, and n is from 1 to 4, with the proviso that when the compound is formula V, X is NCH$_3$, and Y is N$R_5$, where $R_5$ is hydrogen, loweralkyl, arylloweralkyl, heteroarylloweralkyl, cycloalkylmethyl, or loweralkenyl methyl, $R_3$ is not methyl or $R_8$ is not H or loweralkyl.

The compounds having the formula V-VII as well as compounds described below are referred to herein as "non-carbamate compounds" because they do not possess the carbamate group present in compounds I-IV, XIV-XVI. Compounds V-XIII are generally the synthetic precursors to compounds I-IV. FIG. 1 provides a general synthesis to intermediate A, which is a species of compound V. Intermediate A is shown as the (+)-enantiomer; however, the (−)-enantiomer can also be isolated using chiral chromatography. Similarly, the (+)- and (−)-enantiomers of compound VI can also be produced using similar methodology. Furthermore, in the absence of the chiral chromatography step in FIG. 1, the racemic compounds V and VI can be produced.

In another embodiment, when the non-carbamate compound has the formula VII, where X is N$R_5$, the reaction depicted in Scheme 1 can be used to produce the compounds. For example, in Scheme I, compound B (compound VII where X is NH) can be treated with a base, such as NaNH$_2$, then treated with an alkyl or aralkyl halide compound to produce compound C.

SCHEME 1

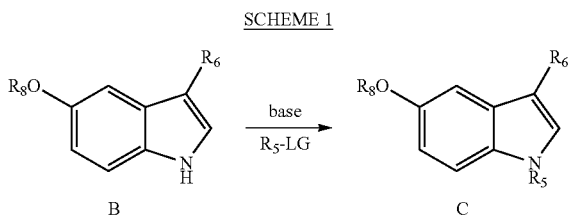

In one embodiment, when the compound is formula V, X and Y are $NR_5$, wherein $R_5$ is branched or straight chain $C_1$-$C_8$ alkyl, desirably methyl. In another embodiment, when the compound is formula V, $R_3$ is methyl, X and Y are $NCH_3$, and $R_8$ is $C_1$-$C_8$ straight chain alkyl, desirably methyl.

In another embodiment, when the compound is formula VII, X is $NR_5$, wherein $R_5$ is branched or straight chain $C_1$-$C_8$ alkyl or aralkyl, desirably benzyl. In another embodiment, when the compound is formula VII, $R_6$ is $(CH_2)_n R_7$, where $R_7$ is a substituted or unsubstituted amino group. In another embodiment, when the compound is formula VII, X is $NR_5$, where $R_5$ is benzyl, $R_6$ is $(CH_2)_2 N(CH_3)_2$ and $R_8$ is methyl.

The invention also relates to a compound having the formula VIII:

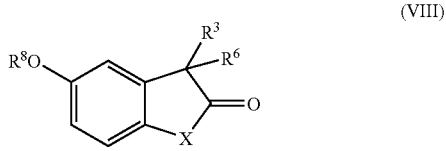

(VIII)

wherein $R^8$ is hydrogen, branched or straight chain. $C_1$-$C_8$ alkyl, substituted or unsubstituted aryl, aralkyl, or $CR_9 R_{10} OR_{11}$, where $R_9$ and $R_{10}$ are, independently, hydrogen or alkyl, and $R_{11}$ is alkyl;

$R^3$ is branched or straight chain $C_1$-$C_4$ alkyl, or substituted or unsubstituted aryl;

X is O, S, $C(H)R_4$, or $NR_5$, wherein $R_4$ and $R_5$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl; and $R^6$ is hydrogen; $C_1$-$C_8$ alkyl, $C_2$-$C_8$ alkenyl, $C_2$-$C_8$ alkynyl, aralkyl, or substituted or unsubstituted aryl, or $(CH_2)_n R_7$, where $R_7$ is hydroxy, alkoxy, cyano, ester, carboxylic acid, substituted or unsubstituted amino, and n is from 1 to 4.

The invention further relates to a compound having the formula IX

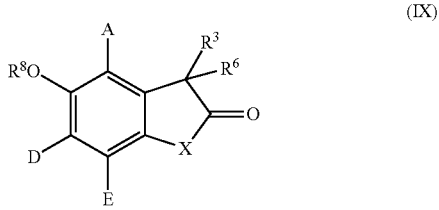

(IX)

wherein $R^8$ is hydrogen, branched or straight chain $C_1$-$C_8$ alkyl, substituted or unsubstituted aryl, aralkyl, or $CR_9 R_{10} OR_{11}$, where $R_9$ and $R_{10}$ are, independently, hydrogen or alkyl, and $R_{11}$ is alkyl;

$R^3$ is branched or straight chain $C_1$-$C_4$ alkyl, or substituted or unsubstituted aryl;

$R^6$ is hydrogen; $C_1$-$C_8$ alkyl, $C_2$-$C_8$ alkenyl, $C_2$-$C_8$ alkynyl, aralkyl, or substituted or unsubstituted aryl, or $(CH_2)_n R_7$, where $R_7$ is hydroxy, alkoxy, cyano, ester, carboxylic acid, substituted or unsubstituted amino, and n is from 1 to 4;

X is O, S, $C(H)R_4$, or $NR_5$, wherein $R_4$ and $R_5$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl; and A, D, and E are, independently, hydrogen, hydroxy, alkoxy, halide, alkyl, aralkyl, or amino.

The invention also relates to a compound having the formula X

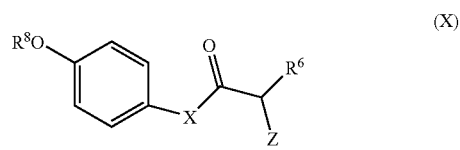

(X)

wherein $R^8$ is hydrogen, branched or straight chain $C_1$-$C_8$ alkyl, substituted or unsubstituted aryl, aralkyl, or $CR_9 R_{10} OR_{11}$, where $R_9$ and $R_{10}$ are, independently, hydrogen or alkyl, and $R_{11}$ is alkyl;

$R^6$ is hydrogen; $C_1$-$C_8$ alkyl, $C_2$-$C_8$ alkenyl, $C_2$-$C_8$ alkynyl, aralkyl, or substituted or unsubstituted aryl, or $(CH_2)_n R_7$, where $R_7$ is hydroxy, alkoxy, cyano, ester, carboxylic acid, substituted or unsubstituted amino, and n is from 1 to 4;

X is O, S, $C(H)R_4$, or $NR_5$, wherein $R_4$ and $R_5$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl; and Z is halide, hydroxy, or alkoxy.

The invention also relates to a compound having the formula XI

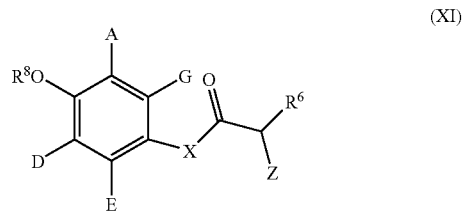

(XI)

wherein $R^8$ is hydrogen, branched or straight chain $C_1$-$C_8$ alkyl, substituted or unsubstituted aryl, aralkyl, or $CR_9 R_{10} OR_{11}$, where $R_9$ and $R_{10}$ are, independently, hydrogen or alkyl, and $R_{11}$ is alkyl;

$R^6$ is hydrogen; $C_1$-$C_8$ alkyl, $C_2$-$C_8$ alkenyl, $C_2$-$C_8$ alkynyl, aralkyl, or substituted or unsubstituted aryl, or $(CH_2)_n R_7$, where $R_7$ is hydroxy, alkoxy, cyano, ester, carboxylic acid, substituted or unsubstituted amino, and n is from 1 to 4;

X is O, S, $C(H)R_4$, or $NR_5$, wherein $R_4$ and $R_5$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl;

A, D, E, and G are, independently, hydrogen, hydroxy, alkoxy, halide, alkyl, aralkyl, or amino; and Z is halide, hydroxy, or alkoxy.

In one embodiment, steps 3-5 in FIG. 1 can be used to prepare compounds having the formula VIII-XI.

The invention further relates to a compound having the formula XII:

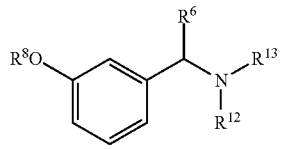

(XII)

wherein $R^8$ is hydrogen, branched or straight chain $C_1$-$C_8$ alkyl, substituted or unsubstituted aryl, aralkyl, or $CR_9R_{10}OR_{11}$, where $R_9$ and $R_{10}$ are, independently, hydrogen or alkyl, and $R_{11}$ is alkyl;

$R^6$ is hydrogen; $C_1$-$C_8$ alkyl, $C_2$-$C_8$ alkenyl, $C_2$-$C_8$ alkynyl, aralkyl, or substituted or unsubstituted aryl, or $(CH_2)_nR_7$, where $R_7$ is hydroxy, alkoxy, cyano, ester, carboxylic acid, substituted or unsubstituted amino, and n is from 1 to 4; and $R^{12}$ and $R^{13}$ are, independently, hydrogen; $C_1$-$C_8$ alkyl; aryl or substituted aryl; aralkyl; or $(CH_2)_nR^{14}$, wherein $R^{14}$ is hydroxy, alkoxy, ester, carboxylic acid, substituted or unsubstituted amino, and n is from 1 to 4.

The invention also relates to compound having the formula XIII:

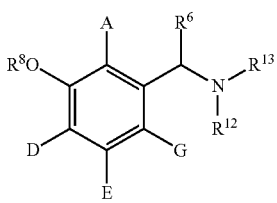

(XIII)

wherein $R^8$ is hydrogen, branched or straight chain $C_1$-$C_8$ alkyl, substituted or unsubstituted aryl, aralkyl, or $CR_9R_{10}OR_{11}$, where $R_9$ and $R_{10}$ are, independently, hydrogen or alkyl, and $R_{11}$ is alkyl;

$R^6$ is hydrogen; $C_1$-$C_8$ alkyl, $C_2$-$C_8$ alkenyl, $C_2$-$C_8$ alkynyl, aralkyl, or substituted or unsubstituted aryl, or $(CH_2)_nR_7$, where $R_7$ is hydroxy, alkoxy, cyano, ester, carboxylic acid, substituted or unsubstituted amino, and n is from 1 to 4; and $R^{12}$ and $R^{13}$ are, independently, hydrogen; $C_1$-$C_8$ alkyl; aryl or substituted aryl; aralkyl; or $(CH_2)_nR^{14}$, wherein $R^{14}$ is hydroxy, alkoxy, ester, carboxylic acid, substituted or unsubstituted amino, and n is from 1 to 4; and A, D, E, and G are, independently, hydrogen, hydroxy, alkoxy, halide, alkyl, aralkyl, or amino.

In one embodiment, compounds having the formula XII and XIII can be prepared by the general reaction shown in Scheme 2.

SCHEME 2

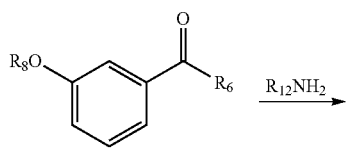

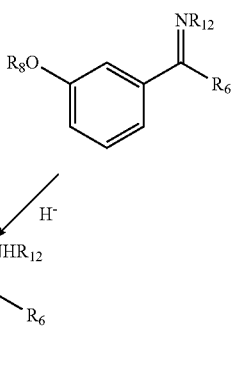

The invention also relates to a compound having the formula XVI

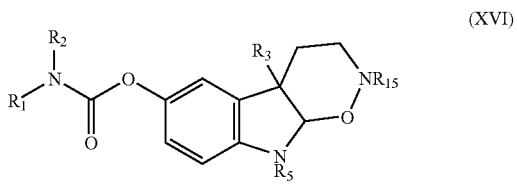

(XVI)

wherein $R_1$ and $R_2$ are, independently, hydrogen, branched or straight chain $C_1$-$C_8$ alkyl, substituted or unsubstituted aryl, or aralkyl;

$R_3$ is branched or straight chain $C_1$-$C_4$ alkyl, or substituted or unsubstituted aryl;

$R_5$ and $R_{15}$ are, independently, hydrogen, oxygen, branched or straight chain $C_1$-$C_8$ alkyl, $C_2$-$C_8$ alkenyl, or $C_2$-$C_8$ alkynyl, aralkyl, or substituted or unsubstituted aryl; and wherein the compound is a racemic mixture, the substantially pure (−)-enantiomer, or the substantially pure (+)-enantiomer.

In a related aspect, the invention features the compound disclosed in FIG. 13C (MES9287) and MES9286 (Table 2). Additional non-carbamate compounds of the present invention are shown in Table 2.

TABLE 2

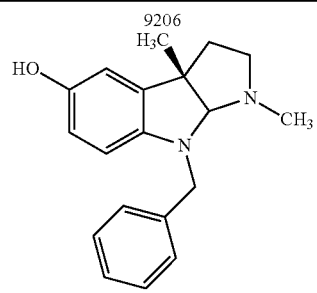

9206

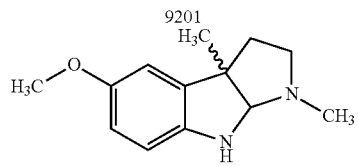

9201

TABLE 2-continued
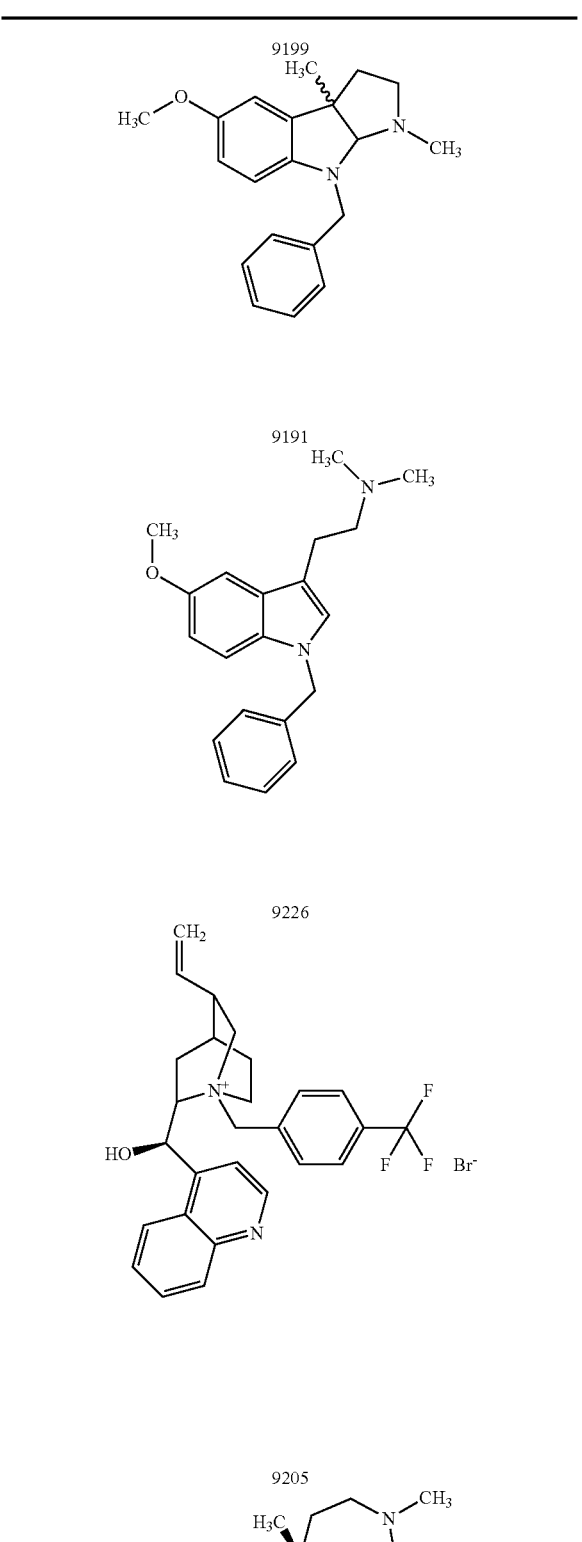
TABLE 2-continued
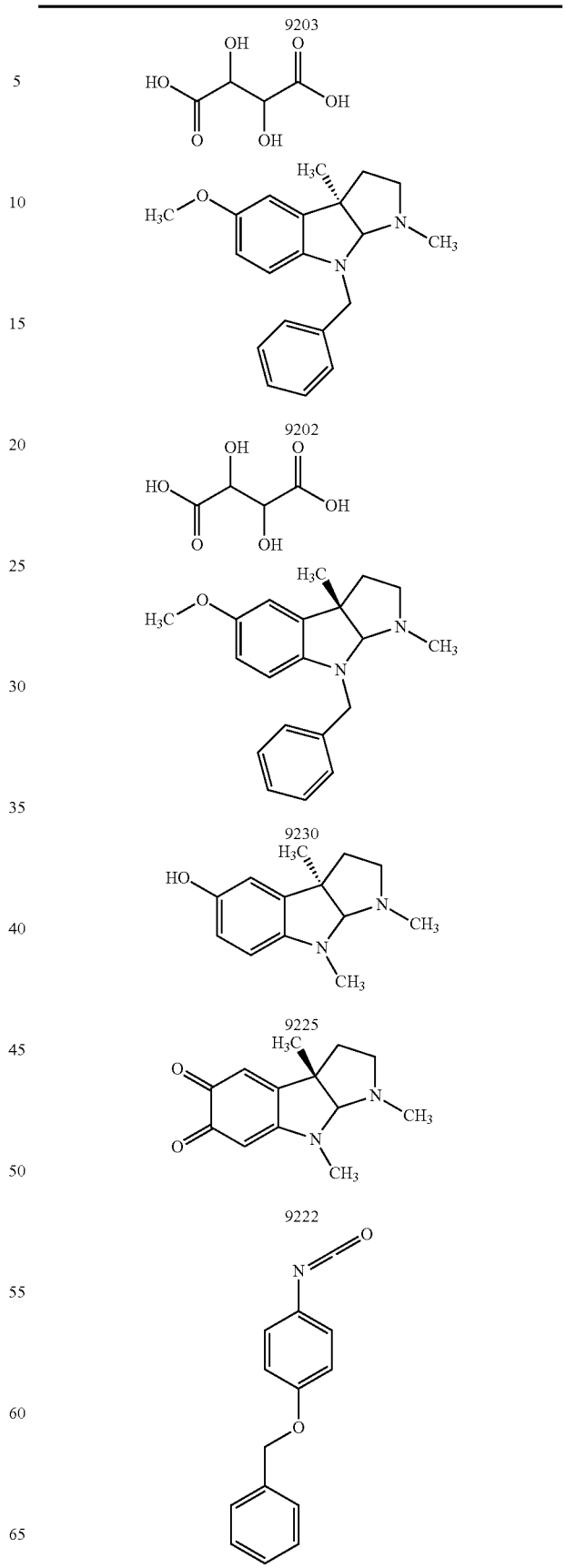

TABLE 2-continued
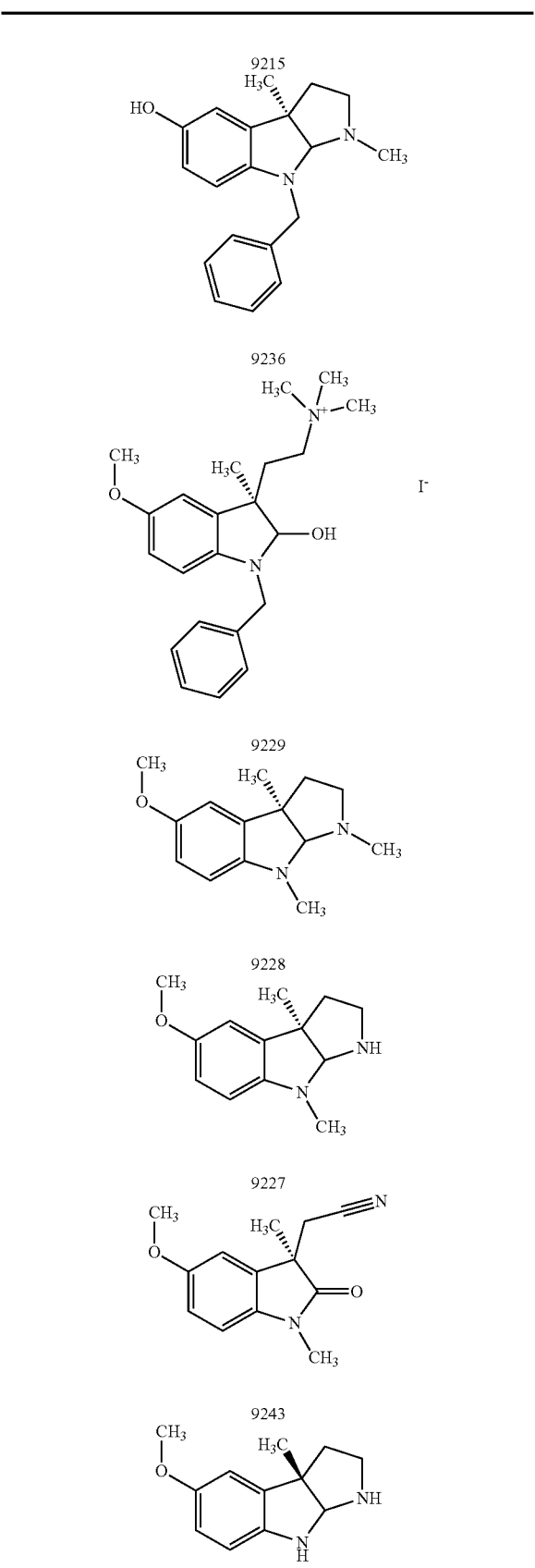
TABLE 2-continued
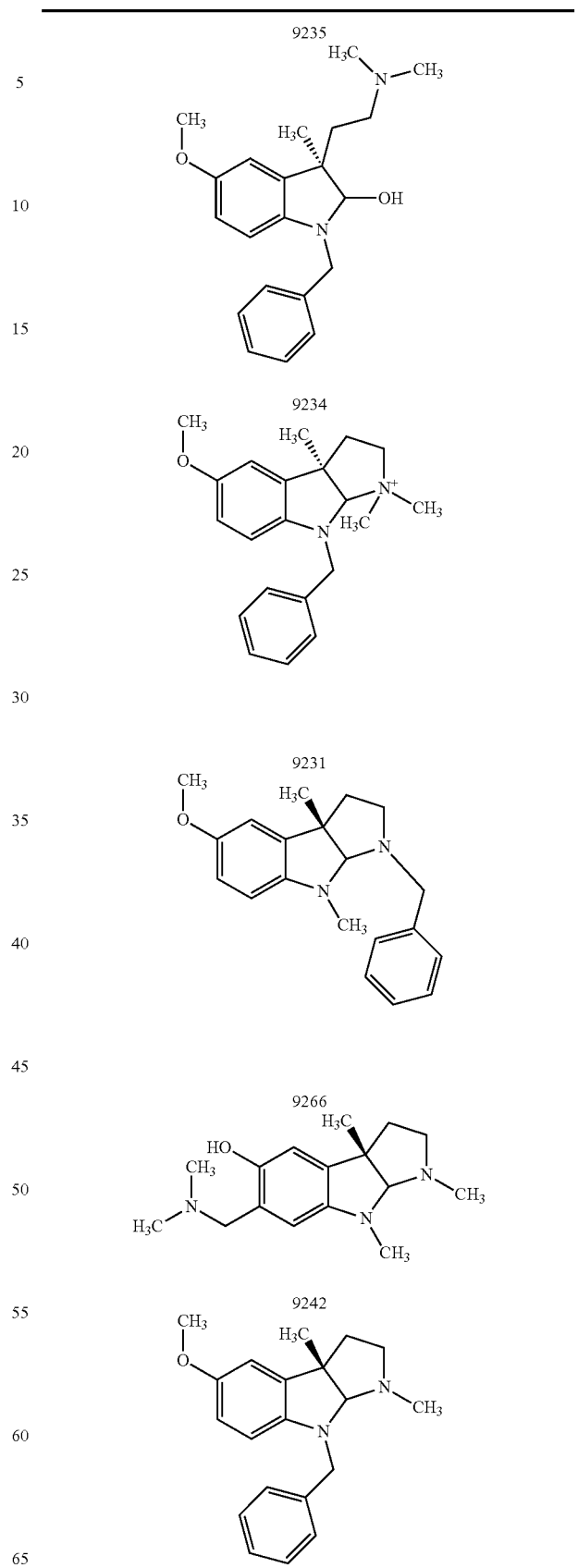

TABLE 2-continued
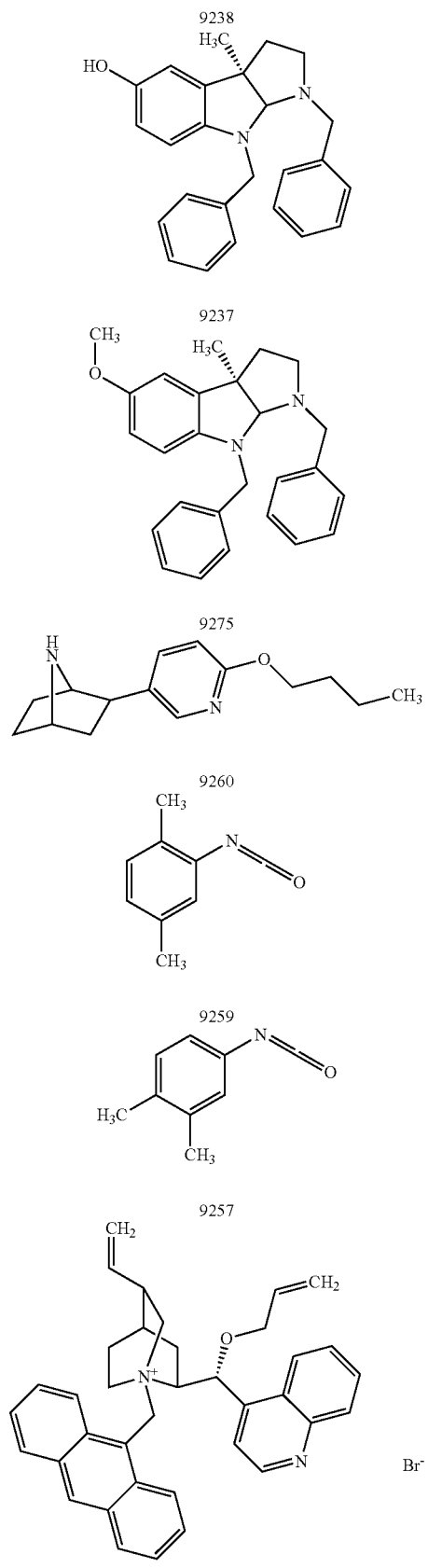
TABLE 2-continued
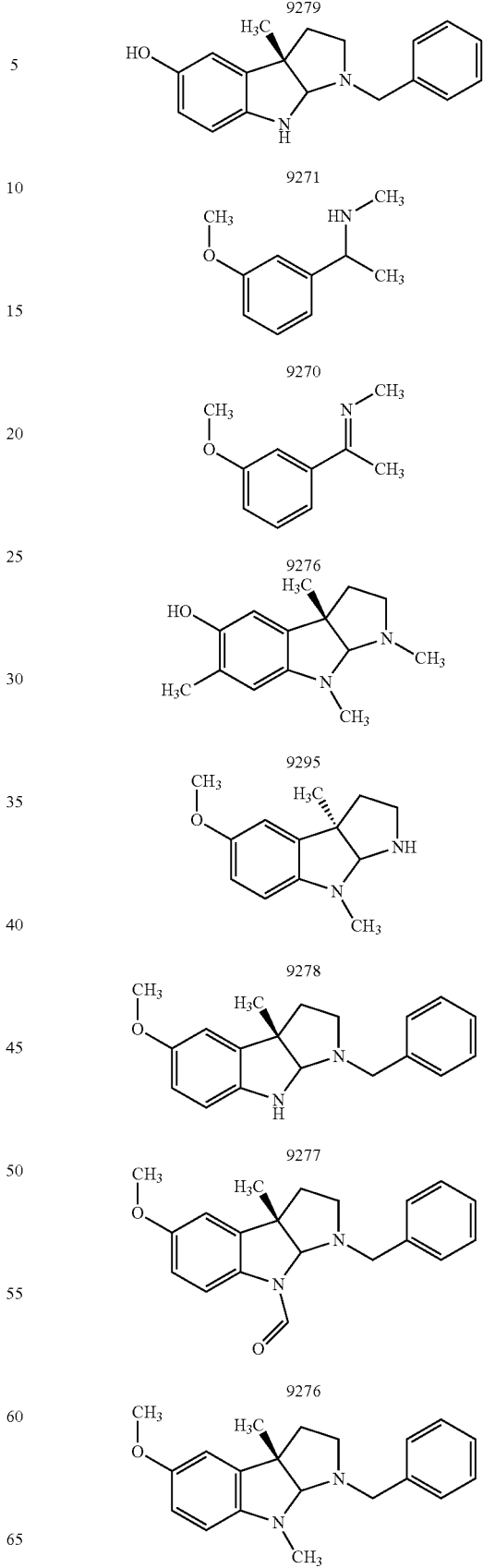

TABLE 2-continued
9305
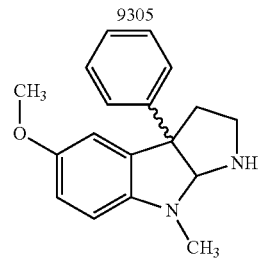
9293
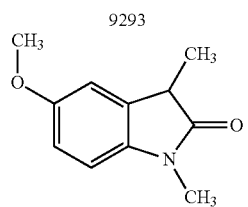
9292
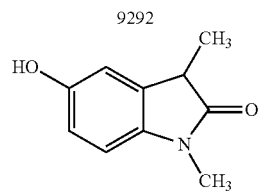
9291
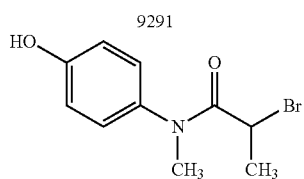
9311
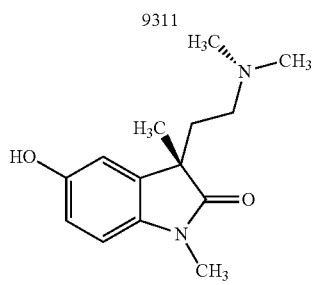
9302
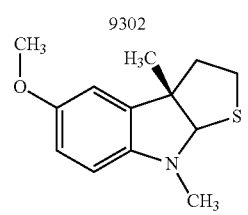
9301
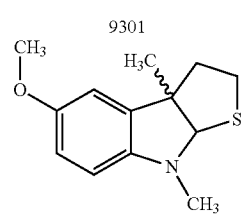
TABLE 2-continued
9295
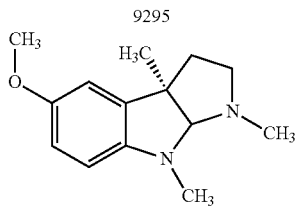
9317
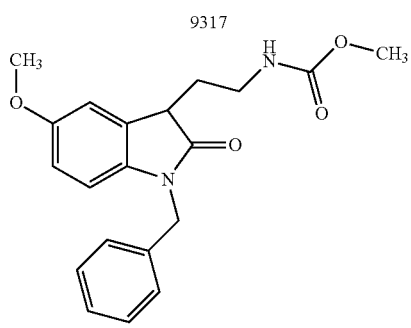
9310
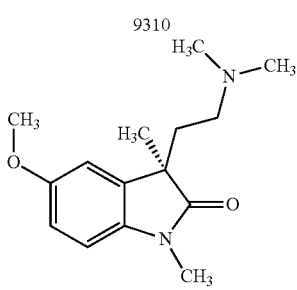
9309
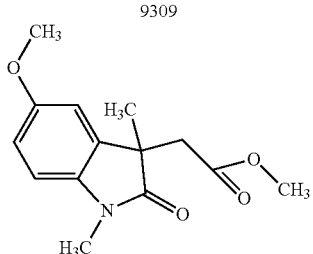
9306
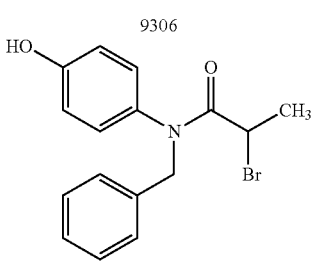
9234
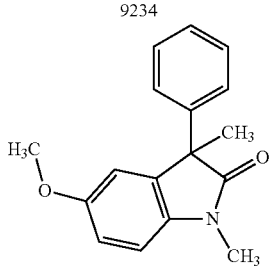

TABLE 2-continued
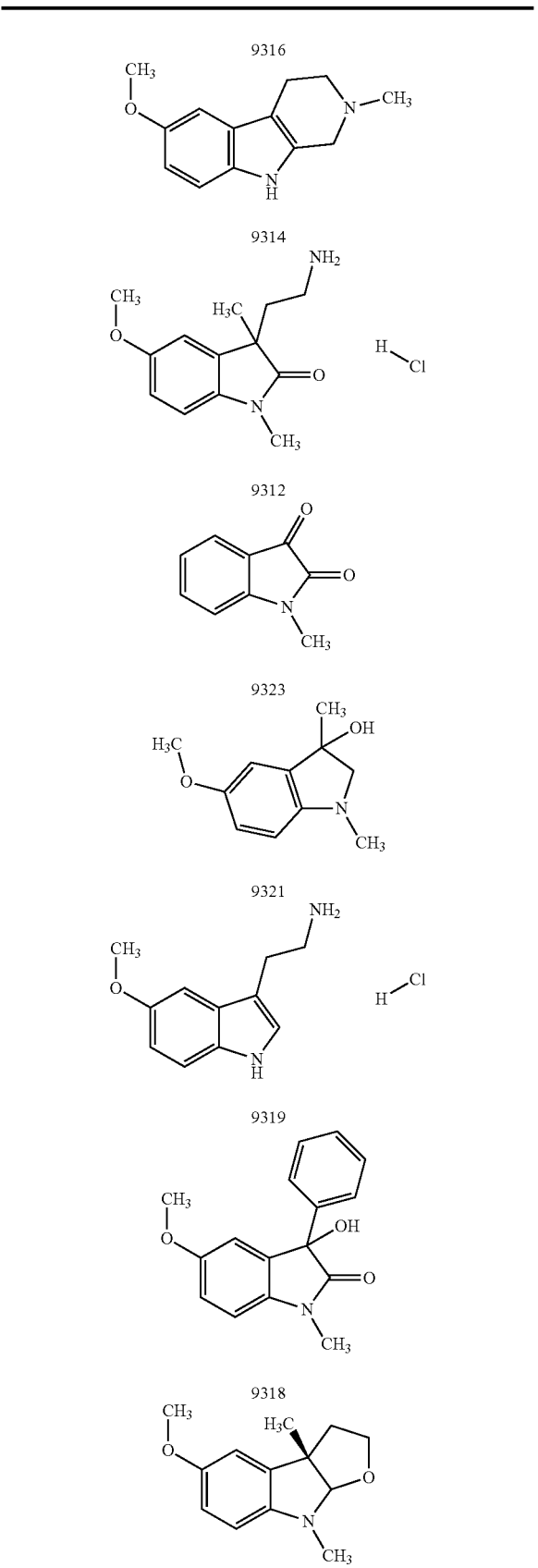
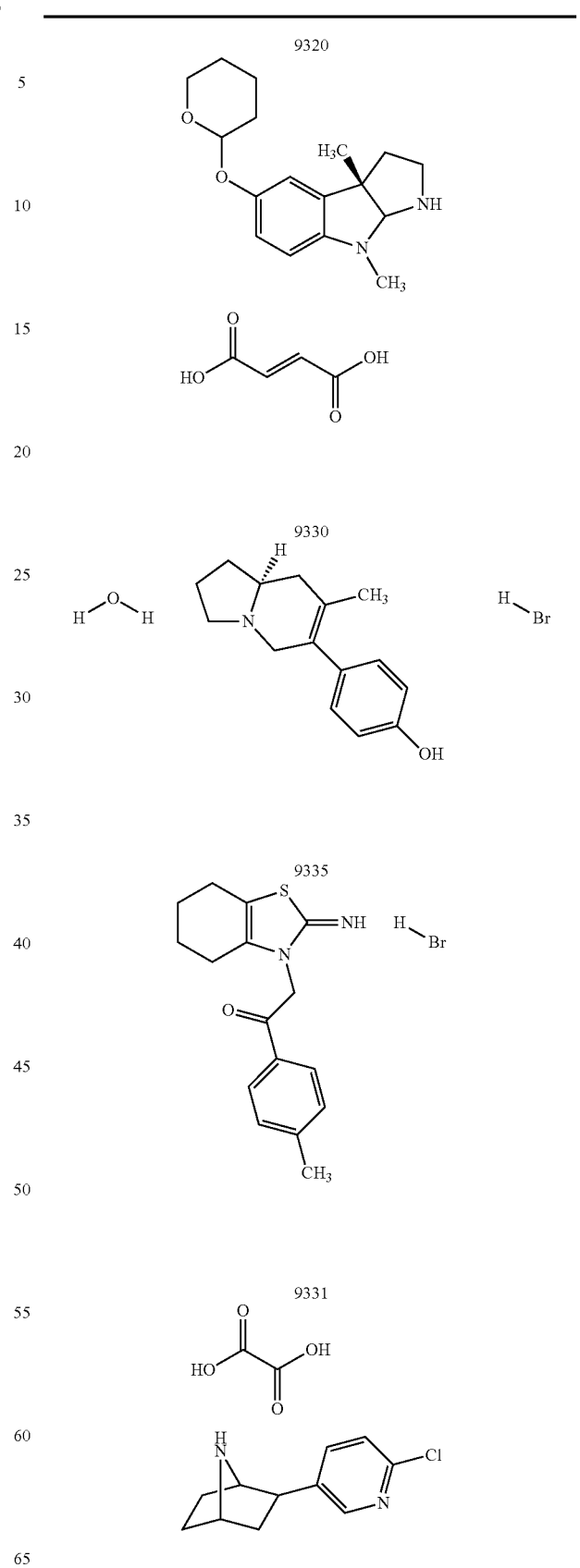

TABLE 2-continued

9286

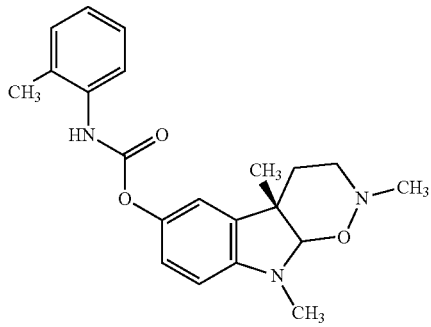

9287

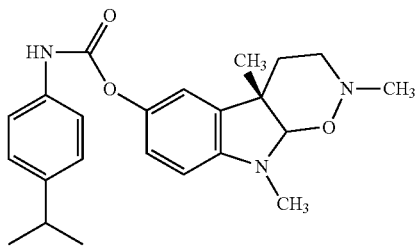

9290

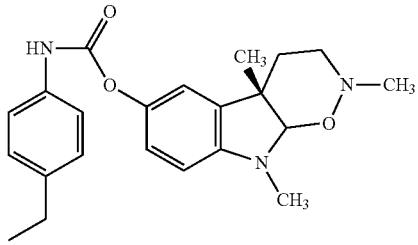

In one embodiment, the present invention provides a method of inhibiting production of amyloid precursor protein in a cell, comprising contacting the cell with a compound having the formula I-XVI and any combination thereof. As used herein, "inhibiting" means decreasing the amount or concentration of amyloid precursor protein. "Inhibition" also refers to halting or reducing the production of amyloid protein precursor, wherein the concentration of amyloid protein precursor is reduced or may not be reduced. Thus, the inhibition of production of amyloid precursor protein can be measured, for example, by comparing the amount of amyloid precursor protein produced by cells after contacting the cells with the compound having the formula I-XIII and any combination thereof, with the amount of amyloid precursor protein produced by control cells that have not been contacted with a compound having the formula I-XIII and any combination thereof. In one embodiment, the cell that is contacted with the compound is in vivo, ex vivo, or in vitro. The cell of this invention can be a mammalian cell, desirably a human cell.

In a desirable embodiment, the compounds inhibit production of amyloid precursor protein, $A\beta_{1}$-$_{40}$, and/or $A\beta_{1}$-$_{42}$ in a cell or a mammal by at least 30, 50, 60, 70, 80, 90, 95, or 100% compared to a buffer control, as measured using standard assays such as those described herein. In another desirable embodiment, the compound inhibits production of amyloid precursor protein, $A\beta_{1}$-$_{40}$, and/or $A\beta_{1}$-$_{42}$ in a cell or a mammal by at least 2, 5, 10, 20, or 50-fold compared to a buffer control, as measured using standard assays such as those described herein.

As used herein, "contacting" means exposure of at least one cell to a compound of the present invention. The cell of this invention can be, but is not limited to, a neural cell or supporting cell (e.g., glial or astrocyte). The term "neural cell" is defined as any cell that can be located in the central or peripheral nervous system or is a precursor or derivative thereof, including, for example, but not limited to, neuronal cells, glial cells, neural stem cells, neuronal stem cells and neuroblasts. The cell can be contacted in vitro with the compound, for example, by adding the compound to the culture medium (by continuous infusion, by bolus delivery, or by changing the medium to a medium that contains the compound), or the cell can be contacted with the compound in vivo (e.g., by local delivery, systemic delivery, intravenous injection, bolus delivery, or continuous infusion). In vitro contact may be preferred, for example, for measuring the effect of the compound on a population of cells. In vivo contact would be employed for inhibiting production of amyloid precursor protein in a subject in need of such inhibition, (e.g., a subject) with a neurodegenerative disease, for example, Alzheimer's Disease.

The subject of this invention can be any mammal that produces amyloid precursor protein, such as a primate and more desirably, a human. The subject of this invention can also be domesticated animals, such as cats, dogs, etc., livestock (e.g., cattle, horses, pigs, sheep, goats, etc.), and laboratory animals (e.g., mouse, rabbit, rat, guinea pig, etc.).

The duration of contact with a cell or population of cells is determined by the time the compound is present at physiologically effective levels or at presumed physiologically effective levels in the medium or extracellular fluid bathing the cell or cells. Desirably, the duration of contact is 1-48 hours and, more desirably, for 24 hours, but such time would vary based on the half-life of the compound and could be optimized by one skilled in the art using routine experimentation.

Examples of compounds used in the methods of this invention for inhibiting amyloid protein precursor include, but are not limited to, (+)-phenserine, (+)-cymserine, (+)-$N^1$-phenethylnorcymserine, or (+)-$N^1$,$N^8$-bisnorcymserine. In a desired embodiment, the compound is (+)-phenserine, compound V, wherein X and Y are $NCH_3$, $R_3$ and $R_8$ are methyl, and the compound is the substantially pure (+)-enantiomer, or compound VII, wherein X is $NR_5$, where $R_5$ is benzyl, $R_6$ is $(CH_2)_2N(CH_3)_2$, and $R_8$ is methyl.

In another embodiment, the present invention also provides a method of inhibiting production of amyloid precursor protein in a subject, comprising administering to the subject an effective amount of a compound having the structure I-XVI and any combination thereof in a pharmaceutically acceptable carrier, whereby the compound inhibits production of amyloid precursor protein in the subject.

In a desirable embodiment, the compounds of the invention inhibit production of amyloid precursor protein, $A\beta_{1}$-$_{40}$, and/or $A\beta_{1}$-$_{42}$ in the subject or in a sample from the subject by at least 30, 50, 60, 70, 80, 90, 95, or 100% compared to a buffer control, as measured using standard assays such as those described herein. In another desirable embodiment, the compound inhibits production of amyloid precursor protein, $A\beta_{1}$-$_{40}$, and/or $A\beta_{1}$-$_{42}$ in the subject or in a sample from the subject by at least 2, 5, 10, 20, or 50-fold compared to a buffer control, as measured using standard assays such as those described herein.

The compounds of the present invention can be administered in vivo to a subject in need thereof by commonly employed methods for administering compounds in such a way to bring the compound in contact with cells. The compounds of the present invention can be administered orally, parenterally, transdermally, extracorporeally, topically or the like, although oral or parenteral administration is typically desired. Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous, intraarticular and intratracheal routes. Additionally, the compound can be administered via a slow release or sustained release system such that a constant dosage is maintained. See, e.g., U.S. Pat. No. 3,610,795, which is incorporated by reference herein in its entirety. The compounds can also be administered using polymer based delivery systems, including, for example, microencapsulation, which techniques are well known in the art.

The dosage of the compound varies depending on the weight, age, sex and condition of the subject as well as the method and route of administration. As an, example, the dosage of the compound is from about 0.1 mg/kg to about 100 mg/kg of body weight. The lower limit for the dosage can be about 0.1, 0.5, 1, 2, 5, 10, 15, 20, 25, 30, or 40 mg/kg and the upper limit can be about 10, 15, 20, 25, 30, 40, 50, 60, 70, 80, 90, or 100 mg/kg. Any lower limit can be used with any upper limit. More desirably, the compound is administered in vivo in an amount of about 1 to about 20 mg/kg. Thus, an administration regimen could include long-term, daily treatment. By "long-term" is meant at least two weeks and, desirably, several weeks, months, or years of duration. Necessary modifications in this dosage range may be determined by one of ordinary skill in the art using only routine experimentation given the teachings herein. See *Remington's Pharmaceutical Sciences* (Martin, E. W., ed., latest edition), Mack Publishing Co., Easton, Pa. The dosage can also be adjusted by the individual physician in the event of any complication.

The compounds can be administered conventionally as compositions containing the active compound as a predetermined quantity of active material calculated to produce the desired therapeutic effect in association with the required diluent (i.e., carrier or vehicle). Depending on the intended mode of administration, the compound can be in pharmaceutical compositions in the form of solid, semi-solid or liquid dosage forms, such as, for example, tablets, suppositories, pills, capsules, powders, liquids, suspensions, lotions, creams, gels, or the like, desirably in unit dosage form suitable for single administration of a precise dosage. The compositions will include, as noted above, an effective amount of the selected compound in combination with a pharmaceutically acceptable carrier and, in addition, may include other medicinal compounds, pharmaceutical compounds, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying compounds, pH buffering compounds and the like, for example, sodium acetate, sorbitan monolaurate, triethanolamine sodium acetate, triethanolamine oleate, etc. Thus, the compositions are administered in a manner compatible with the dosage formulation and in a therapeutically effective amount. As discussed above, precise amounts of active ingredient required to be administered depend on the judgment of the practitioner and are peculiar to each individual.

For oral administration, fine powders or granules may contain diluting, dispersing, and/or surface active compounds, and may be presented in water or in a syrup, in capsules or sachets in the dry state, or in a nonaqueous solution or suspension wherein suspending compounds may be included, in tablets wherein binders and lubricants may be included, or in a suspension in water or a syrup. Where desirable or necessary, flavoring, preserving, suspending, thickening, or emulsifying compounds may be included. Tablets and granules are desired oral administration forms, and these may be coated.

In another embodiment, the present invention provides a method of treating a disorder associated with abnormal production of amyloid precursor protein, such as, for example, dementia in a subject, comprising administering to the subject an effective amount of the compound having the formula I-XVI and any combination thereof in a pharmaceutically acceptable carrier, whereby the compound treats the disorder in the subject. As used herein, the term "dementia" describes a neurodegenerative disorder that results from an organic braisn disease in which a subject experiences usually irreversible deterioration of intellectual faculties with accompanying emotional disturbances. An example of dementia includes, but is not limited to, Alzheimer's disease. An example of another disorder that can be treated by the methods of this invention includes, but is not limited to, cerebral amyloidosis. In a desirable embodiment, a compound used for the treatment of dementia improves a symptom associated with dementia or Alzheimer's, stabilizes a symptom, or delays the worsening of a symptom. In other desirable embodiments, the compound increases the life-span of a subject compared to the average life-span of corresponding subjects not administered the compound. In yet other desirable embodiments, the compound is used to prevent or delay the onset of dementia or Alzheimer's.

In general, an "effective amount" of a compound is that amount needed to achieve the desired result or results. Thus, for example, administering to a subject (e.g., a human) with Alzheimer's disease an effective amount of a compound of the present invention can result in slowing, stopping, or even possibly reversing the deterioration of the subject's intellectual faculties and other accompanying neurological signs and symptoms. Therefore, the inhibition of the production of amyloid precursor protein, by the methods of the present invention, treats the subject with Alzheimer's disease. The effective amount of the compound needed to treat dementia is from about 0.5 mg to about 200 mg. The lower limit for the effective amount of the compound can be about 0.5, 1, 2, 5, 10, 20, 30, 40, 50, 100, or 150 mg, and the upper limit can be about 50, 60, 70, 80, 90. 100, 110, 120, 130, 140, 150, 160, 170, 180, 190, or 200 mg. Any lower limit can be used with any upper limit. In one embodiment, when the subject is a human, the effective amount of compound to treat dementia is from about 0.5 to about 100 mg. In another embodiment, (+)-phenserine, (+)-cymserine, (+)-$N_1$-phenethylnorcymserine, (+)-$N^1$,$N^8$-bisnorcyrnserine, compound V, wherein X and Y are $NCH_3$, $R_3$ and $R_8$ are methyl, and the compound is the substantially pure (+)-enantiomer, or compound VII, wherein X is $NR_5$, where $R_5$ is benzyl, $R_6$ is $(CH_2)_2N(CH_3)_2$, and $R_8$ is methyl can be used in these amounts to treat dementia. In a desired embodiment, (+)-phenserine can be used in these amounts to treat dementia in a subject.

In a further embodiment, the present invention relates to a method of binding an amyloid precursor protein messenger RNA 5' untranslated region (5'UTR) in a cell, comprising contacting the cell with a compound having the formula I-XVI and any combination thereof, whereby the compound binds the amyloid precursor protein messenger RNA 5' untranslated region in the cell, thereby inhibiting amyloid protein production. The amyloid precursor protein messenger RNA 5'UTR confers translational control of PAPP protein synthesis. In one embodiment, (+)-phenserine, (+)-cymserine, (+)-$N^1$-phenethylnorcymserine, (+)-$N^1$,$N^8$-bisnorcymserine, compound V, wherein X and Y are $NCH_3$, $R_3$ and $R_8$ are methyl, and the compound is the substantially pure (+)-enantiomer, or compound VII, wherein X is $NR_5$, where $R_5$ is benzyl, $R_6$ is $(CH_2)_2N(CH_3)_2$, and $R_8$ is methyl can be used to bind the amyloid precursor protein with messenger RNA 5' UTR. In a desired embodiment, (+)-phenserine can be used to bind to an amyloid precursor protein messenger RNA 5' untranslated region in a cell. In a desirable embodiment, at least 30, 50, 60, 70, 80, 90, 95, or 100% of the amyloid precursor protein mRNA in a cell is bound by the compound.

In a further embodiment, the present invention relates to a method of inhibiting translation of an amyloid precursor protein messenger RNA in a cell, comprising contacting the cell with a compound having the formula I-XVI and any combination thereof, whereby the compound binds the amyloid precursor protein messenger RNA 5' and/or 3' untranslated region in the cell, or binds a protein that interacts with the amyloid precursor protein messenger RNA 5' and/or 3' untranslated region in the cell, or alters a process, either indirectly or directly, such as glycosylation or phosphorylation that then changes the binding of a specific regulatory protein to amyloid precursor protein messenger RNA 5' and/or 3' untranslated region in the cell, thereby inhibiting amyloid protein production. In one embodiment, (+)-phenserine, (+)-cymserine, (+)-$N^1$-phenethylnorcymserine, (+)-$N^1$,$N^8$-bisnorcymserine, compound V, wherein X and Y are $NCH_3$, $R_3$ and $R_8$ are methyl, and the compound is the substantially pure (+)-enantiomer, or compound VII, wherein X is $NR_5$, where $R_5$ is benzyl, $R_6$ is $(CH_2)_2N(CH_3)_2$, and $R_8$ is methyl can be used to inhibit the translation of the amyloid precursor protein with messenger RNA. In a desired embodiment, (+)-phenserine can be used to inhibit the translation of the amyloid precursor protein messenger RNA by interfering with the post-transcriptional regulation of the amyloid precursor protein RNA in a cell. In a desirable embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ by at least 2, 5, 10, 20, or 50-fold compared to a buffer control, as measured using standard assays such as those described herein.

The present invention also provides a method of screening a compound for the ability to inhibit production of amyloid precursor protein, $A\beta_{1-40}$, and/or $A\beta_{1-42}$, comprising (a) contacting the cell with the compound having the formula I-XVI and any combination thereof, and (b) detecting a decrease in amyloid precursor protein, $A\beta_{1-40}$, and/or $A\beta_{1-42}$ production in a cell contacted with the compound as compared to the amount of amyloid precursor protein, $A\beta_{1-40}$ and/or $A\beta_{1-42}$ production in a control cell not contacted with the compound, whereby decreased production of amyloid precursor protein, $A\beta_{1-40}$, and/or $A\beta_{1-42}$ in the cell identifies the compound as having the ability to inhibit the production of amyloid precursor protein, $A\beta_{1-40}$, and/or $A\beta_{1-42}$ in a cell. As shown in the Examples section below, a person of skill in the art can measure the amount of βAPP, $A\beta_{1-40}$, and/or $A\beta_{1-42}$ production in a control population of cells and compare the production of βAPP, $A\beta_{1-40}$, and/or $A\beta_{1-42}$ in a population of cells contacted with a compound to be screened by the methods of the present invention. A decrease in the production of βAPP, $A\beta_{1-40}$, and/or $A\beta_{1-42}$ in a population of cells contacted with a compound as compared to the production of βAPP, $A\beta_{1-40}$, and/or $A\beta_{1-42}$ in a population of control cells identifies the compound as having the ability to inhibit production of amyloid precursor protein, $A\beta_{1-40}$, and/or $A\beta_{1-42}$. In a desirable embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ by at least 2, 5, 10, 20, or 50-fold compared to a buffer control, as measured using standard assays such as those described herein.

The present invention further provides a method of screening a compound for the ability to inhibit amyloid precursor protein production by binding an amyloid precursor protein messenger RNA 5' untranslated region, comprising (a) contacting the messenger RNA with the compound; (b) detecting the binding of the compound to the amyloid precursor protein-messenger RNA 5' untranslated region; and (c) detecting the inhibition of amyloid precursor protein production from an amyloid precursor protein-messenger RNA 5' untranslated region, thereby identifying a compound having the ability to inhibit amyloid precursor protein messenger RNA 5' untranslated region. The binding of the compound to the amyloid precursor protein messenger RNA 5' untranslated region inhibits β amyloid precursor protein (βAPP) from the messenger RNA by directly preventing the binding of the ribosomal translational subunit with the mRNA through steric hindrance. The detection of binding of a compound to the 5' UTR of the amyloid precursor protein messenger RNA can be carried out by methods standard in the art for detecting the binding of substances to nucleic acids such as RNA. The detection of inhibition of amyloid precursor protein production upon contact with the compound can be carried out by the methods provided in the Examples herein, as well as protocols well known in the art. The messenger RNA can be in a cell or in a cell-free environment (e.g., a cell-free translation system). In a desirable embodiment, at least 30, 50, 60, 70, 80, 90, 95, or 100% of the amyloid precursor protein mRNA in a cell is bound by the compound.

The present invention further provides a method of screening a compound for the ability to inhibit amyloid precursor protein, $A\beta_{1-40}$, and/or $A\beta_{1-42}$ production by inhibiting translation of the amyloid precursor protein messenger RNA, comprising (a) contacting the cell with the compound; and (b) detecting the inhibition of amyloid precursor protein, $A\beta_{1-40}$, and/or $A\beta_{1-42}$ production from an amyloid precursor protein RNA, thereby identifying a compound having the ability to inhibit amyloid precursor protein messenger RNA translation. In another embodiment, the screening method further comprises after step (a) detecting the amount of the amyloid precursor protein-messenger RNA. In one embodiment, the amount of amyloid precursor protein mRNA is not inhibited by the compound or is inhibited by less than 80, 80, 50, 40, 30, 20, or 10%. In this case, the compound primarily or only inhibits the translation of amyloid precursor protein. It is also contemplated that in other embodiments a compound may inhibit both transcription and translation of amyloid precursor protein or inhibit only transcription of amyloid precursor protein. While not meant to limit the invention to any particular mechanism of action, the inhibition of translation by the compound can result from the binding of the compound to the amyloid precursor protein messenger RNA 5' and/or 3' untranslated region(s) inhibiting 3 amyloid precursor protein (βAPP) from the messenger RNA by directly preventing the binding of the ribosomal translational subunit with the mRNA through steric hindrance or by inhibiting the binding of an important regulatory protein, or the binding of the compound to the regulatory protein or by the compound modifying an important regulatory protein such that it no longer can interact with the amyloid precursor protein RNA. The direct detection of binding of a compound to the 5' and/or 3' UTR(s) of the amyloid precursor protein messenger RNA can be carried out by methods standard in the art for detecting the binding of substances to nucleic acids such as RNA, such as NMR or mass spectroscopy. The detection of inhibition of amyloid precursor protein production upon contact with the compound can be carried out by the methods provided in the Examples herein, as well as protocols well known in the art. The messenger RNA can be in a cell or in a cell-free environment (e.g., a cell-free translation system). In a desirable embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, as measured using standard assays such as those described herein. In another desirable embodiment, the compound inhibits production of amyloid precursor protein, $A\beta_{1-40}$, and/or $A\beta_{1-42}$ by at least 2, 5, 10, 20, or 50-fold compared to a buffer control, as measured using standard assays such as those described herein. In yet another desirable embodiment, at least 30, 50, 60, 70, 80, 90, 95, or 100% of the amyloid precursor protein mRNA in a cell is bound by the compound. In still another embodiment, at least 30, 50, 60, 70, 80, 90, 95, or 100% of the compound is directly or indirectly bound to an amyloid precursor protein messenger RNA 5' or 3' untranslated region or to an RNA binding protein that interacts with the amyloid precursor protein messenger RNA 5' or 3' untranslated region.

In another embodiment, the invention relates to a method of screening a compound for the ability to inhibit amyloid protein production by eliciting a change in reporter gene expression, comprising:
(a) contacting a cell transfected with a reporter gene containing the 5' and/or 3' UTR(s) of the amyloid precursor protein messenger RNA with the compound,
and
(b) detecting a decrease in reporter gene expression or activity; thereby identifying a compound having the ability to inhibit amyloid precursor protein messenger RNA translation.

In a desirable embodiment, the compound inhibits reporter gene expression or activity by at least 30, 50, 60, 70, 80, 90, 95, or 100% compared to a buffer control, as measured using standard assays such as those described herein. In another desirable embodiment, the compound inhibits reporter gene expression or activity by at least 2, 5, 10, 20, or 50-fold compared to a buffer control, as measured using standard assays such as those described herein.

The compounds used in the screening methods of this invention can be, but is not limited to, a compound having the structure I-XVI and any combination thereof. In various embodiments, the compound is a (+)-isomer, (+)-isomer, or a racemic mixture. In various embodiments of any of the methods of the invention, the compound is a (+)-isomer, (−)-isomer, or a racemic mixture of MES 9295 (FIG. 13E). In other embodiments of any of the methods of the invention, the compound is not a (+)-isomer, (−)-isomer, or a racemic mixture of MES 9295.

In desirable embodiment of any of the aspects of the invention, the compound inhibits cholinesterase activity, such as acetylcholinesterase or butyrylcholinesterase activity, by less than 80, 70, 60, 50, 40, 30, 20, 10, or 5% (in order of increasing preference) relative to a buffer only control. In other desirable embodiments, inhibition of cholinesterase activity, such as acetylcholinesterase or butyrylcholinesterase activity, by the compound is at least 2, 5, 10, 20, 50, or 100-fold less than the inhibition of cholinesterase activity by the corresponding amount of (−)-phenserine. In other desirable embodiments, inhibition of cholinesterase activity, such as acetylcholinesterase or butyrylcholinesterase activity, by a (+) isomer or a racemic mixture is at least 2, 5, 10, 20, 50, or 100-fold less than the inhibition of cholinesterase activity by the corresponding amount of (−)-isomer. In yet other desirable embodiments, the compound is substantially free of cholinesterase inhibitory activity. Inhibition of cholinesterase activity can be measured using any standard assay. For example, the assay and the in vivo mouse model described in U.S. Pat. No. 4,791,107, 20 which is incorporated by reference in its entirety, or the in vivo mouse model described herein can be used.

In other desirable embodiments of any of the aspects of the invention, the compound results in a less than 20, 10, 5, or 2-fold increase in the amount of released lactate dehydrogenase (a marker of cell viability and integrity) relative to the amount of released lactate dehydrogenase in the absence of the compound or in the presence of a buffer control. In still other desirable embodiments, the amount of compound that is administered to a subject per kg body weight of the subject does not cause tremors or death when administered in the in vivo mouse model described herein. In yet other desirable embodiments, less than 80, 70, 60, 50, 40, 30, 20, 10, or 5% of the neuronal cells contacted with the compound are killed by the compound. In another desirable embodiment, the doesse of the compound is equal to or greater than 1 mg/kg of body weight, 5 mg/kg, or 10 mg/kg.

In other desirable embodiments of any of the aspects of the invention, the compound inhibits production of amyloid precursor protein, $A\beta_{1-40}$, and/or $A\beta_{1-42}$ by at least 30, 50, 60, 70, 80, 90, 95, or 100% compared to a buffer control. In another embodiment, the compound inhibits production of amyloid precursor protein, $A\beta_{1-40}$, and/or $A\beta_{1-42}$ by at least 30, 50, 60, 70, 80, 90, 95, or 100% compared to a buffer control, and inhibits cholinesterase activity by less than 80, 70, 60, 50, 40, 30, 20, 10, or 5% relative to a buffer only control. In other desirable embodiments, the compound inhibits intracellular and/or extracellular APP or Aβ production. In yet other desirable embodiments, the compound inhibits production of amyloid precursor protein in a cell or mammal by at least 2, 5, 10, 20, or 50-fold more than it inhibits cholinesterase activity in the cell or mammal. In still other desirable embodiments, the amount of compound required to inhibit production of amyloid precursor protein in a cell or mammal by 50% ($IC_{50}$ value) is at least 2, 5, 10, 20, 50, or 100-fold less than the amount of compound required to inhibit cholinesterase activity by 50% ($IC_{50}$ value) in the cell or mammal, as measured using standard assays.

In other desirable embodiments of any of the methods of the invention, the compound is (+)-3,3a,8,8a-tetrahydro-3a, 8-dimethyl-2H-thieno[2,3-b]indole-5-ol methyl ether; (+)-3, 3a,8,8a-tetrahydro-3a,8-dimethyl-2H-thieno[2,3-b]indole-5-ol; (+)-3,3a,8,8a-tetrahydro-3a,8-dimethyl-2H-thieno-[2, 3-b]indole-5-ol butyl carbamate; (+)-3,3a,8,8a-tetrahydro-3a,8-dimethyl-2H-thieno[2,3b]indole-5-ol heptylcarbamate; (+)-3,3a,8,8a-tetrahydro-3a,8-dimethyl-2H-thieno[2,3b]indole-5-ol phenylcarbamate; (+)-3,3a,8,8a-tetrahydro-3a,8-dimethyl-2H-thieno[2,3-b]indole-5-ol 2'-methylphenylcarbamate; (+)-3,3a,8,8a-tetrahydro-3a,8-dimethyl-2H-thieno[2,3-b]indole-5-ol 2' ethylphenylcarbamate; (+)-3,3a,8,8a-tetrahydro-3a,8-dimethyl-2H-thieno[2,3-b]indole-5-ol 2'-isopropylphenylcarbamate; (+)-3,3a,8,8a-tetrahydro-3a, 8-dimethyl-2H-thieno[2,3-b]indole-5-ol 4'-isopropylphenylcarbamate; (+)-3,3a,8,8a-tetrahydro-3a,8-dimethyl-2H-thieno[2,3-b]indole-5-ol 2',4'-dimethylphenylcarbamate; (+)-3,3a,8,8a-tetrahydro-3a,8-dimethyl-2H-thieno[2,3-b]indole-5-ol N,N-dimethylcarbamate; (+)-O-methyl-N(1)-noreseroline; (+)-3,3a,8,8a-tetrahydro-3a,8-dimethyl-2H-thieno[2,3-b]indole-5-ol methyl ether; (+)-3,3a,8,8a-tetrahydro-3a, 8-dimethyl-2H-thieno[2,3-b]indole-5 of ((−)-thiaphysovenol); (+)-3,3a,8,8a-tetrahydro-3a,8-dimethyl-2H-thieno[2,3-b]indole-5-ol 2',4'-dimethylphenylcarbamate; (+)-3,3a,8,8a-tetrahydro-3a,8-dimethyl-2H-thieno[2,3-b]indole-5-ol 2'-methylphenylcarbamate; (+)-3,3a,8,8a-tetrahydro-3a,8-dimethyl-2H-thieno[2,3-b]indole-5-ol 4'-isopropylphenylcarbamate; (+)-3,3a,8,8a-tetrahydro-3a,8-dimethyl-2H-thieno[2,3-b]indole-5-ol 4'-isopropylphenylcarbamate, or a mixture of the (+)- and (−)-enantiomers thereof (e.g., a racemic mixture). In other embodiments, the compound is the (+)-enantiomer or a mixture of the (+)- and (−)-enantiomers thereof (e.g., a racemic mixture) of a compound disclosed in column 2, line 16 through column 3, line 40 of U.S. Pat. No. 5,378,723 (Brossi et al., issued Jan. 3, 1995).

In other desirable embodiments of any of the methods of the invention, the compound is a compound that falls with the general formula (e.g., column 1, lines 11-52) and or a specifically disclosed compound (e.g., a compound listed in column 21, line 59 through column 38, line 42) in U.S. Pat. No. 4,791,107 (Hamer et al., issued Dec. 13, 1988), and the compound has negligible cholinesterase inhibitory activity (e.g., causes no detectable cholinesterase inhibition or causes less than 50, 40, 30, 20, 10, or 5% inhibition). In other desirable embodiments, administration of the compound produces no adverse side-effects due to inhibition of cholinesterase activity. These compounds can be the (+)- or (−)-isomers or a mixture thereof (e.g., a racemic mixture). In other embodiments, the compound is a compound that falls with the general formula and or a specifically disclosed compound in U.S. Pat. No. 4,791,107, and the compound is administered in a dose of at least 1 mg/kg, 5 mg/kg, or 10 mg/kg.

In other desirable embodiments of any of the methods of the invention, the compound is a compound that falls with a general formula disclosed in U.S. Pat. No. 5,378,723 (Brossi et al., issued Jan. 3, 1995), U.S. Pat. No. 5,171,750 (Brossi et al., issued Dec. 15, 1992), or U.S. Pat. No. 5,998,460 (Brossi et al, issued Dec. 7, 1999), and the compound has negligible cholinesterase inhibitory activity (e.g., causes no detectable cholinesterase inhibition or causes less than 50, 40, 30, 20, 10, or 5% inhibition) or is administered in a dose of at least 1 mg/kg, 5 mg/kg, or 10 mg/kg. [As an alternative, these structures could be cut and pasted into the application.] In other desirable embodiments of any of the methods of the invention, the compound is the (+)-isomer or a racemic mixture of a compound that falls with a general formula or is specifically disclosed in U.S. Pat. No. 5,378,723, U.S. Pat. No. 5,171,750, or U.S. Pat. No. 5,998,460.

In other embodiments of any of the methods of the invention, the compound is not (−)-phenserine, (−)-physostigmine, (−)-heptyl-physostigmine, (−)-physovenine, (−)-N(1)-nor-physostignaine, MES9217 (FIG. 13H), MES9299 (FIG. 13L), or MES9329 (FIG. 13M). In other embodiments of any of the methods of the invention, the compound is not a compound disclosed in U.S. Pat. No. 5,378,723, U.S. Pat. No. 5,171,750, U.S. Pat. No. 5,998,460, or U.S. Pat. No. 4,791, 107.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and is at room temperature, and pressure is at or near atmospheric.

General Considerations

Phenserine: Phenserine is a member of a family of compounds that are phenylcarbamates of hexahydropyrrolo indoles with specific side groups that provide it selectivity against either acetyl- or butyryl-cholinesterase, a high brain uptake and a long duration of pharmacological action (Greig et al., 1995; Brossi et al., 1996). The compound was synthesized in its optically (>99.9%) and chemically (>99.9%) pure (−)- and (+)-enantiomeric forms as a tartrate salt, as described (Yu and Brossi, 1988; Greig et al., 1995). The concentration of compound required to inhibit 50% AChE activity was 22 nM for (−)-phenserine, whereas >25,000 LEM was inactive for optically pure (+)-phenserine.

Drug treatment: SK-N-SH neuroblastoma cells were cultured on 60 mm dishes at a concentration of $3 \times 10^6$ cells, and SH-5Y-5Y neuroblastoma and U373 astrocytoma cell lines were plated in 100 mm dishes at a concentration of $3 \times 10^5$ cells. The cells were allowed to grow in complete medium (10% PBS, 2 mM glutamine in DMEM) for 3 to 4 days until they reached 70% confluence. To start the experiment, spent medium was removed and replaced with fresh medium (SKNSH-4 ml of DMEM+0.5% FBS; U373-5 ml of DMEM+ 2.5% FBS) containing 0, 5, or 50 μM phenserine. The cells were incubated at 37° C., 5% $CO_2$ for the specific times indicated. Different media and sera were purchased from Life Technologies (Gaithersburg, Md.).

Inhibitor treatment: One day prior to drug treatment, confluent cultures of U373 cells were pretreated with 25 nM of ERK specific inhibitor, PD98059 (Calbiochem-Novabiochem, La Jolla, Calif.), in 4.5 ml of 2.5% FBS, 2 mM glutamine and DMEM for 16 hours. Phenserine was added to each assay plate and a final volume of 5 ml was reached. To examine for PI 3 kinase involvement, an active 2 μM concentration of the PI 3 kinase inhibitor, LY294002 (Calbiochem-Novabiochem, La Jolla, Calif.), in 4.5 ml of 2.5% FBS, 2 mM glutamine and DMEM was added to each assay plate and incubated for 30 minutes prior to the addition of phenserine. Appropriate vehicle controls were run alongside treated samples.

Lysate preparation: At each time point, the spent medium was collected and stored at −70° C. for later analysis of secretory βAPP levels. The cells were washed twice with PBS, pH 7.4 and incubated on ice for 15 min for lysis with 100 μL of lysis buffer (20 mM HEPES, 2 mM EGTA, 50 mM (β-glycophosphate, 1 mM sodium orthovanadate, 1% Triton X-100, 10% glycerol) containing appropriate protease inhibitors (2 mM PMSF, 100 μg/mL aprotinin, 25 μM leupeptin and 20 μg/mL soybean trypsin inhibitor). Each lysate was microcentrifuged for 15 min at 14 000 rpm. Protein levels of the supernatant were analyzed by the Bradford protein assay (BioRad, Melville, N.Y.).

Western Blot: Fifteen μg of protein from each sample was mixed with the appropriate volume of 5× Laemmli buffer and boiled for 5 min at 100° C. The samples were loaded onto a 10% NuPAGE Bis-Tris gel in 1× NuPAGE MOPS SDS running buffer (NOVEX, San Diego, Calif.) and the proteins separated at 200 V for 45 min. The gels then were transferred onto nitrocellulose at 25 V for 1.5 h. The blots were blocked with 5% non-fat dry milk in 10 mM Tris, pH 8.0 containing 150 mM NaCl for 1 h and washed twice for 15 min in large volumes of TBST (10 mM Tris, pH 8.0, 150 mM NaCl and 0.05% Tween 20). Each blot was probed for 2 h with either 22C11 anti-βAPP-terminal antibody (Boehringer Mannheim, Indianapolis, Ind.), diluted to a concentration of 2.5 μg/mL or anti-activated ERK antibody (Promega, Madison, Wis.), diluted to a concentration of 25 ng/mL. The blots were washed twice for 15 min in TBST and placed in secondary antibody, anti-mouse IgG- or anti-rabbit IgG conjugated to horse radish peroxidase (Sigma, St. Louis, Mo.), for 30 min. Three final TBST washes of 20 min duration each were performed before the samples were detected by chemiluminescence and exposed to film, as per the manufacturer's instructions (Amersham Life Science Inc., Arlington Heights, Ill.). Additionally, all blots also were stained with Ponceau S (Sigma, St. Louis, Mo.) to determine equivalent loading of samples. Densitometric quantification of blots was undertaken by using a CD camera and NIH-IMAGE (version 4.1).

Lactate Dehydrogenase Assay: Measurement of released lactate dehydrogenase (LDH) in the conditioned medium was undertaken as a marker of cell viability and integrity, as described previously (Lahiri et al., 1997 and 1998).

Total Aβ Assay: Total Aβ peptide levels in SH-SY-SY and SK-N-SH cultured samples were assayed by a sensitive ELISA (Suzuki et al., 1994). For total Aβ measurements in conditioned medium, the rabbit polyclonal antibody #3160 (1-40 residues of Aβ) was used as a capture antibody for all species of Aβ peptide ($A\beta_{1-40}$ and $A\beta_{1-42}$) while monoclonal antibody 4G8 (17-25 residues of Aβ) was used to detect Aβ peptide levels, and the values were expressed as the mean of six independent assays.

Transfection: One day prior to transfection, U373 cells were plated onto 100 mm dishes at a density of $3\times10^5$ cells. On the day of transfection, the cells were given 5 ml of fresh media containing 10% FBS, 2 mM glutamine in DMEM. The cells were transfected using a calcium phosphate precipitation method, as per the manufacturer's protocol and described previously (Rogers et al., 1999). Briefly, for each plate, three μg of DNA (5'UTR APP-PSV2-CAT or PSV2-CAT vector) were placed in a final volume of 500 μL of 250 mM $CaCl_2$. The chloramphenicol acetyl transferase (CAT) gene was used as a reporter gene. The DNA solution was slowly pipetted into an aerated, equivalent volume of 2× HeBS, pH 7.05. The resulting precipitate was allowed to stand 10-20 min at RT before its addition to the cells. After 18 h, the medium was changed and the transfected cells were left for two days before drug treatment.

CAT Assay: The cell lysates from transfected U373 cells treated with phenserine were analyzed for their CAT activity using a colorimetric enzyme immunoassay (Boehringer Mannheim, Indianapolis, Ind.). Briefly, 50 μg of protein (an amount previously found to lie within the linear range of the assay) were placed onto anti-CAT coated microtiter plate modules and allowed to bind for 1 h at 37° C. The plates were washed thoroughly after each step. Next, a digoxigenin-labeled anti-CAT antibody was added to the samples and incubated for 1 h at 37° C. A subsequent antibody, anti-digoxigenin conjugated to peroxidase, was placed in the wells for another hour under similar conditions. Finally peroxidase substrate, ABTS, was added to each well and the absorbance of each sample was measured at a wavelength of 405 nm.

Northern Blotting: Total RNA (10 μg was extracted and prepared from treated astrocytoma cells using an RNA-STAT kit (Tel-test, Friendswood, Tex.). The samples were denatured in formamide, MOPS buffer, formaldehyde, dye mix and ethidium bromide at 65° C. for 10 min, placed on ice for 5 min and electrophoresed on a 1.0% agarose-formaldehyde gel. The gel was blotted onto Hybond Nitrocellulose filters and immobilized by LTV crosslinking and heating filters for 2 hours. Each filter was prehybridized in hyrbridization buffer (1% BSA, 7% SDS, 0.5 M phosphate buffer, pH 7, 1 inM EDTA) for at least 2 hours. The filter was hybridized overnight with probe. Following hybridization, the filters were washed twice with wash solution containing 0.5% BSA, 5% SDS, 40 mM phosphate buffer, pH 7, 1 mM EDTA for 30 min at 65° C. The βAPP cDNA probe corresponded to a unique internal BgIII/SpeI fragment generated from human βAPP cDNA (provided by John Kusiak, Gerontology Research Center, LRP, NIA, NIH). Equal loading of samples was verified by rehybridizing the filter with a human actin gene using an actin β-cDNA probe (Clontech Laboratories, Palo Alto, Calif.).

Plasmid Constructs: The plasmid PSV2-APP-CatD was provided by Dr. Rogers (1999). Briefly, the $pSV_2$(APP)CAT construct was generated by inserting a 90 bp fragment of the βAPP gene 5'-UTR immediately upstream of the CAT gene into the $pSV_2$ vector.

Statistics: A two-tailed Student's t-test was carried out to compare two means. When more than two means were compared, one-way analysis of variance, together with a Bartlett's test for homogeneity of variances and a Dunnett's multiple comparison test were used. The level of significance was defined as $P<0.05$.

Figure 3:
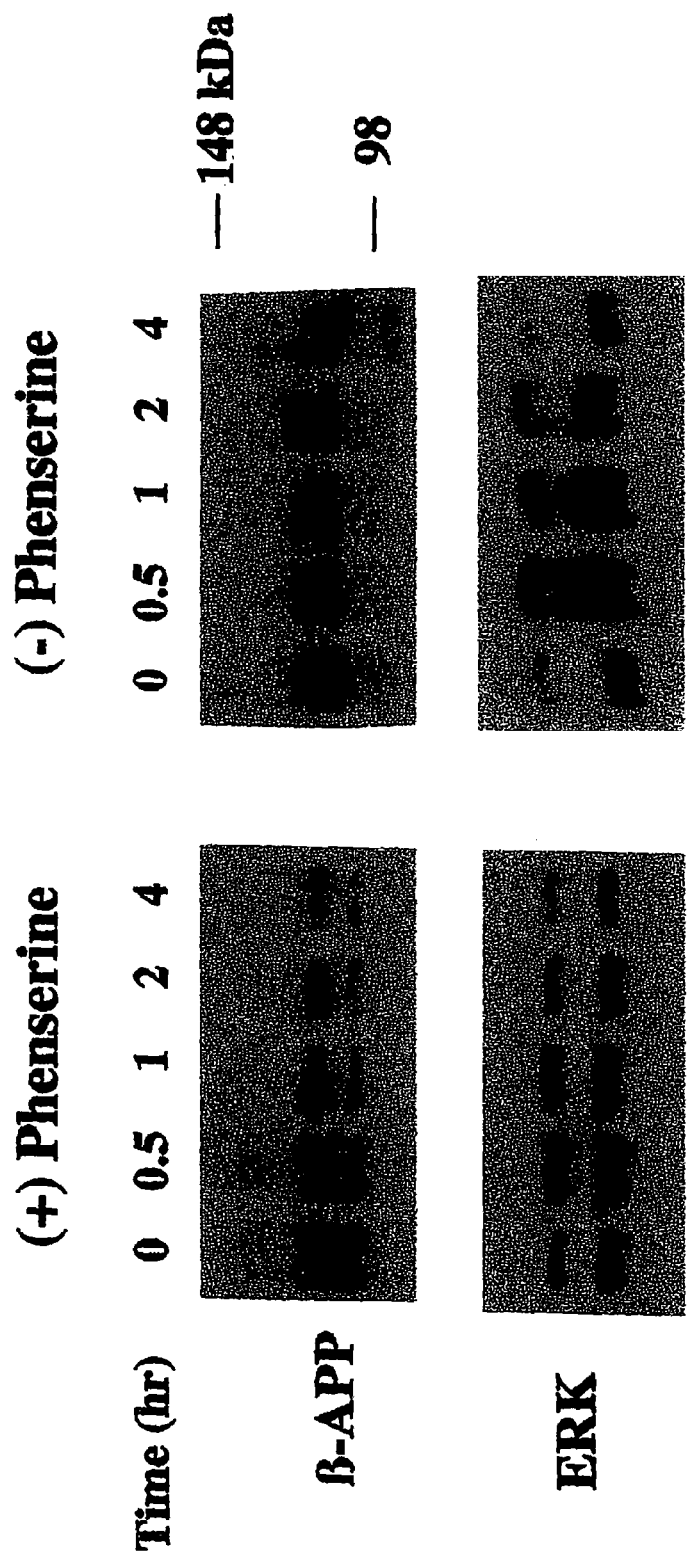
FIG. 3 shows effects of (+) and (−)-phenserine treatment of SH-SY5Y neuroblastoma cells on βAPP protein levels and ERK transcription factor levels.

Phenserine Decreases βAPP and Aβ Levels in Neuroblastoma Cells

βAPP protein levels were measured after treatment of the SH-SY-5Y cells with 5 μM (+)-phenserine and (−)-phenserine for 0.5, 1, 2, and 4 hours (FIG. 3). SH-SY5Y cells were incubated with 5 (+)-phenserine or (−) phenserine for 0, 0.5, 1, 2 and 4 hours to determine the effect of the drug on βAPP protein levels. Western blots of cell lysates containing 15 μg of total protein per lane were analyzed. The blot was sectioned into two halves and the top portion of the blot was probed with an N-terminal directed anti-βAPP antibody whereas the remaining blot was probed with an antibody directed to phosphorylated ERK. In accord with previous reports (Lahiri et al., 1997, 1998; Waskiewics and Cooper, 1995), two high molecular weight bands corresponded to alternate forms of βAPP (100-125 kDa) and ERK½ (42-46 kDa). The stereoisomeric forms of the drugs have opposite affects on cholinesterase activity: (+)-phenserine exhibits no anti-cholinesterase activity whereas (−)-phenserine has potent enzymatic activity (Greig et al., 1995; Brossi et al., 1996). In both experiments, the βAPP levels in the cell lysates slowly decreased at each time point with the most dramatic decline observed after 4 hours. During this period, the cells were also examined for their ability to induce signal transduction pathways. Mitogen stimulated kinase, ERK½, was detected in the treated samples at all times and peaked at the 30 minute to 1 hour period. Stress activated transcription kinases, p38 and JNK, were not detected in the samples. Furthermore, media samples were analyzed for levels of Aβ at 4 hours and, additionally, at 8 and 16 hours to assess whether or not decline in βAPP translated into a decline in total Aβ peptide levels. Levels of Aβ were below detectable levels in both control and (−)-phenserine treated cells. As a consequence, studies were repeated with SK-N-SH cells with (−)-phenserine and (+)-phenserine, which was used in all subsequent studies unless otherwise indicated.

Figure 4:
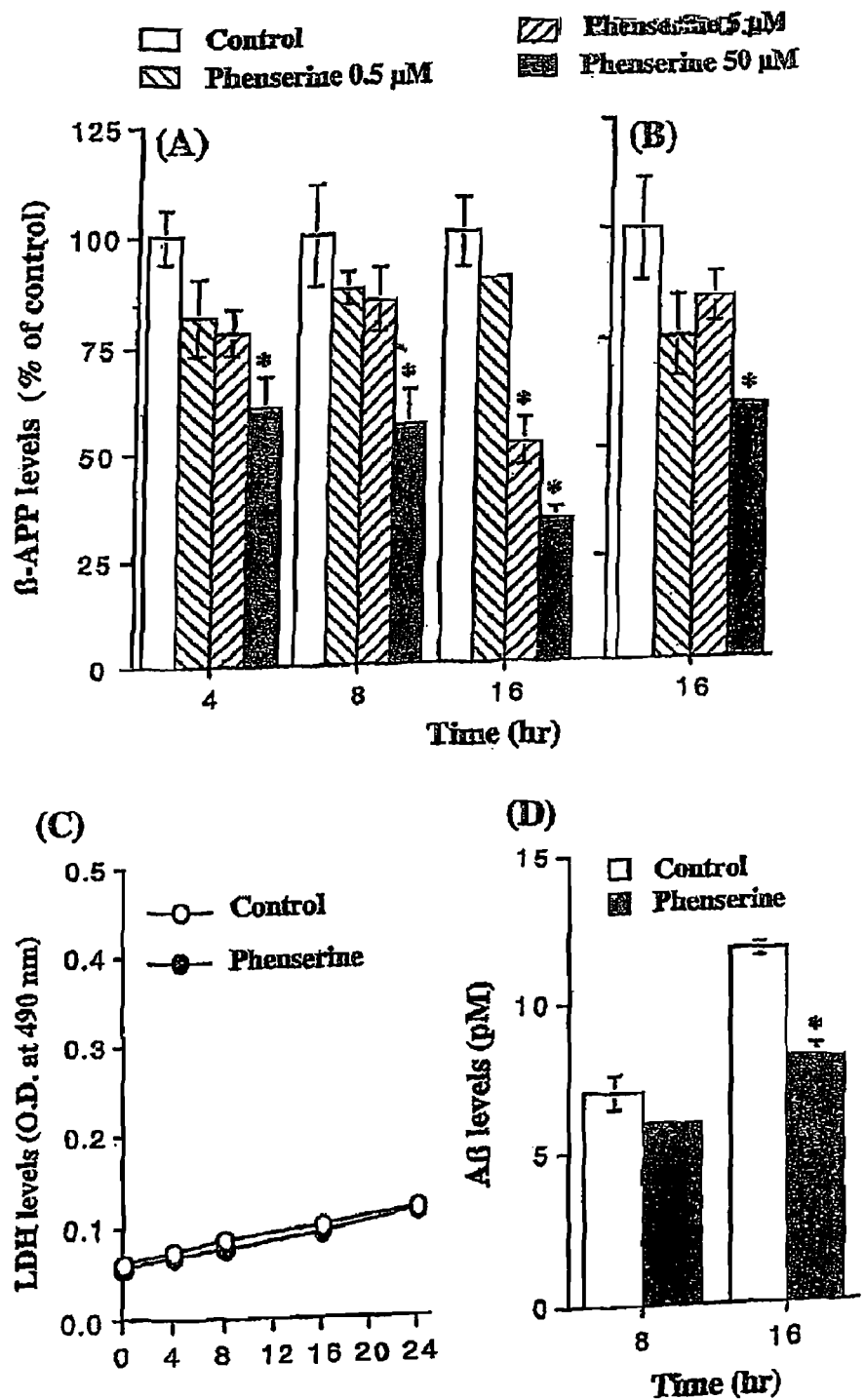
FIG. 4 shows effects of (−)-phenserine treatment of SK-N-SH neuroblastoma cells on extracellular βAPP protein levels (4A), intracellular βAPP protein levels (4B), toxicity (4C) and Aβ levels (4D).

SK-N-SH cells were incubated with either (−)-phenserine (FIG. 4) or with (+)-phenserine (FIG. 5) for up to 16 hours. FIG. 4 illustrates the effect of (−)-phenserine on βAPP protein levels (FIGS. 4A and 4B), LDH levels (FIG. 4C) and total Aβ levels (FIG. 4D). βAPP levels are shown as a percent of controls after pretreatment with 0.5, 5 and 50 µM (−)-phenserine for 4, 8 and 16 hours (*significantly different from control, $p<0.05$). Western blots of conditioned media (FIG. 4A) and cell lysates (FIG. 4B) were probed; with a N-terminal directed anti-βAPP antibody. Following phenserine treatment of SK-N-SH cells for 16 hours, βAPP levels were reduced in a time- and concentration-dependent manner in both conditioned media (FIG. 4A) and cell lysates (FIG. 4B).

LDH levels were measured in media from cells treated with and without 50 µM (−)-phenserine for up to 16 hours. There was no significant difference between treated and untreated levels up to 16 hours ($p>0.05$). This was not associated with cellular dysfunction, as determined by measurement of LDH levels versus untreated controls (FIG. 4C).

Figure 5:
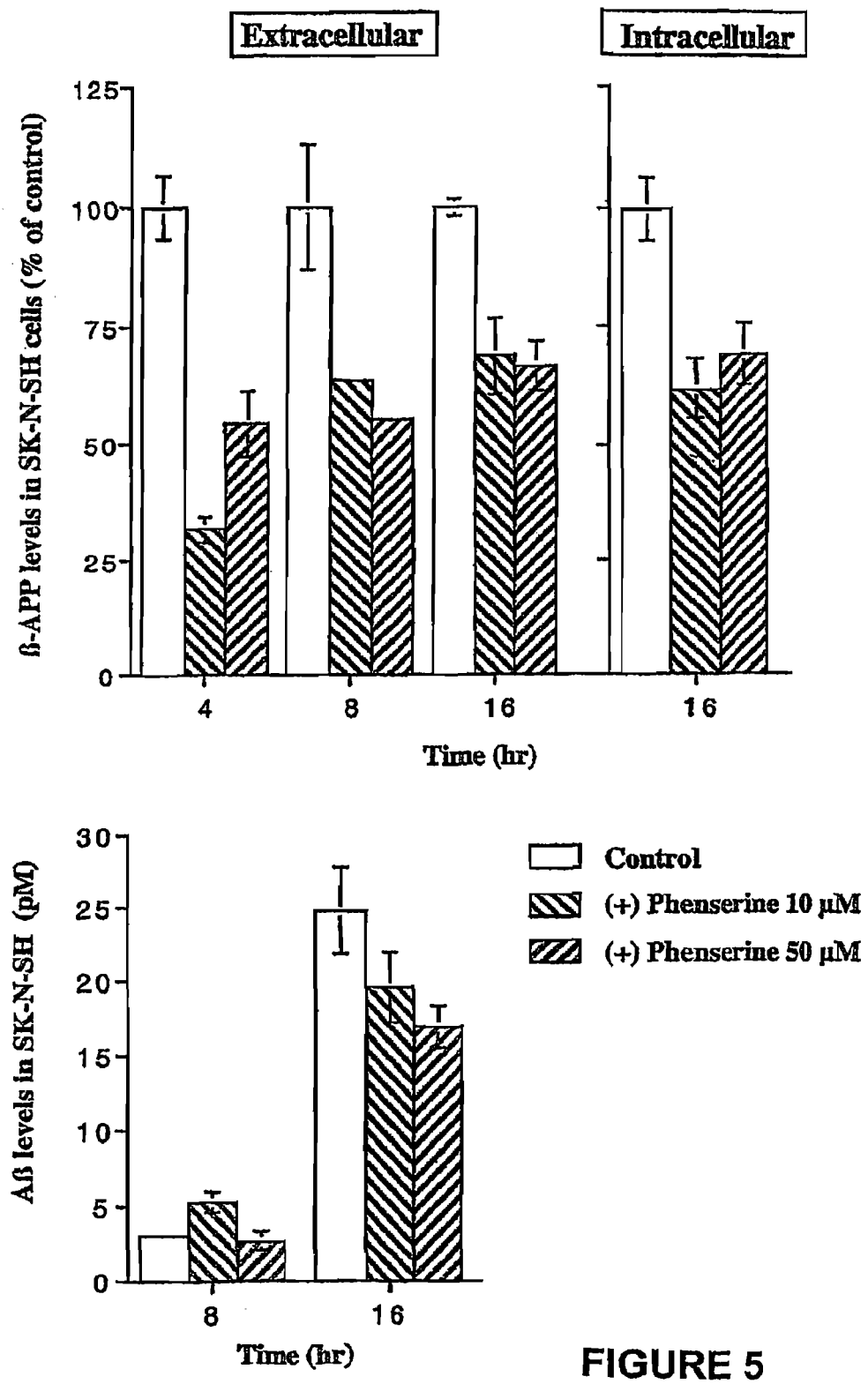
FIG. 5 shows Aβ and βAPP levels in SK-N-SH cells after administration of (+)-phenserine.

Quantification of levels of total Aβ was undertaken at 8 and 16 hours and results shown in FIG. 4D demonstrate a (−)-phenserine induced reduction of 14% and 31% ($p<0.002$), respectively, versus untreated controls. (+)-Phenserine possessed a similar concentration- and time-dependent action on ΠAPP levels. The concentration of total Aβ peptide was measured in media from SK-N-SH cells that were incubated with 50 µM (−)-phenserine for up to 16 hours. Levels fell from 6.95 to 5.95 µM (14%) at 8 hours, and from 11.75 to 8.1 pM (31%, $p<0.02$) at 16 hours in control and (−)-phenserine treated cell, respectively (FIG. 4D). Likewise, (+)-phenserine reduced BAPP protein levels and total Aβ peptide levels at 16 hours (FIG. 5). This was not associated with toxicity, as assessed by measurement of cell number and viability (LDH levels).

Figure 6:
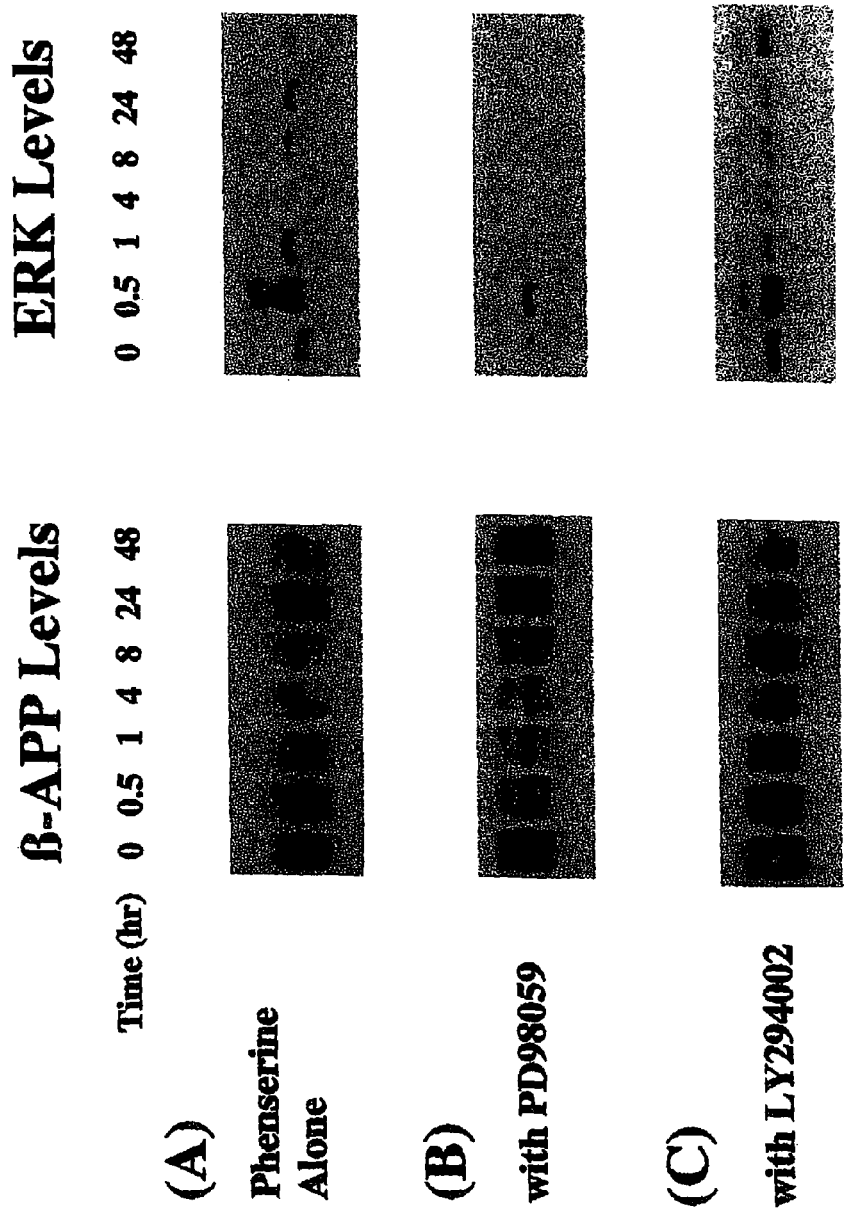
FIG. 6 shows (−)-phenserine treatment of U373 MG astrocytoma alone or in combination with ERK and PI 3 kinase inhibitors.

Phenserine Associated Decrease of βAPP Levels in Astrocytoma Cell Line U373 is not Dependent on ERK Activation Following an extended period of (−)-phenserine treatment, U373 cells exhibited a similar pattern of decreased βAPP protein synthesis. FIG. 6 is a representative of 4 experiments that showed that βAPP levels gradually decreased between 1 and 8 hours of treatment. U373 MG astrocytoma cells were treated with (−)-phenserine to determine its effect on βAPP protein levels. The addition of ERK inhibitor, PD98059, and PI 3 kinase inhibitor, LY294002, was carried out to ascertain whether or not (−)-phenserine action on βAPP was directed through these signaling pathways. Western blots of lysates (15 µg per lane) of U373 cells incubated with 50 µM of (−)-phenserine for 0, 0.5, 1, 4, 8, 24 and 48 hours were analyzed. The blot was divided into two sections. On the left panel, the blot was probed with anti-βAPP antibody and on the right panel, the blot was probed with anti-phosphorylated ERK antibody. After 8 hours, a slow recovery of βAPP was detectable (FIG. 6A) but its level was still lower than in untreated cells. The activation of ERK½ peaked at the 30 minute time point and remained elevated at a low level for the remainder of the assay.

In order to determine whether or not ERK involvement was directly related to phenserine treatment, the cells were pretreated with PD98059, a specific inhibitor of MAP kinase (FIG. 6B). U373 MG cells were pretreated with 25 nM PD98059 for 16 hours prior to (−)-phenserine treatment. Lysates were analyzed by western blots as described above. Although ERK levels decreased significantly, the pattern of βAPP levels induced by phenserine remained largely similar to U373 cells treated with drug without PD98059. In all cases, βAPP levels were decreased by in excess of 25%, as determined by densitometric quantification.

Phenserine action on βAPP through ERK independent, phophoinositol 3 kinase (PI 3 kinase) stimulation was also assessed. Treatment of astrocytoma cells with phenserine and LY294002, a specific inhibitor of PI 3 kinase, showed a similar pattern of βAPP levels when compared to (−)-phenserine alone treated cells (FIG. 6C). U373 MG cells were pretreated with 200 µM LY294002 for 1.5 hours prior to the addition of (−)-phenserine. The cell lysate of each sample was analyzed as described above. βAPP protein levels were reduced by in excess of 25% ($p<0.05$) with (−)-phenserine treatment in FIGS. 6A-C, as determined by densitometric quantification.

In summary, these studies demonstrate that the action of (−)-phenserine to reduce βAPP protein and total Aβ peptide levels did not occur via classical cholinergic or neurotransmitter mediated mechanism, as has been suggested by Buxbaum et al., (1990, 1992, 1994) and Nitsch et al. (1992, 1994). This was supported by two previously unreported lines of evidence. First, studies with the (+)-enantiomer, (+)-phenserine, that is devoid of anticholinesterase activity and hence cholinergic action, still reduced βAPP protein and total Aβ peptide levels (FIG. 5). Second, the actions of (−)-phenserine βAPP protein and total Aβ peptide persisted after the classical pathways involved in cholinergic modulation were blocked (FIG. 6). In addition, in separate studies, when 50 µM concentrations of the classical anticholinesterase, (−)-physostigmine, were applied to SK-N-SH cells, no reduction or change in βAPP protein and total Aβ peptide levels was found.

Figure 7A:
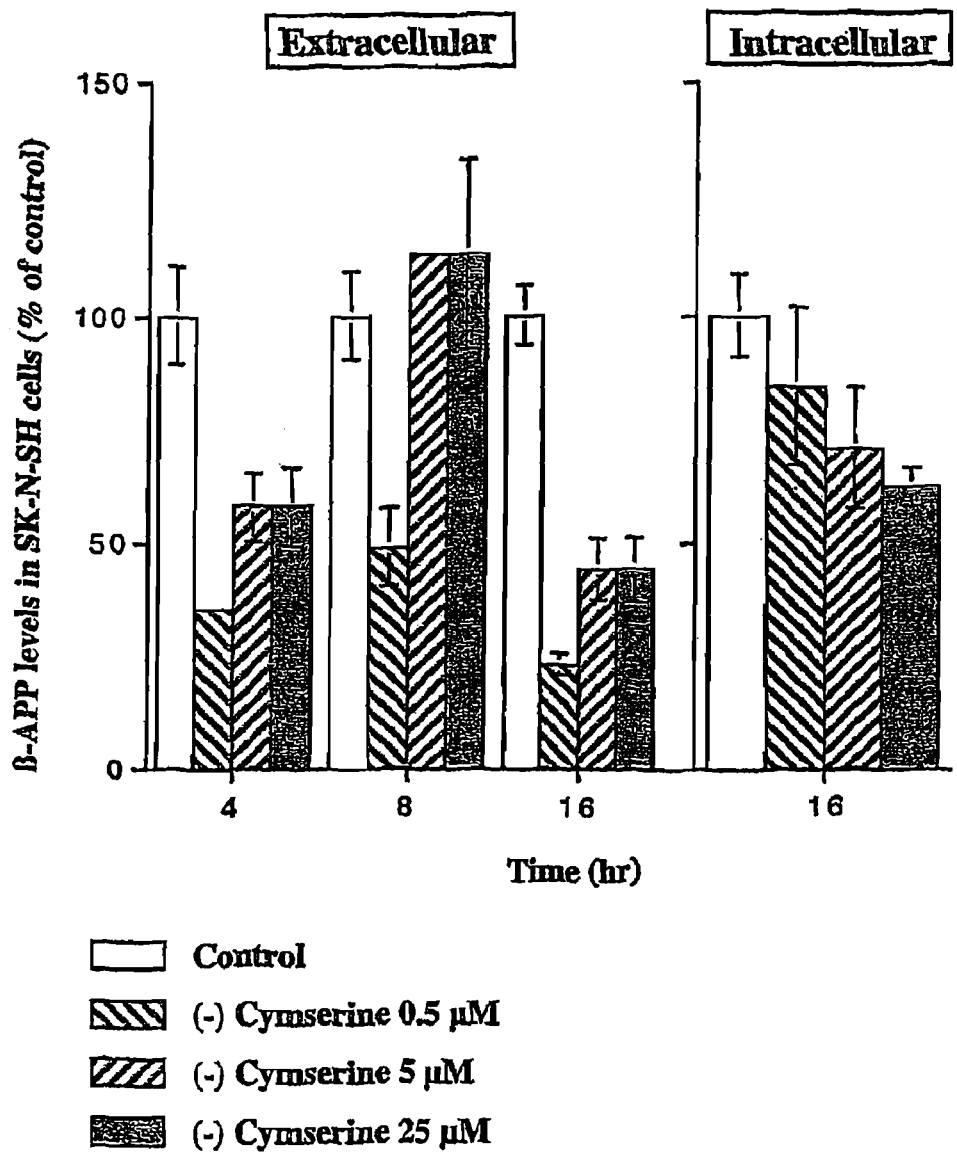
FIG. 7 shows βAPP protein levels in SK-N-SH cells after administration of cymserine and its analogs.
Figure 7B:
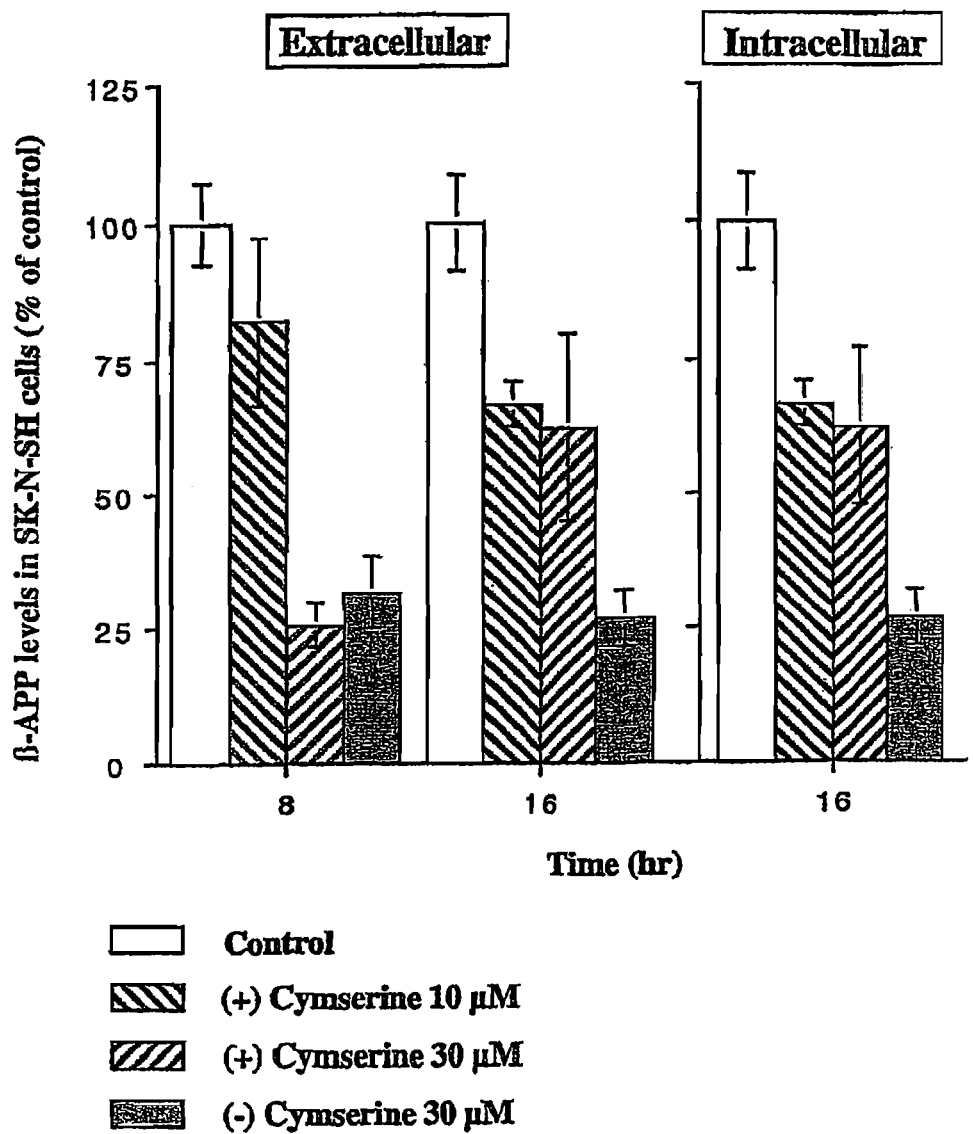
Figure 7C:
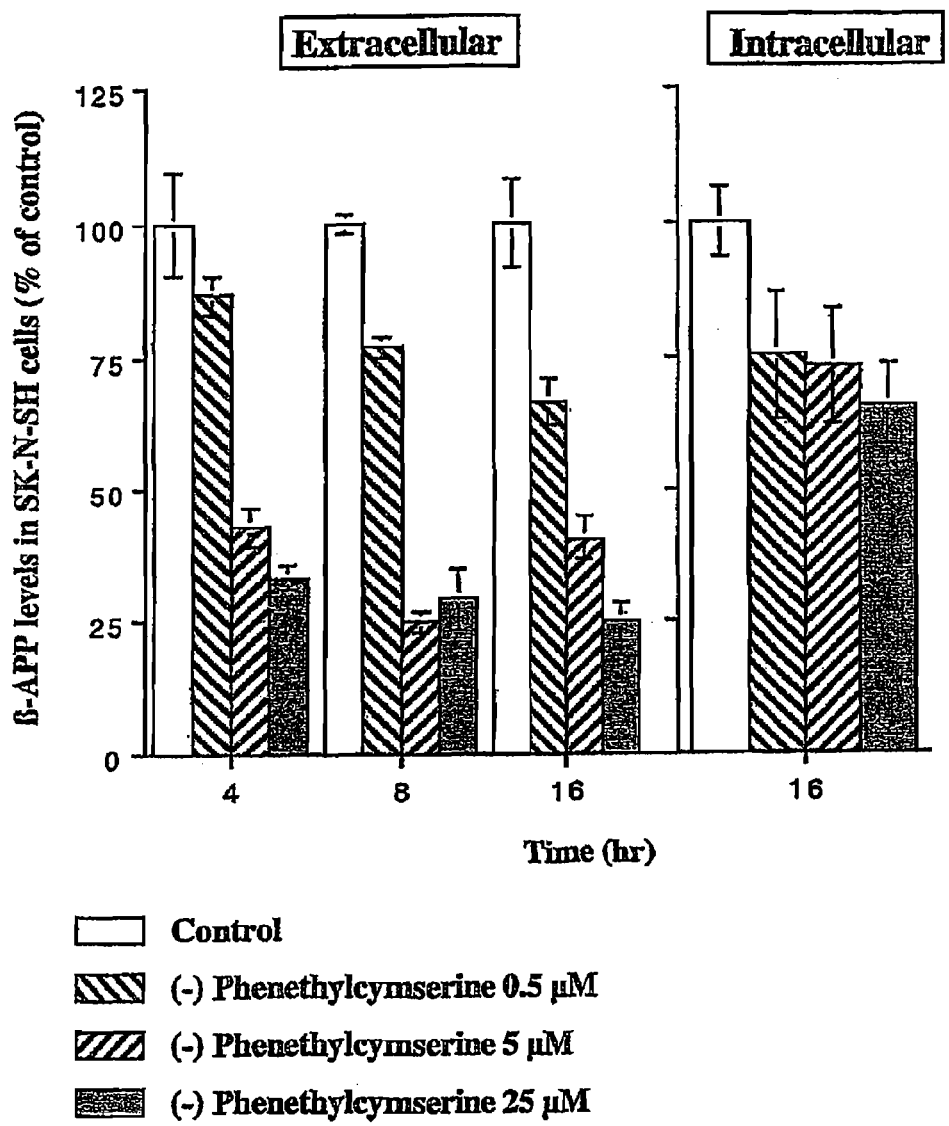
Figure 7D:
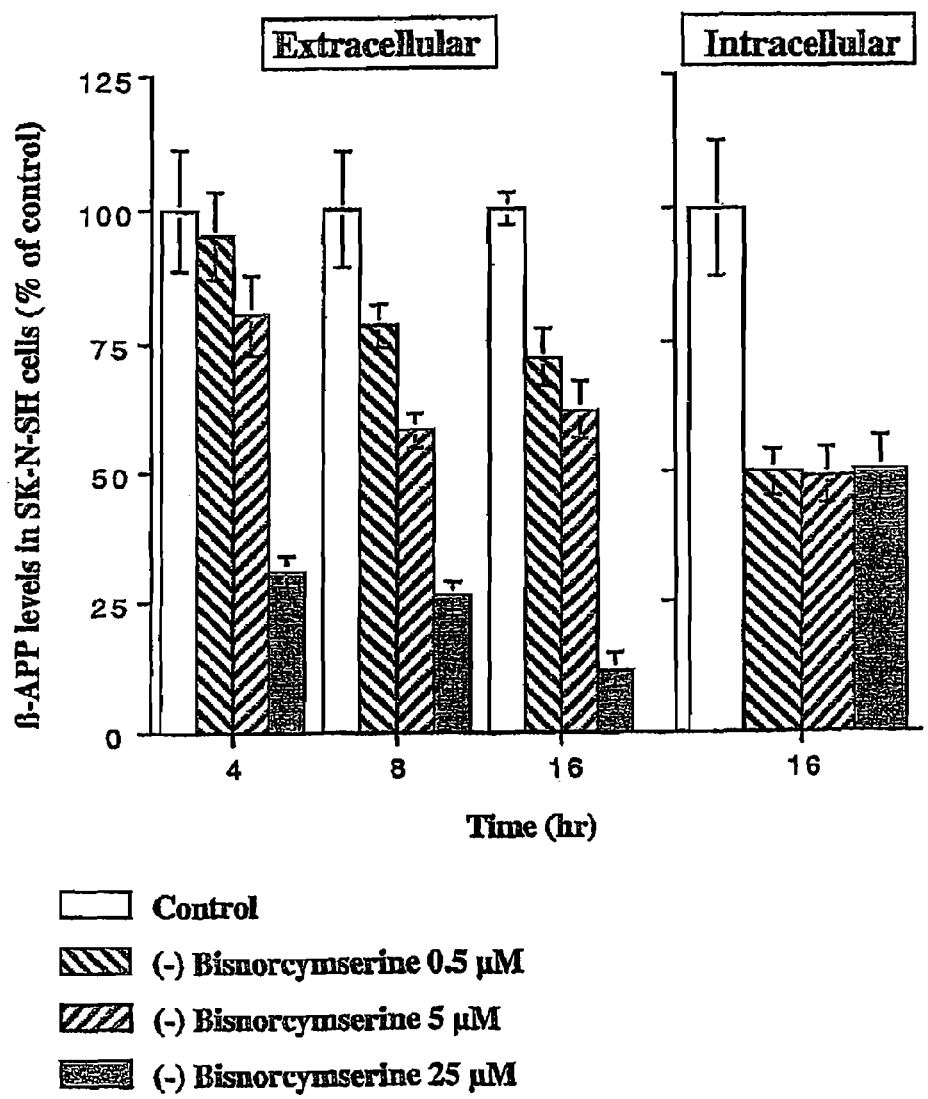

To demonstrate that the actions on βAPP protein and Aβ peptide were not restricted to enantiomers of phenserine, identical studies were undertaken with both enantiomers of cymserine (compound 46 in Table 1 for (+)-enantiomer) and with (−)-$N^1,N^8$-bisnorcymserine and (−)-$N^1$-phenethylcymserine. Similar to (−)-phenserine, the (−)-enantiomer of cymserine possessed anticholinesterase action and the (+)-enantiomer was devoid of it. As shown in FIGS. 7A and 7B, both enantiomers reduced βAPP protein levels. Similarly, $N^1,N^8$-bisnorcymserine and $N^1$-phenethylcymserine reduced βAPP protein levels (FIGS. 7C and 7D). In each case, Aβ peptide levels were also reduced, and there was no toxicity (as assessed by cell number and viability, as assessed by LDH measurement). However, at higher concentrations of $N^1,N^8$-bisnorcymserine and $N^1$-phenethylcymserine, the compounds are toxic.

Phenserine Decreases βAPP Protein Levels Through the Action of a Translational Enhancer in the APP-mRNA 5' Untranslated Region A recent report identified a 90 nt element from the 146 nt 5' untranslated region (5'UTR) of the βAPP mRNA that is able to confer a 3 fold IL-1 responsive gene expression to CAT reporter mRNAs in astrocytoma cells (Rogers et al., 1999). Interlenkin-1 was able to induce βAPP protein levels in the absence of increased βAPP mRNA synthesis. Parallel experiments with (−)-phenserine were examined for its ability to regulate βAPP protein levels in an identical manner. U373 MG astrocytoma cells were transfected with 3 μg of pSV$_2$ (APP) CAT plasmid or the parental vector pSV$_2$ CAT. Each set of transfection plates was left unstimulated or treated with 50 μM of phenserine for the experimental times listed below.

Figure 8A:
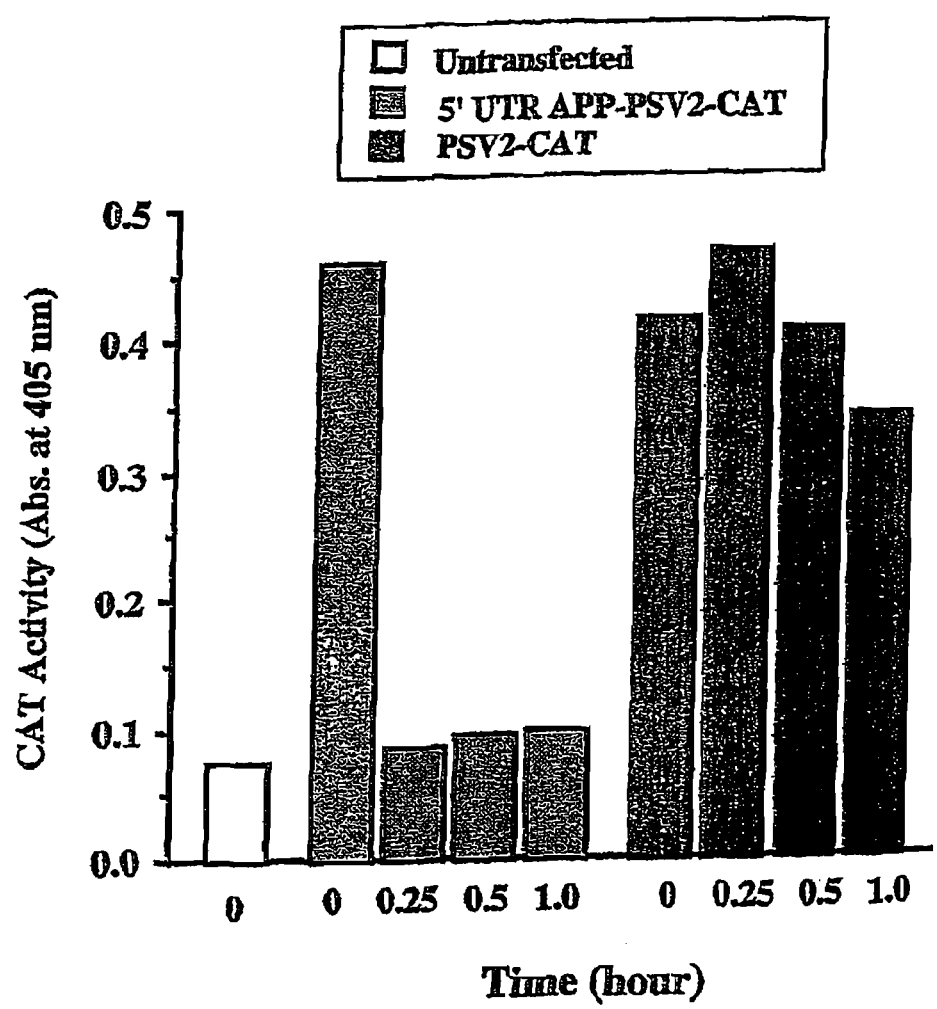
FIG. 8 shows effects of (−)-phenserine treatment on reporter gene expression in the presence and absence of the βAPP-m-RNA 5' UTR (8A), intracellular βAPP protein levels (8B), and on βAPP RNA levels (8C) in transfected U373 MG astrocytoma cells.

FIG. 8A is a representative CAT assay that shows that (−)-phenserine is able to decrease the level of APP-mRNA 5'UTR enhancement to a CAT reporter mRNA in pSV$_2$ (APP) CAT transfected astrocytoma cells. CAT activity was assessed from lysates of transfected cells treated with (−)-phenserine for 0, 0.25, 0.5 and 1 hour and 50 mg from each sample was measured in duplicate for each assay. Quantitation of the fold stimulus of CAT gene activity conferred by the 5' UTR βAPP-mRNA was measured. ELISA readings of CAT expression were measured at 405 nm. A 4-fold decrease after phenserine treatment was sustained after 1 hour. In control samples, pSV$_2$ CAT transfected cells exhibited no inhibition by (−)-phenserine at all time points, indicating that the parental vector was unresponsive to drug treatment. In other assays where the time of treatment was extended to 48 hours, only a 2-fold decrease in CAT reporter mRNA was detected with phenserine treatment. However, even in these extended assays, CAT activity in control cells remained undisturbed, indicating that the drug's effects were specific for the 5' UTR of β APP mRNA. The expression level of CAT in the control vector vs. the 5'UTR containing vector prior to (−)-phenserine treatment was similar.

(−)-Phenserine decreases the level of βAPP levels through the influence of the βAPP-mRNA 5'UTR region. Western blot analysis of βAPP protein levels was performed on lysates of transfected cells treated with (−)-phenserine for 0, 0.25, 0.5 and 1 hour (FIG. 8B). The blot was probed with anti-βAPP antibody. βAPP protein levels in transfected U373 astrocytoma cells treated with phenserine showed a similar pattern of results as with the CAT assay (FIG. 8A). The introduction of the CAT reporter constructs increased the level of βAPP over the endogenous untransfected cells, in accord with that reported by Rogers et al. (1999). However, after (−)-phenserine treatment, βAPP levels in pSV$_2$ (APP) CAT transfected astrocytomas gradually approached levels seen in untransfected and untreated cells. In contrast to these results, phenserine treatment of U373 cells did not affect βAPP mRNA levels.

Figure 8C:
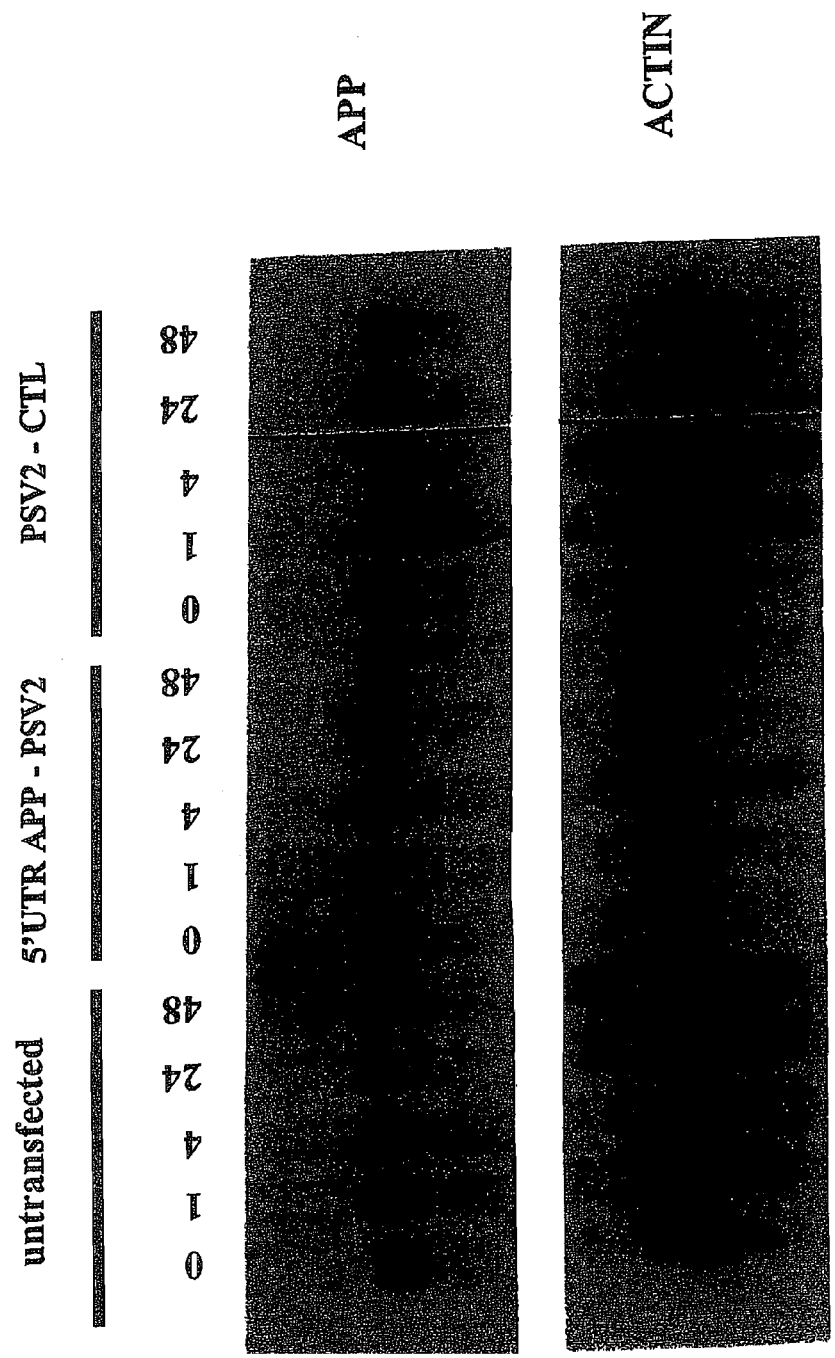

FIG. 8C is a representative northern blot of U373 cells treated with phenserine for time points up to 48 hours. Phenserine does not affect the steady state levels of βAPP-mRNA levels. Ten μg of RNA isolated from untransfected and transfected cells treated with (−)-phenserine for 0, 1, 4, 24 and 48 hours were analyzed by northern blot. Phosphoimager analysis revealed steady-state expression of βAPP-mRNA in each sample. The same filter was stripped and rehybridized with a labeled human actin probe to standardize the loading differences in individual samples. Standardization of each sample to actin mRNA expression showed consistent levels of βAPP mRNA without any major fluctuations in densitometry readings. Clearly, phenserine's action of βAPP protein is at the level of translation, as northern blot analysis of untransfected and transfected cells show little differences in levels of mRNA transcription.

In Vivo Studies-Toxicity of (−)-Phenserine Vs. (+)-Phenserine

On administration of (−)-phenserine to rodents by the i.p. route (1 ral/kg in 0.9% saline) a fine tremor is observed at a dose of 5 mg/kg. This persisted for an hour and is related to central cholinergic overdrive. Tremor together with symptoms of peripheral cholinergic overdrive (specifically, salivation and lacrimation) were seen at a dose of 7.5 mg/kg for some 3 hours. Animals were incapacitated at 20 mg/kg (N=3 per dose group), and 2 were killed when moribund. Animals (N=2) administered 20 mg/kg (+)-phenserine were without clinical symptoms and appeared normal.

Figure 9:
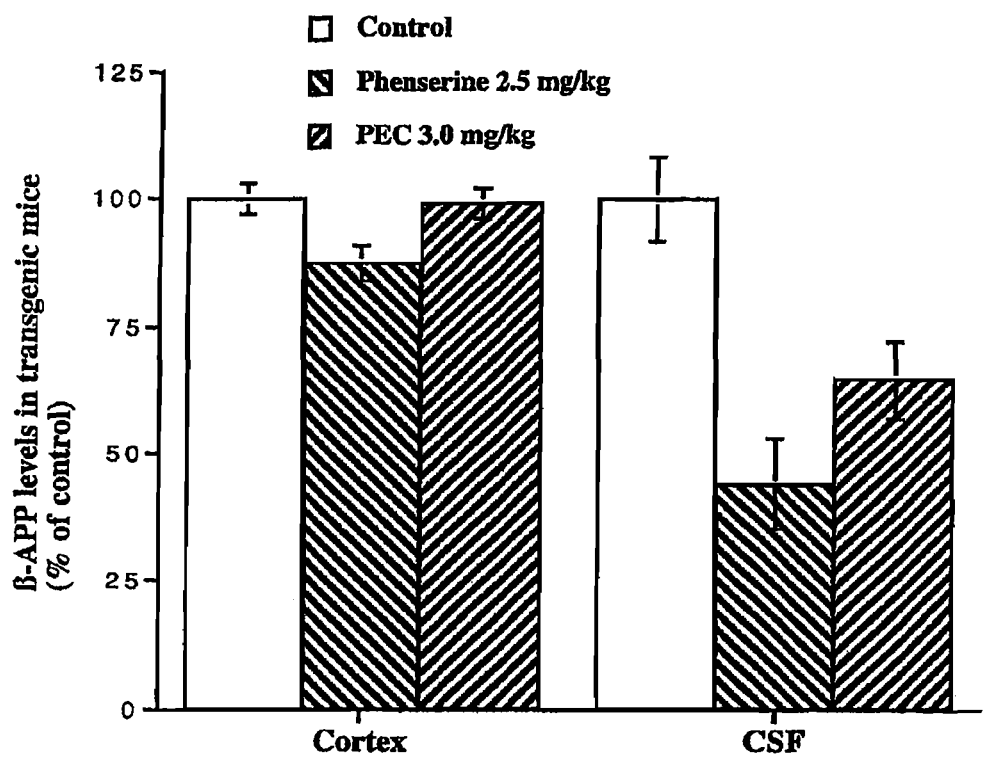
FIG. 9 shows β-APP levels in transgenic mice after administration of (−)-phenserine and (−)-phenethylcymserine.

Illustrated in FIG. 9 is the action of (−)-phenserine (2.5 mg/kg i.p., once daily for 3 weeks) on brain cortex and CSF βAPP levels in transgenic mice (N=12) that significantly overexpress βAPP as a consequence of the human Swedish βAPP mutation and mutant presenilin 1 (Borchelt et al., 1997). (−)-Phenserine significantly reduced βAPP levels by 55% in CSF and 10% in cerebral cortex. Greater reductions could be achieved, but, as previously reported, doses of >5 mg/kg produce cholinergic side effects for the (−)-enantiomer but not for the (+)-enantiomer.

Figure 10A:
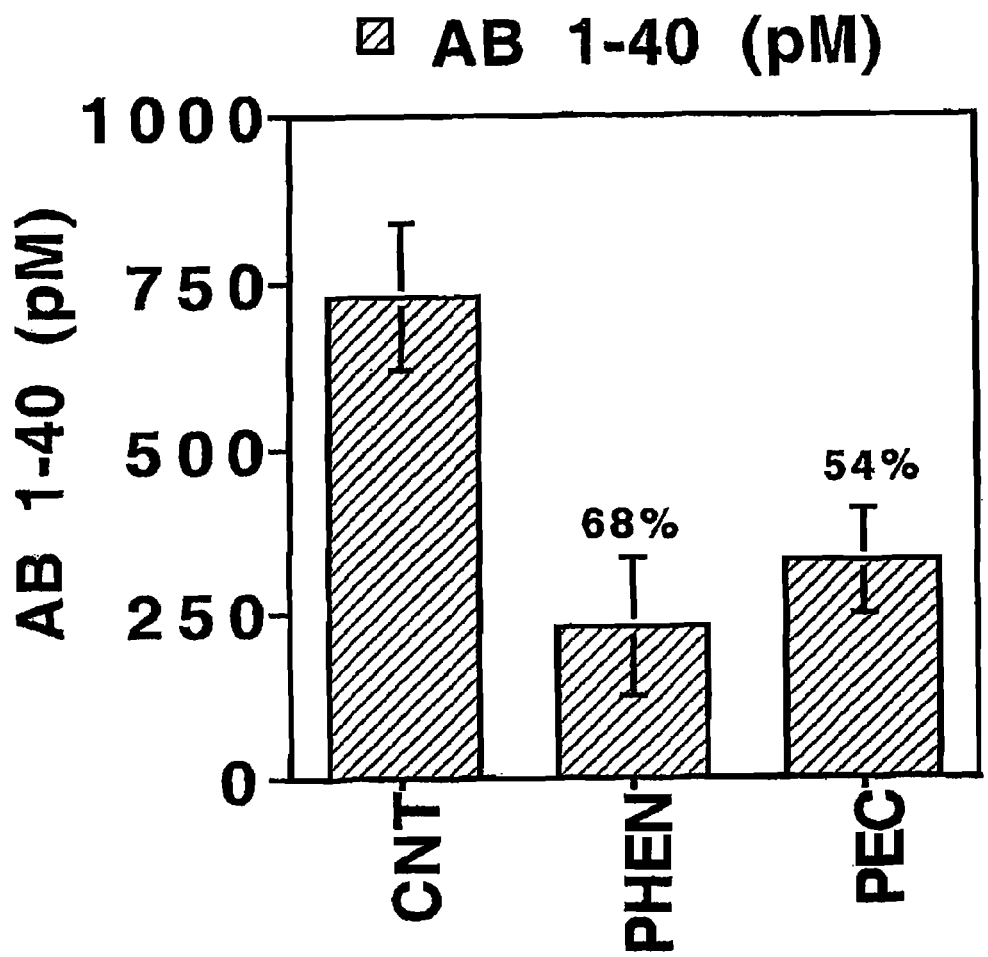
FIGS. 10A-10B show. $A\beta_{1-40}$ and $A\beta_{1-42}$ levels in transgenic mice after administration of (−)-phenserine and (−)-phenethylcymserine derived from animals described in FIG. 9.
Figure 10B:
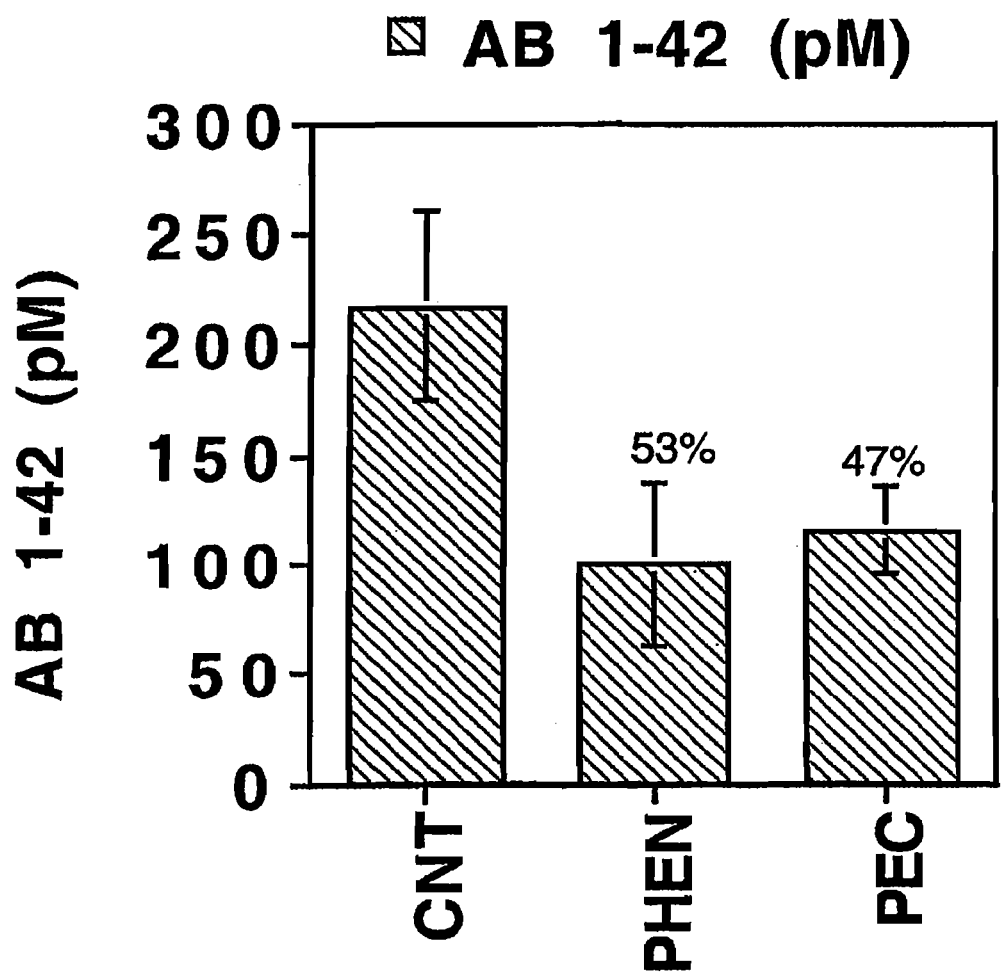

Samples of cerebral cortex from the transgenic mice then were analyzed for β amyloid peptide (Aβ) levels. Specifically, $Aβ_{1-40}$ and $Aβ_{1-42}$ levels, following formic acid extraction, were determined by ELISA assay (Suzuki et al., 1994). As shown in FIG. 10A, (−)-phenserine treatment reduced $Aβ_{1-40}$ levels by 68% (p<0.05), whereas (+N$^1$-phenethylcymserine reduced levels by 54% (p<0.05). In contrast, (−)-phenserine reduced $Aβ_{1-42}$ levels by 53% (p<0.05), compared to a 47% reduction (p<0.05) induced by (−)-N$^1$-phenethylcymserine, as shown in FIG. 10B.

Hence, even over as short a duration as three weeks in the life span of transgenic mice (generally 18 to 24 months) that overexpress βAPP and overproduce Aβ, daily phenserine and N$^1$-phenethylcymserine administration, in well tolerated doses, reduce both βAPP and Aβ levels, thereby indicating that in vitro efficacy translates to in vivo activity.

In summary, the (+)-enantiomers of this invention are the focus of the present application. They are unnatural and totally synthetic compounds. The described studies demonstrated that both (+)- and (−)-enantiomers possessed potent activity to reduce βAPP protein and total Aβ peptide levels. However, the (+)-enantiomers are devoid of anticholinesterase activity, and hence lack cholinergic action. It is the cholinergic action that is dose limiting with regard to the use of the (−)-enantiomers in vivo. The reductions in levels of βAPP protein demonstrated in tissue culture studies occurred in two different types of human neuroblastoma cell (SK-N-SH and SH-SY-5Y lines), as well as in astrocytoma cells (U 373 line). These in vitro effects translate into in vivo activity as demonstrated herein.

Translational Effect of Phenserine on APP

1. Rate of APP Synthesis $8×10^6$ SHSY-5Y cells were plated on 100 mm dishes with DMEM containing 10% FBS. After 36 hours, the culture medium was replaced with DMEM containing 0.5% FBS. The cells were incubated with low serum medium for 1 hour. Thereafter, the medium was replaced with fresh low serum medium with and without 10 μM of phenserine for 16 hours.

After treatment (16 hrs) with and without (−)-phenserine (10 μM), the cells were incubated with methionine and cystine free DMEM containing 4 mM of glutamine for 1 hour. After treatment with methionine and cystine free medium, 2 ml of $^{35}$S-labeled DMEM (100 μMCi/ml) with and without phenserine (10 μM) were added and incubated for 10 minutes. Thereafter, the labeled medium was carefully removed and the cells were suspended in lysis buffer containing with protease, inhibitors and frozen at −80° C. for use in the immunoprecipitation assay.

APP protein was immunoprecipitated from 300 μg of total protein in each sample using the polyclonal antibody O443, which recognizes a 20 amino acid sequence in the carboxy terminal of APP, and protein A/G resin overnight at 4° C. Immunoprecipitated APP was eluted from the protein AJG resin with 30 μl of elution buffer (10% beta-mercaptoethanol). The samples were loaded onto 10% trys-glycine 10 gels, and the proteins were separated at 150 V for 90 min. The gels were fixed and dried at 80° C. for 60 min. The dried gels were exposed to Phosphor Screen (PACKARD Instrument Company, Inc., Meriden, Conn.) overnight and the βAPP signals were quantitated on a phosphor imager. Phenserine significantly decreased βAPP synthesis (52% reduction) without changing TCA precipitable counts (FIG. 11A). This change in APP protein was not reflected in a change in naNA levels as phenserine did not alter levels of APP RNA (FIG. 11B).

2. Effect of Phenserine on Steady State APP Levels $3 \times 10^6$ SK-N-SH cells were plated on 60 mm dishes with DMEM containing 10% FBS. After 36 hours, cells were incubated with low serum medium for 1 hour. Thereafter, the medium was replaced with fresh low serum medium (0.5% FBS). To start the experiments, spent medium was removed and replaced with fresh medium containing 0, 0.5, 5 or 50 μM of (+)- or (−)-phenserine. The cells were incubated with and without phenserine for 16 hours. At the stated time (4, 8 and 16 hrs), 200 μl of medium was transferred from each dish for assessment of extracellular APP levels. At the end of experiments (16 hrs), the cells were lysed and collected for assessment of intracellular APP levels.

15 μL of medium samples and 15 μg of total protein from each lysed samples were loaded onto 10% trys-glycine gels, and the protein was separated at 150 V for 90 min. The gels were transferred onto polyvinylidene difluoride paper and probed with an affinity-purified anti-APP antibody (22C11), which recognizes the ectodomain of APP (residues 66-81). The APP signals were detected by chemiluminescence and exposed to film. The quantitation of the signals was determined by using a CD camera and NIH-IMAGE (version 4.0).

Figure 12A:
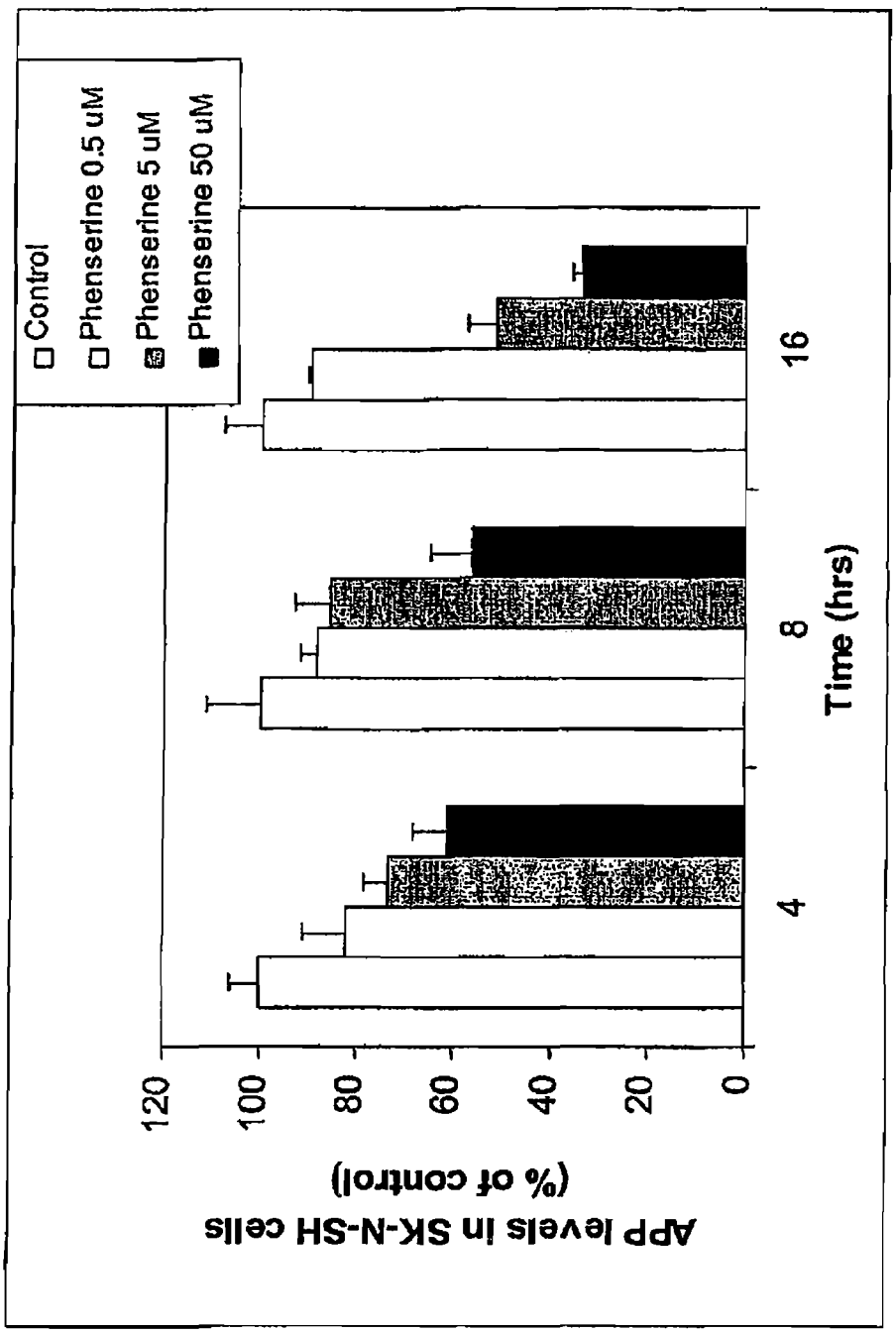
FIGS. 12A and B show the effects of (−)-phenserine on extracellular and intracellular APP levels in SK-N-SH, respectively.
Figure 12B:
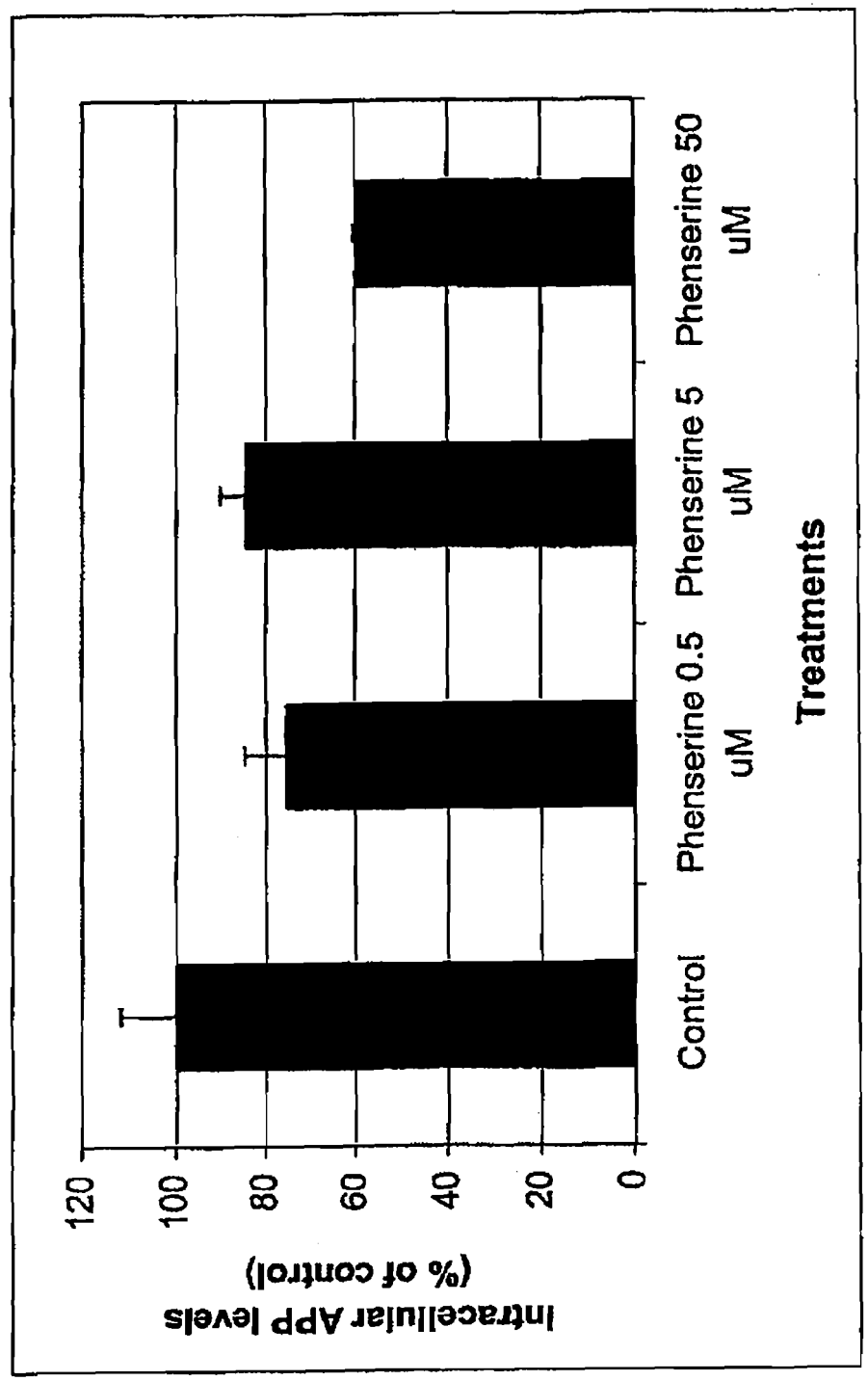

Phenserine significantly decreased steady state levels of extra- and intracellular βAPP in dose and time dependent manner (FIGS. 12A and B). Under these conditions, there was no significant toxicity as assessed by an LDH assay.

Screening for Inhibitors of APP

1. Synthesis of Compounds of Carbamate Non-Carbamate Compounds

N,N-Dimethyl-N¹-benzyl-5-methoxytryptamine (MES 9191)

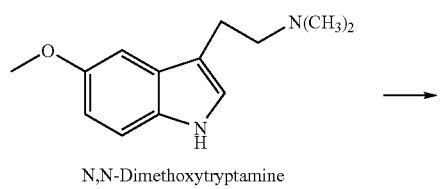

N,N-Dimethoxytryptamine

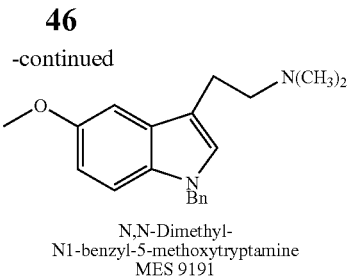

N,N-Dimethyl-
N1-benzyl-5-methoxytryptamine
MES 9191

N,N-Dimethyl-5-methoxytryptamine (654 mg, 3.0 mmol) and NaNH₂ (234 mg, 60 mmol) were added into TIM (10 ml), then benzyl bromide (513 mg, 30 mmol) was added. The mixture was refluxed under nitrogen with stirring for 2 days. Workup gave MES 9191 281 mg (30%).

(−)-(5aS)-3,5a,10-Trimethyl-1,3,4,5,5a,10a,10-heptahydro-1,3-diaza-2-one-7-5 hydroxycyclohept[2,3-b]indole (MES 9205)

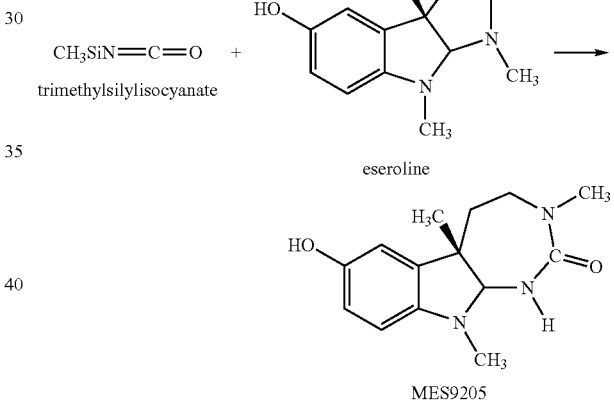

Method 1:[15]

Eseroline (180 mg, 0.82 mmol) and trimethylsilyl isocyanate (48 mg, 0.42 mmol) were dissolved in toluene (2 ml) in a sealed tube. The reaction mixture was stirred by a small magnetic bar and heated in an oil bath for 6 hours. The temperature of the oil was maintained between 100 and 110° C. After cooling to room temperature, the precipitated crystals were filtered and recrystallized from MeOH to give carbamate MES 9205 (64 mg, 30%): m.p. 174-176° C.; $[a]_D^{20}$=−154° (c=0.5, EtOH); CI-MS (NH₃) miz, 262 (M11⁻¹); ¹HNMR (CD₃OD): 6.59 (d, J=3.0 Hz, 1H, C6-H), 6.53 (m, 1H, C8-H), 6.43 (d, J=8.0 Hz, 1H, C9-H), 3,88 (s, 1H, C10a-H), 3.20 (m, 1H, C4-H'), 2.95 (m, 1H, C4-H"), 2.84 (s, 3H, N10-CH₃), 2.62 (s, 3H, N3-CH₃) 2.19 (m, 1H, C5-H'), 1.81 (m, 1H, C5-H"), 1.30 (s, 3H, C5a-CH₃). Anal (C₁₄11₁₉N₃O₂) C, H, N.

3-Methoxy-(1'-N-methylamino)-ethyl-benzene (MES 9271)

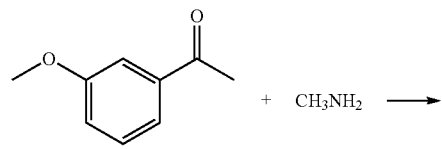

3-Methoxyacetophone

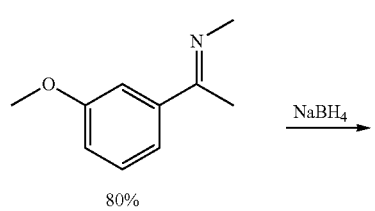

Schiff base of 3-methoxyacetophone

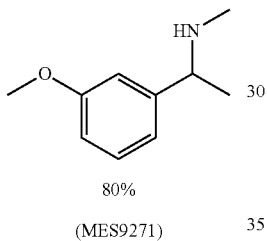

80%
(MES9271)

3-Methoxyacetophone (2 g, 0.013 mol) with methylamine (6 g,) was refluxed in ethanol for 4 h. After evaporation of solvent chromatography gave schiff base (1.7 g, 80%). The schiff base of 3-methoxyacetophone (1.25 g, 0.008 mol) was dissolved in methanol (25 ml) and reduced by sodiumborohydride (0.24 g, 0.008 mol). Workup gave MES 9271 1 g (80%).

Propionanilde (MES 9291)

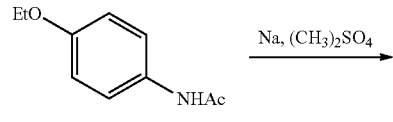

Acetylhenetidine

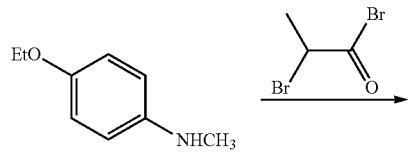

97%
N-Methylphenetidine

-continued

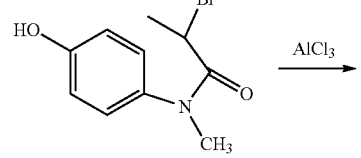

100%
Propionanilide
(MES 9291)

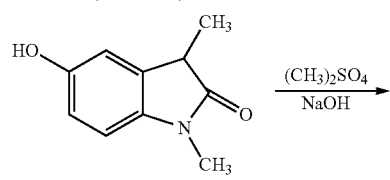

81%
5-hydroxyoxindole
(MES 9292)

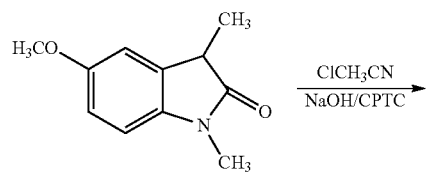

91%
5-Methoxyoxindole

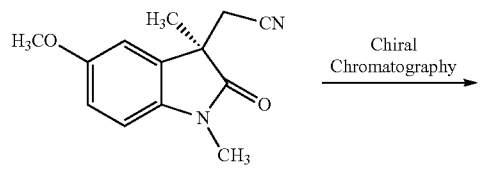

95% (ee = 70%)
(3R)-3-Cyanomethyl-5-methoxyindole

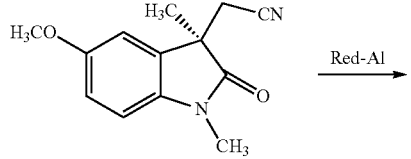

ee: about 100%
(3R)-3-Cyanomethyl-5-methoxyindole

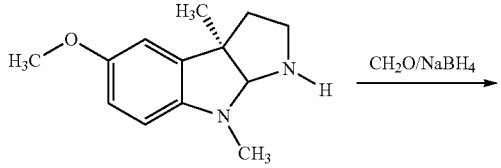

75%
(+)-N1-O-Methylnoreseroline

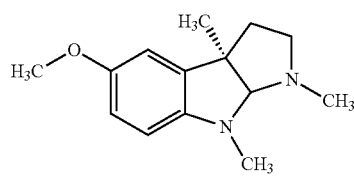

82%
(+)-O-Methyleseroline
(MES 9295)

N-Methylphenetidine (340 g, 1.85 mol) was dissolved into 750 ml of benzene and cooled to 10° C., then α-bromopropionylbromide (200 g, 0.926 mol) was rapidly added. The mixture was stirred for 1.5 h at 40° C. then washed by water and 1.5%. HCl. Evaporation gave product MES 9291 477 g (100%).

1,3-Dimethyl-5-hydroxyoxindole (MES 9292)

The propionanilde (MES 9291) (477 g, 1.85 mol) was mixed with 450 g $AlCl_3$ then heated by an oil bath to 190° C. for 1 h. After reaction the mixture was poured into ice water, the precipitate was filtered and crystallized to give product MES 9292 148 g (91%).

(+)-O-Methyleseroline (MES 9295)

The 1,3-dimethyl-5-hydroxyindole (MES 9292) was chiral alkylated by chloroacetonitrile in using the chiral catalyst CPTC to afford optical rich product, (3R)-3-cyanomethyl-5-methoxyoxindole, which then purified by chiral chromatography to give optical pure (3R)-3-cyanomethyl-5-methoxyoxindole.

Reductive cyclization of above cyano-oxindole by reducing agent red-Al gave (+)-N-1-O-methylnoreseroline which then was methylated by formaldehyde and sodiumborohydride to give IVIES 9295 in the yields as described in the scheme.

(−)-O-Tetrahydropyranyl-N-1-noreseroline (MES 9320)

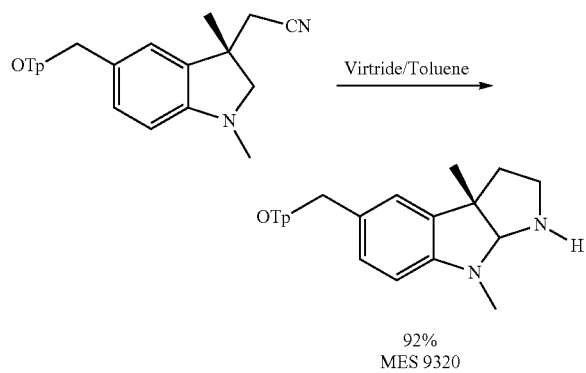

92%
MES 9320

Starting material Nitrile (120 mg, 0 4 mmol) and virtride (0.15 ml, 0 4 mmol) were dissolved in toluene. The mixture was stirred under nitrogen at room temperature for 3 h, then 5 ml of 5% NaOH was added. The toluene layer was separated out and the aqueous layer was extracted with ether (2×5 ml). The combined organic layers were washed with brine, dried over sodium sulfate, evaporated in vacuum to give MES 9320 119 mg (92.5%).

1,3-Dimethyl-3-hydroxy-5-methoxyoxindole (MES 9323)

To a 25 ml flask was added benzene (12 ml) and oxindole (95.5 ml, 0.5 mmol, then 2 ml of 50% NaOH solution were added. The mixture after standing for 12 h was extracted with ether (3×10 ml). The combined extracts were washed with brine, and dried over $MgSO_4$. After evaporation of solvent and chromatography (silica gel, petroleum ether: EtOH=3:1) gave MES 9323 62 mg (50%).

2. ELISA Assay for Identification of APP Inhibitors

An enzyme-linked immunosorbent assay was developed to detect secreted APP in SHSY5Y cells, a human neuroblastoma cell line. The purpose of the screen was to discover small molecules that inhibit APP protein synthesis in SHSY5Y cells. SHSY5Y cells were plated at $1\times10^5$ cells/well in 100 mL/well of DMEM containing 0.5% heat inactivated FBS in 96 well tissue culture treated plates (Falcon no. 35 3072). 144 MES compounds were tested at final concentrations of 20 mM, 6.7 mM, and 2.2 mM in 0.1% DMSO. Compounds were added and the plates incubated for 16 hours at 37° C./5% $CO_2$. Maxisorp plates (Nunc no. 437958) were coated overnight with 2 mg/mL capture antibody (Biosource 44-100) diluted in $Ca^{++}$ and $Mg^{++}$ free PBS. Biosource 44-100 is a mouse mAb that recognizes aa 1-100 of human APP. Plates were blocked for 30 minutes with 1 mg/mL BSA in $Ca^{++}$ and $Mg^{++}$ free PBS. Plates were washed 3× with wash buffer ($Ca^{++}$ and $Mg^{++}$ free PBS+0.01% Tween20). 50 mL of supernatants and non-cultured medium controls were transferred from culture plates to ELISA plates. Culture plates were reserved for toxicity analysis. Supernatants were incubated for 4 hours at RT on a plate shaker. After supernatant incubation, plates were washed 3×. Primary antibody (Signet Clone 6E-10 biotin) was added at 0.3125 mg/mL and incubated overnight at 4° C. The recognition site of 6E-10 is aa 1-17 of Ab. For detection, a 1:3000 dilution of horseradish peroxidase conjugated streptavidin (Endogen no. N-100) was incubated for 30 minutes. Plates were washed 3×. Enzyme activity was assessed by incubation with 100 mL/well TMB substrate solution (Moss no. TMB-US) for 20 minutes. The reaction was stopped by the addition of 100 mL/well 0.18M sulfuric acid. Optical density was read at 450 nm on Wallac Victor2 plate reader. During the first incubation, toxicity was determined using MTS assay, Cell Titer96 AQ reagent (Promega no. G5430). The background values from the non-cultured medium control were subtracted from the sample values and secreted APP levels and toxicity were expressed as % vehicle control. Of the 144 MES compounds screened, 12 inhibited secreted APP as determined by ELISA. The results are depicted in FIGS. 13A-M.

Using the experimental procedure outlined above, APP secretion and toxicity studies were performed on several other non-carbamate compounds, and the results are shown in Tables 3 and 4. The compound structures are provided in Table 2 in the application, which are identified by their MES number.

TABLE 3

| | | | APP Secretion by SH-SY-5Y Cells | | | | | |
|---|---|---|---|---|---|---|---|---|
| Number | NIH # | MES | Dose (μM) | Dose (μM) | Dose (μM) | Dose (μM) | Dose (μM) | Dose (μM) |
| | | | 0.08 | 0.25 | 0.74 | 2 | 6 | 20 |
| 6 | 594xp2 | 9191 | 100.7666667 | 101.6333333 | 99.86666667 | 100.74 | 65.3 | 64.36 |
| 15 | y-1-15 | 9199 | | | | 92.2 | 93.9 | 102.95 |

TABLE 3-continued

APP Secretion by SH-SY-5Y Cells

| Number | NIH # | MES | Dose (μM) | Dose (μM) | Dose (μM) | Dose (μM) | Dose (μM) | Dose (μM) |
|---|---|---|---|---|---|---|---|---|
| 17 | y-1-46 | 9201 | | | | 97.25 | 110.75 | 124.65 |
| 18 | y-1-48-1 (−) | 9202 | | | | 94.4 | 107.55 | 110.05 |
| 19 | y-1-48-2 (+) | 9203 | | | | 103.1 | 103.866667 | 108.36667 |
| 21 | y-1-59 | 9205 | 115.1 | 107.4 | 114.7 | 96.7333333 | 96.9 | 22.166667 |
| 22 | y-1-60 | 9206 | | | | 88.2 | 97.1 | 96.4 |
| 27 | y-1-66 | 9215 | | | | 94.55 | 108.1 | 6.2 |
| 34 | y-2-1 | 9222 | | | | 99.85 | 105.55 | 120.4 |
| 37 | y-2-13 | 9225 | | | | 110.45 | 109.2 | 59.75 |
| 38 | y-2-15 | 9226 | | | | 116.55 | 101.95 | 104.65 |
| 39 | y-2-16 | 9227 | | | | 101.15 | 99.45 | 120.5 |
| 40 | y-2-18 | 9228 | | | | 97.75 | 110.45 | 130.05 |
| 41 | y-2-19 | 9229 | | | | 111.6 | 111.4 | 125.1 |
| 42 | y-2-20 | 9230 | | | | 101.25 | 88.8 | 4.4 |
| 43 | y-2-24 | 9231 | | | | 104.9 | 133.5 | 154.2 |
| 46 | y-2-31 | 9234 | | | | 106.4 | 96.5 | 98.8 |
| 48 | y-2-33 | 9236 | | | | 105.8 | 103.2 | 101.65 |
| 49 | y-2-34 | 9237 | | | | 149.95 | 158.1 | 173.3 |
| 50 | y-2-35 | 9238 | 117.6 | 107.7 | 109.7 | 48.5666667 | 39.2333333 | 23.566667 |
| 54 | y-2-43-2 | 9242 | | | | 116.75 | 116.3 | 116.1 |
| 55 | y-2-49 | 9243 | | | | 88.95 | 95.25 | 100.55 |
| 69 | y-2-95 | 9257 | | | | 111.2 | 98.9 | 99.033333 |
| 71 | y-2-105 | 9259 | | | | 90.7 | 101.1 | 111.1 |
| 72 | y-2-106 | 9260 | | | | 93.95 | 103.2 | 101.1 |
| 78 | y-2-113 | 9266 | | | | 94.4 | 95.2 | 94.85 |
| 79 | y-2-114 | 9267 | 97.8 | 97.43333333 | 97.43333333 | 93.68 | 68.64 | 22.22 |
| 82 | y-2-130 | 9270 | | | | 95.8 | 95.9 | 98.15 |
| 83 | y-2-131 | 9271 | 96.6 | 87.95 | 92.2 | 96.1 | 89.9 | 63.825 |
| 87 | y-3-5 | 9276 | | | | 96.15 | 116.95 | 133.4 |
| 89 | y-3-15 | 9277 | | | | 98.25 | 109 | 113.6 |
| 90 | y-3-17 | 9278 | | | | 118.4 | 116.766667 | 120.63333 |
| 91 | y-3-19 | 9279 | 97.8 | 98.4 | 97 | 43.2666667 | 42.3666667 | 18.4 |
| 104 | y-3-58 | 9291 | 98.2 | 99.5 | 99.7 | 100.133333 | 96.9 | 67.8 |
| 105 | y-3-59 | 9292 | | | | 106.15 | 99.55 | 100.15 |
| 106 | y-3-60 | 9293 | | | | 97.8 | 102.75 | 94.45 |
| 107 | y-3-69 | 9294 | | | | 105.25 | 90 | 111 |
| 108 | y-3-71 | 9295 | | | | 102.6 | 95.7 | 89.35 |
| 114 | SH-281 | 9301 | | | | 108.45 | 106.1 | 111.15 |
| 115 | 140xp2 | 9302 | | | | 100.35 | 105.4 | 105.8 |
| 118 | 614xp1 | 9305 | | | | 106.2 | 102.4 | 102.2 |
| 119 | 552xp3 | 9306 | | | | 110.75 | 114.55 | 124.8 |
| 122 | piy-1-79-2 | 9309 | | | | 100 | 106.4 | 100.9 |
| 123 | 129xp3 | 9310 | | | | 104.8 | 97.85 | 98.95 |
| 124 | 637xp4 | 9311 | | | | 102.45 | 103.05 | 102.7 |
| 125 | piy-1-79-3 | 9312 | | | | 105.4 | 101.7 | 96.65 |
| 127 | piy-1-79-4 | 9314 | | | | 111.25 | 99.15 | 109.4 |
| 129 | piy-1-79-5 | 9316 | | | | 104.15 | 98.45 | 102 |
| 130 | 597xp4 | 9317 | | | | 99.8666667 | 112.266667 | 122.03333 |
| 131 | 197xF3 | 9318 | | | | 104.05 | 103.4 | 108.75 |
| 132 | 504xp2 | 9319 | | | | 108.95 | 114.1 | 112.8 |
| 133 | 338xp2 | 9320 | | | | 103.15 | 91.8 | 15.2 |
| 134 | 574xp1 | 9321 | | | | 97.95 | 98.1 | 100.5 |
| 136 | 111xp1 | 9323 | | | | 98.4 | 102.3 | 98.3 |
| 137 | 484xp2 | 9324 | | | | 110.3 | 95.9 | 99.95 |
| 143 | y-1-78-1 | 9330 | | | | 99.6 | 101.5 | 110.65 |
| 144 | y-1-78-2 | 9331 | | | | 95.45 | 102.1 | 106.7 |

TABLE 4

APP Toxicity SH-SY-5Y Cells

| Number | NIH # | MES | Dose (μM) | Dose (μM) | Dose (μM) | Dose (μM) | Dose (μM) | Dose (μM) |
|---|---|---|---|---|---|---|---|---|
| | | | 0.08 | 0.25 | 0.74 | 2 | 6 | 20 |
| 6 | 594xp2 | 9191 | 104.4666667 | 103.9 | 103.7 | 99.18 | 92.84 | 91.1 |
| 15 | y-1-15 | 9199 | | | | 100.5 | 101.65 | 101.9 |
| 17 | y-1-46 | 9201 | | | | 98.9 | 98.65 | 98.25 |
| 18 | y-1-48-1 (−) | 9202 | | | | 99.15 | 97.85 | 90.25 |
| 19 | y-1-48-2 (+) | 9203 | | | | 98.93333333 | 99.16666667 | 98.83333333 |
| 21 | y-1-59 | 9205 | 108.7 | 105.8 | 105.6 | 97.9 | 97.73333333 | 33.33333333 |
| 22 | y-1-60 | 9206 | | | | 96 | 91.85 | 76.3 |
| 27 | y-1-66 | 9215 | | | | 92.3 | 78.6 | 12.9 |
| 34 | y-2-1 | 9222 | | | | 99.25 | 100.5 | 98.9 |
| 37 | y-2-13 | 9225 | | | | 104.6333333 | 100.1 | 66.5 |

TABLE 4-continued

APP Toxicity SH-SY-5Y Cells

| Number | NIH # | MES | Dose (μM) | Dose (μM) | Dose (μM) | Dose (μM) | Dose (μM) | Dose (μM) |
|---|---|---|---|---|---|---|---|---|
| 38 | y-2-15 | 9226 | | | | 106.3666667 | 99.7 | 97.9 |
| 39 | y-2-16 | 9227 | | | | 103.6666667 | 99.26666667 | 96.06666667 |
| 40 | y-2-18 | 9228 | | | | 102.7666667 | 97.6 | 95.4 |
| 41 | y-2-19 | 9229 | | | | 99.96666667 | 96.06666667 | 91.46666667 |
| 42 | y-2-20 | 9230 | | | | 100.8333333 | 86.13333333 | 13.83333333 |
| 43 | y-2-24 | 9231 | | | | 95.7 | 90.73333333 | 85.86666667 |
| 46 | y-2-31 | 9234 | | | | 102.55 | 99.75 | 99.3 |
| 48 | y-2-33 | 9236 | | | | 97.6 | 101 | 100.05 |
| 49 | y-2-34 | 9237 | | | | 96.55 | 98.35 | 99.4 |
| 50 | y-2-35 | 9238 | 101.8 | 103.8 | 106.4 | 41.8 | 40.46666667 | 31.63333333 |
| 54 | y-2-43-2 | 9242 | | | | 94.2 | 89.8 | 80.95 |
| 55 | y-2-49 | 9243 | | | | 99.1 | 98.4 | 99 |
| 69 | y-2-95 | 9257 | | | | 100.5333333 | 98.76666667 | 100 |
| 71 | y-2-105 | 9259 | | | | 102.65 | 102.9 | 98.75 |
| 72 | y-2-106 | 9260 | | | | 99.8 | 97.2 | 98.95 |
| 78 | y-2-113 | 9266 | | | | 96.55 | 97.75 | 94.15 |
| 79 | y-2-114 | 9267 | 101.5333333 | 102 | 101.9333333 | 97.98 | 96.72 | 15.52 |
| 82 | y-2-130 | 9270 | | | | 99.4 | 101.1 | 100.4 |
| 83 | y-2-131 | 9271 | 103.55 | 103.45 | 103.1 | 99 | 99.475 | 94.1 |
| 87 | y-3-5 | 9276 | | | | 92.85 | 93.5 | 90.65 |
| 89 | y-3-15 | 9277 | | | | 98.25 | 98.3 | 91.1 |
| 90 | y-3-17 | 9278 | | | | 97.63333333 | 98.4 | 96.33333333 |
| 91 | y-3-19 | 9279 | 102.9 | 101.1 | 100.1 | 68.63333333 | 46.66666667 | 38.63333333 |
| 104 | y-3-58 | 9291 | 99.1 | 100.5 | 97.1 | 102.3666667 | 99.86666667 | 99 |
| 105 | y-3-59 | 9292 | | | | 102.85 | 103.75 | 104.9 |
| 106 | y-3-60 | 9293 | | | | 100.8 | 99.85 | 101.95 |
| 107 | y-3-69 | 9294 | | | | 99.9 | 98.3 | 100.2 |
| 108 | y-3-71 | 9295 | | | | 101.15 | 100.4 | 99.85 |
| 114 | SH-281 | 9301 | | | | 99.15 | 97.35 | 95.9 |
| 115 | 140xp2 | 9302 | | | | 100.7 | 101.2 | 99.05 |
| 118 | 614xp1 | 9305 | | | | 95.8 | 96.73333333 | 94.83333333 |
| 119 | 552xp3 | 9306 | | | | 102.3 | 101.45 | 106 |
| 122 | piy-1-79-2 | 9309 | | | | 100.85 | 98.6 | 101.1 |
| 123 | 129xp3 | 9310 | | | | 101.85 | 99.9 | 97.7 |
| 124 | 637xp4 | 9311 | | | | 101.1 | 101.25 | 99.55 |
| 125 | piy-1-79-3 | 9312 | | | | 99.95 | 103.85 | 106.95 |
| 127 | piy-1-79-4 | 9314 | | | | 100.15 | 100.85 | 100.6 |
| 129 | piy-1-79-5 | 9316 | | | | 99.15 | 98.05 | 98.75 |
| 130 | 597xp4 | 9317 | | | | 97.26666667 | 97.23333333 | 93.5 |
| 131 | 197xF3 | 9318 | | | | 96.2 | 96.45 | 96.05 |
| 132 | 504xp2 | 9319 | | | | 99.8 | 101.05 | 102.7 |
| 133 | 338xp2 | 9320 | | | | 92 | 84 | 28 |
| 134 | 574xp1 | 9321 | | | | 99.9 | 101.15 | 99.45 |
| 136 | 111xp1 | 9323 | | | | 97.2 | 100.1 | 101.15 |
| 137 | 484xp2 | 9324 | | | | 102.15 | 100.4 | 98.65 |
| 143 | y-1-78-1 | 9330 | | | | 99.05 | 98.45 | 97.95 |
| 144 | y-1-78-2 | 9331 | | | | 100.45 | 99.9 | 98.95 |

2. Effect of Phenserine Analogues on Steady State APP Levels $3 \times 10^6$ SK-N-SH cells were plated on 60 mm dishes with DMEM containing 10% FBS. After 36 hours, cells were incubated with low serum medium for 1 hour. Thereafter, the medium was replaced with fresh low serum medium (0.5% FBS). To start the experiments, spent medium was removed and replaced with fresh medium with and without phenserine analogues. The cells were incubated with and without compounds for 16 hours. At the end of experiments (16 hrs), 200 ml of medium and the cells were lysed and collected for assessment of intracellular APP levels.

20 ml of medium samples and 15 mg of total protein from each lysed samples were loaded onto 10% trys-glycine gels, and the protein was separated at 150 V for 90 min. The gels were transferred onto polyvinylidene difluoride paper and probed with an affinity-purified anti-APP antibody (22C11), which recognizes the ectodomain of APP (residues 66-81). The APP signals were detected by chemiluminescence. The quantitation of blots was undertaken by using a CD camera and NIH-IMAGE (version 4.0).

Figure 14:
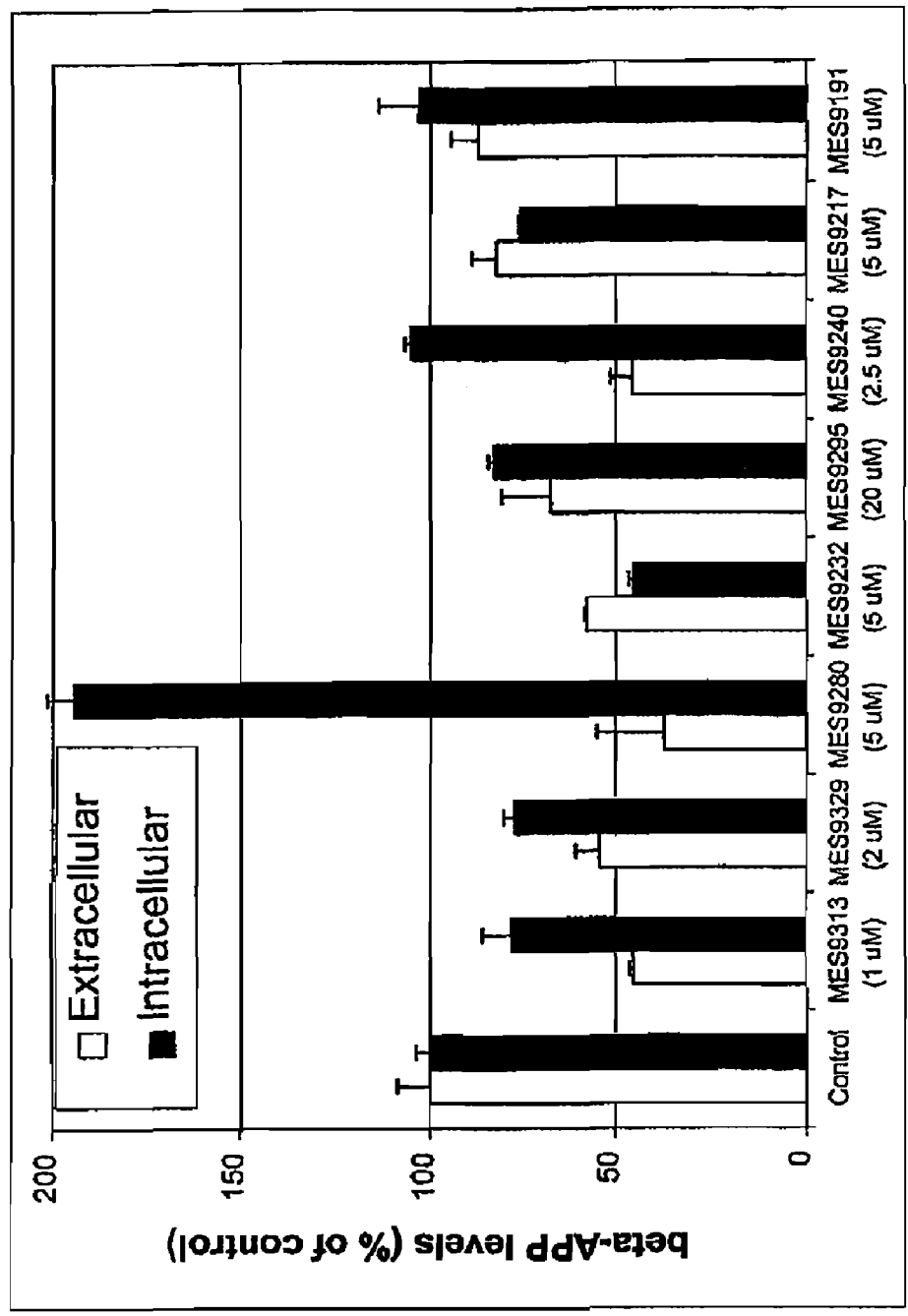
FIG. 14 shows the effects of several compounds of the invention on extra- and intracellular APP levels in SH-SY5Y cells.

Several of the compounds of the invention decreased the extra- and intracellular APP levels. A few compounds, which have no carbamate group within the molecule, did not show significant reductions of intracellular APP levels, but did reduce extracellular APP levels. The treatment with 5 mM of MES9280 showed some toxicity (increase of LDH levels and morphological change). The results are shown in FIG. 14.

3. Effect of Phenserine Analogues on APP Translation $3 \times 10^6$ SHSY-5Y cells were plated on 60 mm dishes with DMBM containing 10% FBS. After 36 hours, the culture medium was replaced with DMEM containing 0.5% PBS. The cells were incubated with low serum medium for 1 hour, thereafter, the medium was replaced with fresh low serum medium with and without phenserine analogues for 16 hours.

After treatments (16 hrs) with and without the compounds of the invention, the cells were incubated with methionine and cystine free DMEM containing 4 mM of glutamine for 1 hr. After treatment with methionine and cystine free medium, 1 ml of $^{35}$S-labeled DMEM (100 μCi/ml) with and without the compounds were added and incubated for 10 minutes. Thereafter, the labeled medium were carefully removed and the cells were suspended within lysis buffer containing with protease inhibitors and frozen at −80° C. until immunoprecipitation assay.

APP were immunoprecipitated from 200 ug of total protein in each samples with polyclonal antibody O443, which recognizes 20 aminoacids sequences of APP carboxy terminal, and protein A/G resin for overnight at 4 C. Immunoprecipitated APP were eluted from protein A/G resin with 30 μl of elution buffer (10% beta-mercaptoethanol). The samples were loaded onto 10% trys-glycinegels, and the protein were separated at 150 V for 90 min. The gels were fixed with fixing buffer and dried at 80 C for 60 min. The dried gels were exposed onto Phosphor Screen (PACKARD, Instrument Company, Inc., Meriden, Conn.) for overnight and the APP signals were quantitated on phosphor image.

Figure 15A:
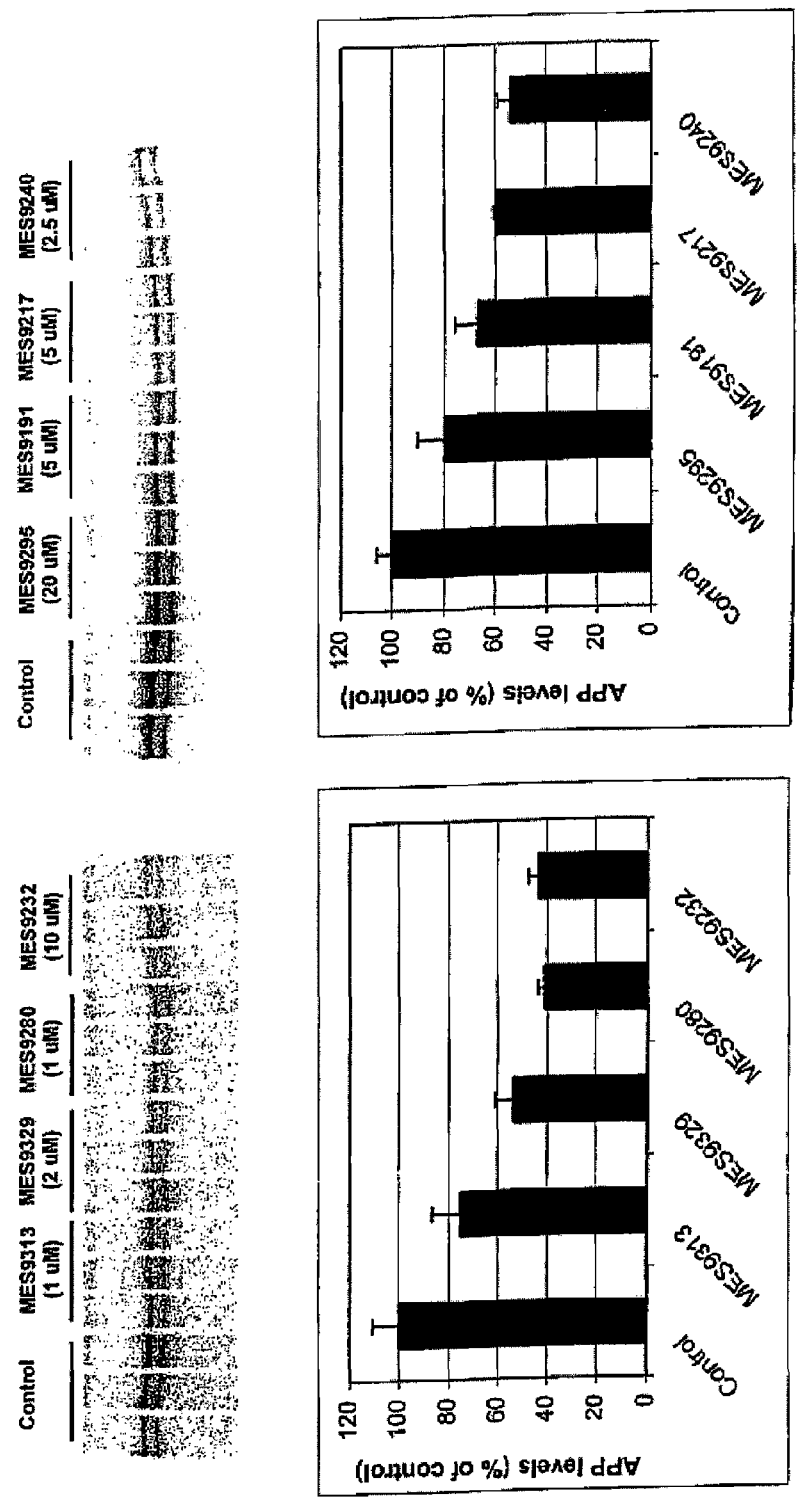
FIG. 15A shows the translational regulation by compounds (rate of APP Synthesis) in SH-SY5Y cells using several compounds of the invention.
Figure 15B:
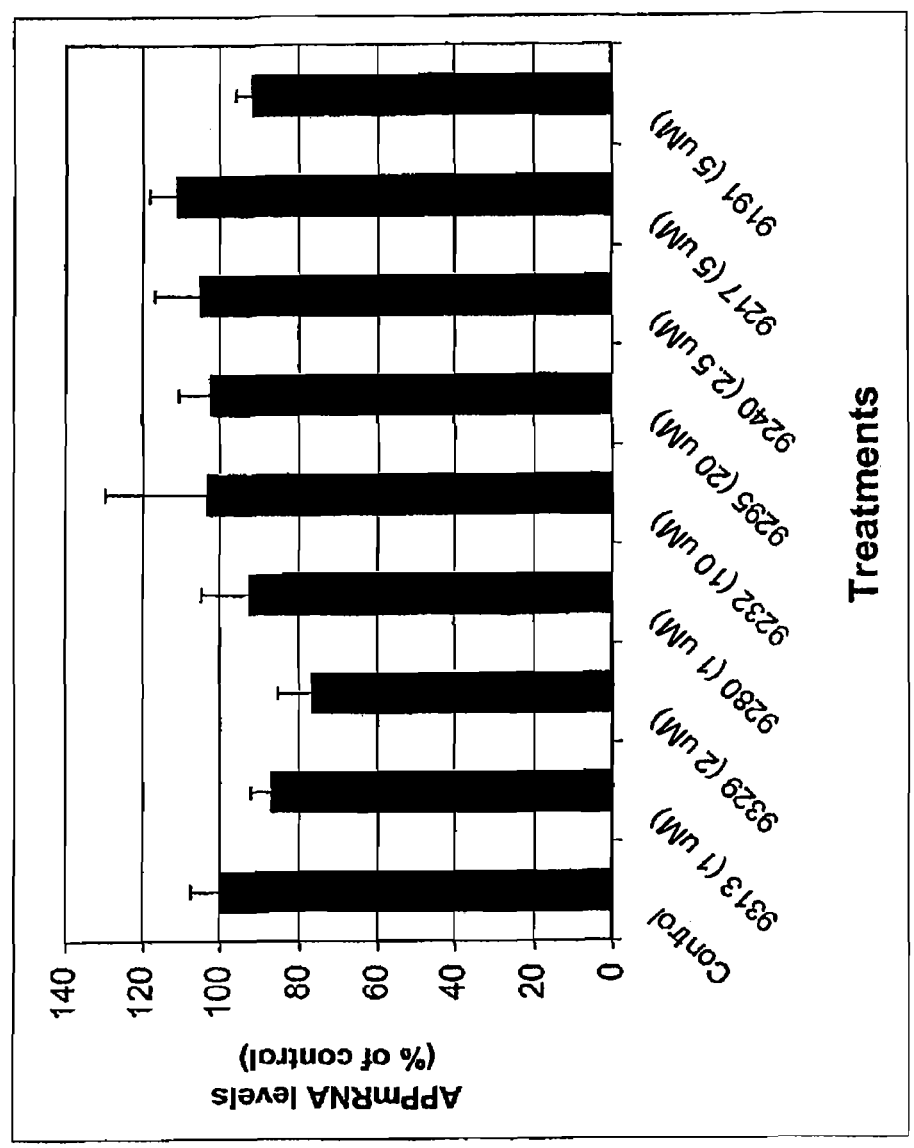
FIG. 15B shows the effects of several compounds of the invention on the steady state APP mRNA levels in SH-SY5Y cells.

The levels of newly synthesized βPP were normalized by TCA precipitable counts. Several phenserine analogues significantly decreased βAPP synthesis without changing TCA precipitable counts (FIG. 15A). In addition, there was no change in APP mRNA levels (FIG. 15B).

REFERENCES

Adem A, Mattsson M E K, Nordberg A, Pahhnan S (1987) Muscarinic receptors in human SH-SY5Y neuroblastoma cell line: regulation by phorbol ester and retinoic acicl5 induced differentiation. Develop Brain Res 33:235-242.

Akijama H, Barger S, Barnum S, et al., (2000) Inflammation and Alzheimer's disease. Neurobiol. Aging 21:383-421.

Becker R E., Moriearty P., Unni L. The second generation of cholinesterase inhibitors: clinical and pharmacological effects. In, The Cholinergic Basis for Alzheimer Therapy (ed., Becker R E., Giacobini, E) Birkhauser, Boston, 263-296, 1991.

Bhasker C R, Burgiel G, Neupert B, Emery-Goodman A, Kuhn L C, May B K (1993) 15 The putative iron-responsive element in the human erythroid 5-arninolevalinate synthase mRNA mediates translational control. J Biol Chem 268(17):12699-1270.

Borchelt D R, Ratovitski T, van Lare J, Lee M K, Gonzales V, Jenkins N A, Copeland N G, Price D L, Sisodia S S. Accelerated amyloid deposition in the brains of transgenic mice coexpressing mutant presenilin 1 and amyloid precursor proteins. Neuron 1997 October; 19(4):939-45.

Breitner J C S (1997) Inflammatory processes and anti-inflammatory drugs in Alzheimer's disease: a current appraisal. Neurobiol Aging 17(5): 789-794.

Bronfman. F C, Fernandez T E L, Inestrosa N C (1996) Amyloid precursor protein fragment and acetylcholinesterase increase with cell confluence and differentiation in a neuronal cell line. Exp Cell Res 229:93-99.

Brossi A, Pei X-F, Greig N H (1996) Phenserine, a novel anticholinesterase related to physostigmine: total synthesis, and biological properties. Austr J Chem 49:171-190.

Buxbaum J D, Gandy S E, Cicchetti P, Ehrlich M E, Czernik A J, Fracasso R P, Ramabhadran T V, Unterbeck A J, Greengard P (1990) Processing of Alzheimer beta/A4 amyloid precursor protein: modulation by agents that regulate protein phosphorylation. Proc Natl Acad Sci USA 1990 87(15):6003-6006.

Buxbaum J D, Oishi M, Chen H I, Pinkas-Kramarski R, Jaffe E A, Gandy S E, Greengard P (1992) Cholinergic agonists and interleukin 1 regulate processing and secretion of the Alzheimer beta/A4 amyloid protein precursor. Proc Natl Acad Sci USA 89(21):10075-10078.

Buxbaum J D, Ruefli A A, Parker C A, Cypess A M, Greengard P (1994) Calcium regulates processing of the Alzheimer amyloid protein precursor in a protein kinase C-independent manner Proc Natl Acad Sci USA 91:4489-4493.

Caputi A, Barindelli S, Pastorino L, Cimino M, Buxbaum J D, Cattabeni F, Di Luca M (1997) Increased secretion of the amino-terminal fragment of amyloid precursor protein in brains of rats with a constitutive up-regulation of protein kinase C. J Neurochem 68(6):2523-2529.

Checker, F (1995) Processing of B-amyloid precursor protein and its regulation in Alzheimer's disease. J Neurochem. 65:1431-1444.

Desdouits F, Busxbaum J D, Desdouits-Magnen, Nairn A C, Greengard P (1996) Amyloid b peptide formation in cell-free preparations: regulation by protein kinase C, calmodulin and calcineurin. J Biol Chem 271(40):24670-24674.

Desdouits-Magnen J, Desdouits F, Takeda S, Syu L, Saltiel A R, Buxbaum J D, Czernik A J, Nairn A C, Greengard P (1998) Regulation of secretion of Alzheimer amyloid precursor protein by the mitogen-activated protein kinase cascade. J Neurochem 70(2):524-530.

Dyrks T, Monning U, Beyreuther K, Turner J (1994) Amyloid precursor protein secretion and bA4 amyloid generation are not mutually exclusive. FEBS Lett 349:210-214.

Eisenstein R S, Tuazon P T, Schalinske K L, Anderson S A, Traugh J A (1993) Iron-responsive element-binding protein. Phosphorylation by protein kinase C. J Biol Chem 268(36):27363-27370.

Felder C C, Ma A L, Briley E M, Axelrod J (1993) Muscarinic acetylcholine receptor subtypes associated with release of Alzheimer amyloid precursor derivatives activate multiple signal transduction pathways. Ann N Y Acad Sci 695:15-18.

Funato H, Yoshimura M, Yamazaki T, Sato T C, Ito Y, Yokofujita J, Okeda R, Ihara Y (1998) Astrocytes containing amyloid-protein (A)-positive granules are associated with A40-positive diffuse plaques in the aged human brain. Am J Path 152:983-992.

Greig N H, Pei X-F, Soncrant T, Ingram D, Brossi A (1995) Phenserine and ring-C hetero-analogues: drug candidates for the treatment of Alzheimer's disease. Med Chem Rev 15:3-31.

Haroutunian V, Greig N H, Pei X F, Utsuki T, Gluck R, Acevedo L D, Davis K L, Wallace W C (1997) Pharmacological modulation of Alzheimer's beta-amyloid precursor protein levels in the CSF of rats with forebrain cholinergic system lesions. Brain Res Mol Brain Res 46(1-2):161-168.

Hentze M W, Kubn L C (1996) Molecular control of vertebrate iron metabolism: mRNA-based regulatory circuits operated by iron, nitric oxide, and oxidative stress. Proc Natl Acad Sci USA 93:8175-8182.

Hung A Y, Selkoe D J (1994) Selective ectodomain phosphorylation and regulated cleavage of beta-amyloid precursor protein. EMBO J. 13(3):534-542.

Hussaain, I, Powell D, Howlett D R, Tew D G, Week T D, Chapman. C, Golger I S, Murphy K E, Southan C D, Ryan D M, Smith T S, Simmons D L, Walsh F S, Dingwall C, Christie, G (1999) Identification of a novel aspartic protease (Asp 2) as beta-secretase. Mol Cell Neurosci 14: 419-427.

Jacobsen J S, Spruyt M A, Brown A M, Sahasrabudhe S R, Blume A J, Vitek M P, Muenkel H A, Sonnenberg-Reines J (1994) The release of Alzheimer's disease beta amyloid peptide is reduced by phorbol treatment. J Biol Chem 269(11):8376-8382.

Kim H-Y, LaVaute T, Iwai K, Klausner R D, Rounault T A (1996) Identification of a conserved and functional iron-responsive element in the 5'-untranslated region of mammalian mitochondrial aconitase. J Biol Chem 271(39): 24226-24230.

Koike H, Seki H, Kouchi Z, Ito M, Kinouchi T, Tomioka S, Sorimachi H, Saido T C, 25 Maruyama K, Suzuki K, Ishiura S (1999) Thimet oligopeptidase cleaves the full-length Alzheimer amyloid precursor protein at a beta-secretase cleavage site in COS cells. J Biochem 126: 235-242.

Lahiri D K, Farlow M R, Numberger J I Jr, Greig N H (1997) Effects of cholinesterase inhibitors on the secretion of beta-amyloid precursor protein in cell cultures. Arm N Y Acad Sci 26; 826:416-421.

Lahiri D K, Farlow M R, Sambamurti K (1998) The secretion of amyloid beta-peptide is inhibited in tacrine-treated human neuroblastoma cells. Mol. Brain. Res. 62: 131:140.

Leblanc A C, Koutroumanis M, Goodyer C G (1998) Protein kinase C activation increases release of secreted amyloid precursor protein without decreasing Ab production in human primary neuron cultures. J Neurosci 18(8):2907-2913.

Leli U, Cataldo A, Shea T B, Nixon R A, Hauser G (1992) Distinct mechanism of differentiation of SH-SY5Y neuroblastoma cells by protein kinase C activators and inhibitors. J Neurochem 58(4): 1191-1198.

Melefors O, Goossen B, Johansson H E, Stripecke R, Gray N K, Hentze M W (1993) Translational control of 5-aminolevulinate synthase mRNA by iron-responsive elements in erythroid cells. J Biol Chem 268(8):5974-5978.

Nitsch R M, Growdon J H, Farber, S A, Deng M, Wurtman R J (1994) Regulation of APP processing by first messengers. In: Alzheimer Disease: Therapeutic Strategies (Giacobini E, Becker R, eds), pp 54-61. Boston:Birkhauser.

Nitsch R M, Slack B E, Wurtman. R J, Growdon J H. (1992) Release of Alzheimer amyloid precursor derivatives stimulated by activation of muscarinic acetylcholine receptors. Science 258:304-307.

Patel N, Spangler E L, Greig N H, Yu Q S, Ingram D K, Meyer R C (1998) Phenserine, a novel acetylcholinesterase inhibitor, attenuates impaired learning of rats in a 14-unit T-maze induced by blockade of the N-methyl-D-aspartate receptor. Neuroreport 9(1):171-176.

Rogers J T, Leiter L, Mcphee J, Cahill C M, Zhan S S, Potter H, Nilsson L N (1999) Translation of the Alzheimer amyloid precursor protein mRNA is upregulated by interleukin 1 through 5'-untranslated region sequences. J Biol Chem 274: 6421-6431.

Roberson, M R, Harrell L E (1997) Cholinergic activity and amyloid precursor protein metabolism. Brain Res Rev 25:50-69.

Savage M J, Trusko S P, Howland D S, Pinsker L R, Mistretta S, Reaume A G, Greenberg B D, Siman R, Scott R W (1998) Turnover of amyloid b-protein in mouse brain and acute reduction of its level by phorbol ester. J Neurosci 18(5):1743-1752.

Schalinske K L, Chen O S, Eisenstein R S (1998) Iron differentially stimulates translation 15 of mitochondrial aconitase and ferritin mRNAs in mammalian cells Implications for iron regulatory proteins as regulators of mitochondrial citrate utilization. J Biol Chem 273(6):3740-3746.

Selkoe D J (1997) Alzheimer's disease: genotypes, phenotypes, and treatments. Science 1997 275(5300):630-631.

Sinha S, Anderson J P, Barbour R, Basi G S, Caccavello R, Davis D, Doan M, Dovey H Y, Frigon N, Hong J, Jacobson-Croak K, Jewett N, Keim P, Knops J, Lieberburg I, Power M, Tan H, Tatsuno G, Tung J, Schenk D, Seubert P, Suomensaari S M, Wang S W, Walker D, Zhao J, McConlogue L, John V (1999) Purification and cloning of amyloid precursor protein beta-secretase from human brain. Nature 402: 537-540.

Suzuki N, Cheung T, Cai X., Odaka A., Eckman C., Golde T, Younkin, S G (1994) An increased percentage of long amyloid-beta protein secreted by familial amyloid-beta protein-precursor (beta-APP (717)) mutants. Science 264: 1336-1340.

Vassar R, Bennett B D, Babu-Khan S, Kahn S, Mendiaz E A, Denis P, Teplow D B, Ross S, Amarante P, Loeloff R, Luo Y, Fisher S, Fuller L, Edenson S, Lile J, JarosirAi M A, Biere A L, Curran E, Burgess T, Louis J C, Collins F, Treanor J, Rogers G, Citron M (1999) beta-secretase cleavage of Alzheimer's amyloid precursor protein by the transmembrane aspartic protease BACE. Science 286: 735-741.

Waskiewics A J, Cooper J A (1995) Mitogen and stress response pathways: MAP kinase cascades and phosphatase regulation in mammals and yeast. Curr Opin Cell Biol 7:798-805.

Wisniewski H M, Wegiel J, Kotula L (1996) Review. David Oppenheimer Memorial Lecture 1995: Some neuropathological aspects of Alzheimer's disease and its relevance to other disciplines. Neuropathol Appl Neurobiol 22(1):3-11.

Yan R Q, Bienkowski M J, Shuck M E, Miao H Y, Tory M C, Pauley A M, Brashler J R, Stratman N C, Mathews W R, Buhl A E, Carter D B, Tomasselli A G, Parodi L A, Heinrikson R L, Gurney M E (1999) Membrane-anchored aspartyl protease with Alzheimer's disease beta-secretase activity. Nature 402: 533-537.

Yu, Q S, Brossi A (1988) Practical Synthesis of Unnatural (+)-Physostigmine and 25 Carbamate Analogues. Heterocycles 27: 745-751.

Xu H, Greengard P, Gandy S (1995) Regulated formation of Golgi secretory vesicles containing Alzheimer beta-amyloid precursor protein. J Biol Chem 270(40):23243-23245.

References for FIG. 1

1. Qian-sheng Yu, Arnold Brossi. Practical Synthesis of Unnatural (+)-Physostigmine and Carbamate Analogues. *Heterocycles*, 1988, 27, 745-750.
2. Xue-Feng Pei, Nigel H. Greig, Sheng Bi, Arnold Brossi and V. Toom Tnhibition of 10Human Acetylcholinesterase by Unnatural (+)-(3aR)-$N^1$-Norphysostigmine and Arylcarbamate. *Medicinal Chemistry Research*, 1995, 5, 265-270.
3. Qian-sheng Yu, Xue-Feng Pei, Harold W. Holloway, Nigel H. Greig, Arnold Brossi. Total Synthesis and Anticholinsterase Activities of (3aS)-N(8)-Norphysostigmine, (3aS)-N(8)-Norphenserine, Their Antipodal Isomers, and Other N(8)-Substituted Analogues. *J. Med. Chem.*, 1997, 40, 2895-2901.
4. Qian-sheng Yu, Nigel H. Greig, Harold W. Holloway, Arnold Brossi. Syntheses and Anticholinesterase Activities of (3aS)-$N^1$,1\e-Bisnorphenserine, (3aS)-$N^1$,$N^8$-Bisnorphysostigmine, Their Antipodal Isomers and Other Potential Metabolites of Phenserine. *J. Med. Chem.*, 1998, 41, 2371-2379.
5. Xue-Feng Pei, Qian-sheng Yu, Harold W. Holloway, Arnold Brossi, Nigel H. Greig, Syntheses and Biological Evaluation of Ring-C Opened Analogues of The Cholinesterase Physostigmine, Phenserine and Cymserine. *Med. Chem. Res.*, 1999, 9, 50-60.

References for FIG. 2

1. Julian, P. L.; Pikle, J. J., *J. Am. Chem. Soc.* 1935, 57, 563.
2. Lee, T. B. K and Wong, G. S. K., *J. Org. Chem.*, 1991, 56, 872.

3. Pei, X. F. and Brossi, A., *Heterocycles,* 1995, 41, 2823.
4. Lee, T. B. K. and Wong, G. S. K., *J. Chromatography,* 1990, 523, 317.
5. Pei, X. F. and Sheng, B., *Heterocycles,* 1994, 39, 557.
6. Yu, Q. S. and Brossi, A, *Heterocycles,* 1988, 27, 745.
7. Yu, Q. S. et al., *Helv. Chem. Res.* 1991, 74, 761.
8. 8. He, X. S, et al., *Med. Chem. Res.* 1992, 2, 229.
9. Pei. X. F. et al., *Med. Chem., Res.* 1995, 5, 455.
10. Yu, Q. S. et al., *J. Med. Chem.* 1988, 31, 2297.
11. Zhu, X. X., *TL,* 2000, 41, 4861.
12. Pei, X. F. et al., *Med. Chem. Res.* 1995, 5, 455.
13. 13. Yu, Q. S. et al., *J. Med. Chem.* 1997, 40, 2895.
14. Yu Q. S. et al., *Heterocycles,* 1993, 36, 1279.
15. Pei, X. F., *Helv. Chem. Acta,* 1994, 77, 1421.

What is claimed is:

1. A method of inhibiting production of amyloid precursor protein in a mammalian subject in need thereof, comprising administering transdermally to the mammalian subject an effective amount of a pharmaceutical composition comprising (+)-phenserine.

2. The method of claim 1, wherein the dosage of (+)-phenserine is from about 0.1 mg/kg to about 100 mg/kg of body weight.

3. The method of claim 2, wherein the dosage of (+)-phenserine is from about 0.1 mg/kg to about 20 mg/kg of body weight.

4. The method of claim 3, wherein the dosage of (+)-phenserine is from about 0.1 mg/kg to about 5 mg/kg of body weight.

5. The method of claim 1, wherein the pharmaceutical composition is administered daily to the mammalian subject.

6. The method of claim 5, wherein the pharmaceutical composition is administered once daily to the mammalian subject.

7. The method of claim 5, wherein the pharmaceutical composition is administered twice daily to the mammalian subject.

8. The method of claim 1, wherein the pharmaceutical composition comprises a slow release system.

9. The method of claim 1, wherein the pharmaceutical composition comprises a sustained release system.

10. The method of claim 1, wherein the pharmaceutical composition is administered by a polymer based delivery system.

11. The method of claim 1, wherein the pharmaceutical composition comprises (+)-phenserine tartrate.

12. The method of claim 1, wherein the mammalian subject is human.

13. A method of treating dementia in a mammalian subject in need thereof, comprising administering transdermally to the mammalian subject an effective amount of a pharmaceutical composition comprising (+)-phenserine.

14. The method of claim 13, wherein the dementia is Alzheimer's Disease.

15. The method of claim 13, wherein the dosage of (+)-phenserine is from about 0.1 mg/kg to about 100 mg/kg of body weight.

16. The method of claim 15, wherein the dosage of (+)-phenserine is from about 1 mg/kg to about 20 mg/kg of body weight.

17. The method of claim 16, wherein the dosage of (+)-phenserine is from about 1 mg/kg to about 5 mg/kg of body weight.

18. The method of claim 13, wherein the pharmaceutical composition is administered daily to the mammalian subject.

19. The method of claim 18, wherein the pharmaceutical composition is administered once daily to the mammalian subject.

20. The method of claim 18, wherein the pharmaceutical composition is administered twice daily to the mammalian subject.

21. The method of claim 13, wherein the pharmaceutical composition comprises a slow release system.

22. The method of claim 13, wherein the pharmaceutical composition comprises a sustained release system.

23. The method of claim 13, wherein the pharmaceutical composition is administered by a polymer based delivery system.

24. The method of claim 13, wherein the pharmaceutical composition comprises (+)-phenserine tartrate.

25. The method of claim 13, wherein the mammalian subject is human.

* * * * *